United States Patent
Martin López et al.

(10) Patent No.: US 9,428,524 B2
(45) Date of Patent: Aug. 30, 2016

(54) SYNTHETIC PROCESS FOR THE MANUFACTURE OF ECTEINASCIDIN COMPOUNDS

(75) Inventors: Mª Jesús Martin López, Madrid (ES); Andrés Francesch Solloso, Madrid (ES); Maria del Carmen Cuevas Marchante, Madrid (ES)

(73) Assignee: PHARMA MAR, S.A., Madrid (ES)

( * ) Notice: Subject to any disclaimer, the term of this patent is extended or adjusted under 35 U.S.C. 154(b) by 572 days.

(21) Appl. No.: 13/699,052

(22) PCT Filed: May 24, 2011

(86) PCT No.: PCT/EP2011/058466
§ 371 (c)(1),
(2), (4) Date: Nov. 20, 2012

(87) PCT Pub. No.: WO2011/147828
PCT Pub. Date: Dec. 1, 2011

(65) Prior Publication Data
US 2013/0066067 A1   Mar. 14, 2013

(30) Foreign Application Priority Data
May 25, 2010  (EP) .................................. 10382142

(51) Int. Cl.
*C07D 515/22*  (2006.01)

(52) U.S. Cl.
CPC .................... *C07D 515/22* (2013.01)

(58) Field of Classification Search
None
See application file for complete search history.

(56) References Cited

U.S. PATENT DOCUMENTS

| | | |
|---|---|---|
| 5,089,273 A | 2/1992 | Rinehart et al. |
| 5,256,663 A | 10/1993 | Rinehart et al. |
| 5,721,362 A | 2/1998 | Corey et al. |
| 6,124,292 A | 9/2000 | Corey |
| 6,348,467 B1 | 2/2002 | Corey |
| 6,569,859 B1 | 5/2003 | Corey |
| 6,815,544 B2 | 11/2004 | Corey |
| 7,202,361 B2 | 4/2007 | Flores et al. |
| 7,241,892 B1 | 7/2007 | Cuevas et al. |
| 7,247,629 B2 | 7/2007 | Manzanares et al. |
| 7,410,969 B2 | 8/2008 | Manzanares et al. |
| 7,417,145 B2 | 8/2008 | Fukuyama et al. |
| 7,420,051 B2 | 9/2008 | Francesch et al. |
| 7,524,956 B2 | 4/2009 | Cuevas et al. |
| 7,759,345 B2 | 7/2010 | Martinez et al. |
| 7,763,615 B2 | 7/2010 | Gallego et al. |
| RE41,614 E | 8/2010 | Corey |
| 7,767,659 B2 | 8/2010 | Barrasa et al. |
| 7,795,260 B2 | 9/2010 | Barrasa et al. |
| 7,807,833 B2 | 10/2010 | Fukuyama et al. |
| 7,820,838 B2 | 10/2010 | Fukuyama et al. |
| 7,919,493 B2 | 4/2011 | Flores et al. |
| 7,947,671 B2 | 5/2011 | Barrasa et al. |
| 8,012,975 B2 | 9/2011 | Manzanares et al. |
| 8,058,435 B2 | 11/2011 | Zhu et al. |
| 8,076,337 B2 | 12/2011 | Martinez et al. |

FOREIGN PATENT DOCUMENTS

| | | |
|---|---|---|
| JP | 2003221395 | 8/2003 |
| WO | WO 87/07610 | 12/1987 |
| WO | WO 98/12198 | 3/1998 |
| WO | WO 00/18233 | 4/2000 |
| WO | WO 00/69862 | 11/2000 |
| WO | WO 01/58905 | 8/2001 |
| WO | WO 01/77115 | 10/2001 |
| WO | WO 01/87894 | 11/2001 |
| WO | WO 01/87895 | 11/2001 |
| WO | WO 03/008423 | 1/2003 |
| WO | WO 03/014127 | 2/2003 |
| WO | WO 03/066638 | 8/2003 |
| WO | WO 2007/045686 | 4/2007 |
| WO | WO 2007/087220 | 8/2007 |

OTHER PUBLICATIONS

U.S. Appl. No. 12/337,756, filed Dec. 18, 2008, Corey.
U.S. Appl. No. 10/257,856, filed Mar. 31, 2003, Francesch.
Charupant, K. et. al. "Chemistry of renieramycins. Part 8: Synthesis and cytotoxicity evaluation of renieramycin M-jorunnamycin A analogues," Bioorganic Med. Chem. 17, pp. 4548-4558, 2009.

(Continued)

*Primary Examiner* — Noble Jarrell
(74) *Attorney, Agent, or Firm* — Kenneth H. Sonnenfeld; King & Spalding LLP

(57) ABSTRACT

This invention relates to compounds of formula II: wherein $R_1$, $R_2$, $Prot^{SH}$, and $Prot^{NH}$ are as defined, to processes for the synthesis of ecteinascidins of formula I from compounds of formula II, and to processes for the synthesis of compounds of formula II.

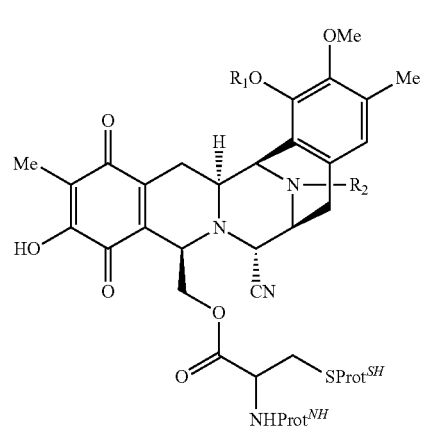

20 Claims, No Drawings

(56) References Cited

OTHER PUBLICATIONS

Cuevas, C. et. al. "Synthesis of Ecteinascidin ET-743 and Phthalascidin Pt-650 from Cyanosafracin B," Organic Letters, 2(16), pp. 2454-2458, 2000.

Daikuhara, N. et. al. "Chemistry of renieramycins. Part 7: Renieramycins T and U, novel renieramycin-ecteinascidin hybrid marine natural products from Thai sponge *Xestospongia* sp," Tetrahedron Letters 50, pp. 4276-4278, 2009.

Fishlock, et al., "Synthetic Studies on ET-743. Assembly of the Pentacyclic Core and a Formal Total Synthesis," J. Org. Chem. 73, pp. 9594-9600, 2008.

Manzanares, I. et. al. "Advances in the Chemistry and Pharmacology of Ecteinascidins, a Promising New Class of Anticancer Agents," Curr. Med. Chem, Anti-Cancer Agents, 1, pp. 257-276, 2001.

Menchaca, R. et. al. "Synthesis of Natural Ecteinascidins (ET-729, ET-745, ET-759-B, ET-736, ET-637, ET-594) from Cyanosafracin B," J. Org. Chem. 68, pp. 8859-8866, 2003.

Sakai et. al. "Additional antitumor ecteinascidins from a Caribbean tunicate: Crystal structures and activities in vivo," Proc. Natl, Acad. Sci. USA, 89, pp. 11456-11460, 1992.

SYNTHETIC PROCESS FOR THE MANUFACTURE OF ECTEINASCIDIN COMPOUNDS

The present invention relates to synthetic processes, and in particular it relates to synthetic processes for producing ecteinascidin compounds.

BACKGROUND OF THE INVENTION

Ecteinascidins is a group of naturally occurring marine compounds and analogs thereof, which are well identified and structurally characterized, and are disclosed to have antibacterial and cytotoxic properties. See for example, European Patent 309.477; WO 03/66638; WO 03/08423; WO 01/77115; WO 03/014127; R. Sakai et al., 1992, *Proc. Natl. Acad. Sci. USA* 89, pages 11456-11460; R. Menchaca et al., 2003, *J. Org. Chem.* 68(23), pages 8859-8866; and I. Manzanares et al., 2001, *Curr. Med. Chem. Anti-Cancer Agents*, 1, pages 257-276; and references therein. Examples of ecteinascidins are provided by ET-743, ET-729, ET-745, ET-759A, ET-759B, ET-759C, ET-770, ET-815, ET-731, ET-745B, ET-722, ET-736, ET-738, ET-808, ET-752, ET-594, ET-552, ET-637, ET-652, ET-583, ET-597, ET-596, ET-639, ET-641, and derivatives thereof, such as acetylated forms, formylated forms, methylated forms, and oxide forms.

The structural characterizations of such ecteinascidins are not given again explicitly herein because from the detailed description provided in such references and citations any person of ordinary skill in this technology is capable of obtaining such information directly from the sources cited here and related sources.

At least one of the ecteinascidin compounds, ecteinascidin 743 (ET-743), has been extensively studied, and it will be referred to specifically herein to illustrate features of this invention. ET-743 is being employed as an anticancer medicament, under the international nonproprietary name (INN) trabectedin, for the treatment of patients with advanced and metastatic soft tissue sarcoma (STS), after failure of anthracyclines and ifosfamide, or who are unsuited to receive such agents, and for the treatment of relapsed platinum-sensitive ovarian cancer in combination with pegylated liposomal doxorubicin.

ET-743 has a complex tris(tetrahydroisoquinoline) structure of formula

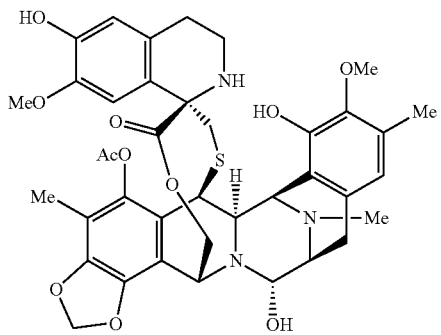 [SMILES: COc1cc2c(cc1O)CCN[C@]21CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

It was originally prepared by isolation from extracts of the marine tunicate *Ecteinascidia turbinata*. The yield was low, and alternative preparative processes had been sought.

The first synthetic process for producing ecteinascidin compounds was described in U.S. Pat. No. 5,721,362. This process employed sesamol as starting material and yielded ET-743 after a long and complicated sequence of 38 examples each describing one or more steps in the synthetic sequence.

An improvement in the preparation of one intermediate used in such process was disclosed in U.S. Pat. No. 6,815,544. Even with this improvement, the total synthesis was not suitable for manufacturing ET-743 at an industrial scale.

A hemisynthetic process for producing ecteinascidin compounds was described in EP 1.185.536. This process employs cyanosafracin B as starting material to provide ET-743. Cyanosafracin B is a pentacyclic antibiotic obtained by fermentation from the bacteria *Pseudomonas fluorescens*.

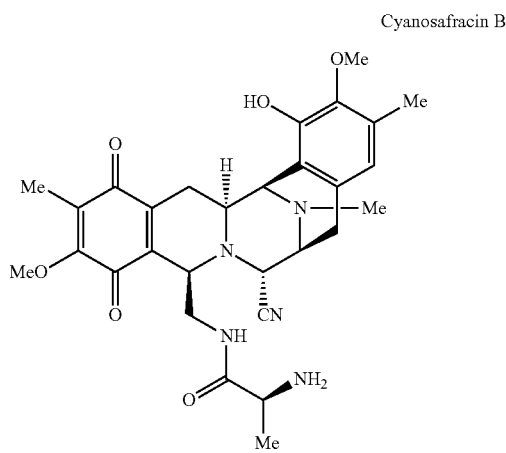 [SMILES: COC1=C(C)C(=O)C2=C(C1=O)[C@H](CNC(=O)[C@H](C)N)N1[C@@H](C#N)[C@@H]3Cc4cc(C)c(OC)c(O)c4[C@H]([C@@H]1C2)N3C]

Cyanosafracin B

An improvement in such hemisynthetic process was disclosed in EP 1.287.004.

To date four additional synthetic process (2 total and 2 formal synthesis) have been disclosed in patent applications JP 2003221395, WO 2007/045686, and WO 2007/087220 and in *J. Org. Chem.* 2008, 73, pages 9594-9600.

WO 2007/045686 also relates to the synthesis of Ecteinascidins-583 and 597 using intermediate compounds of formula:

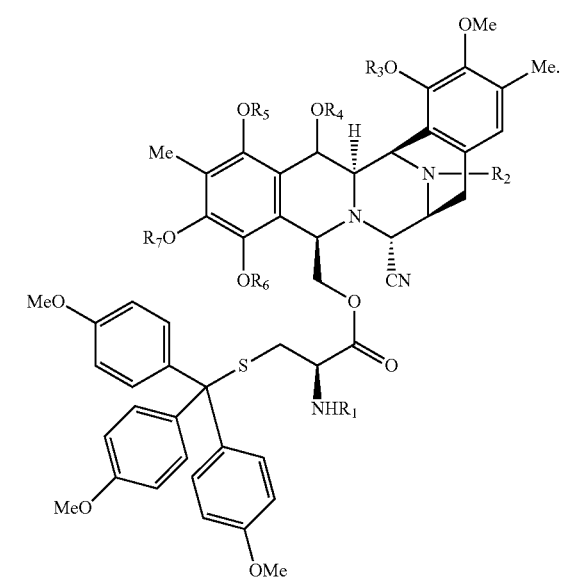

Total synthesis strategies for the synthesis of the pentacyclic core of ET-743 are overviewed in Figure I.

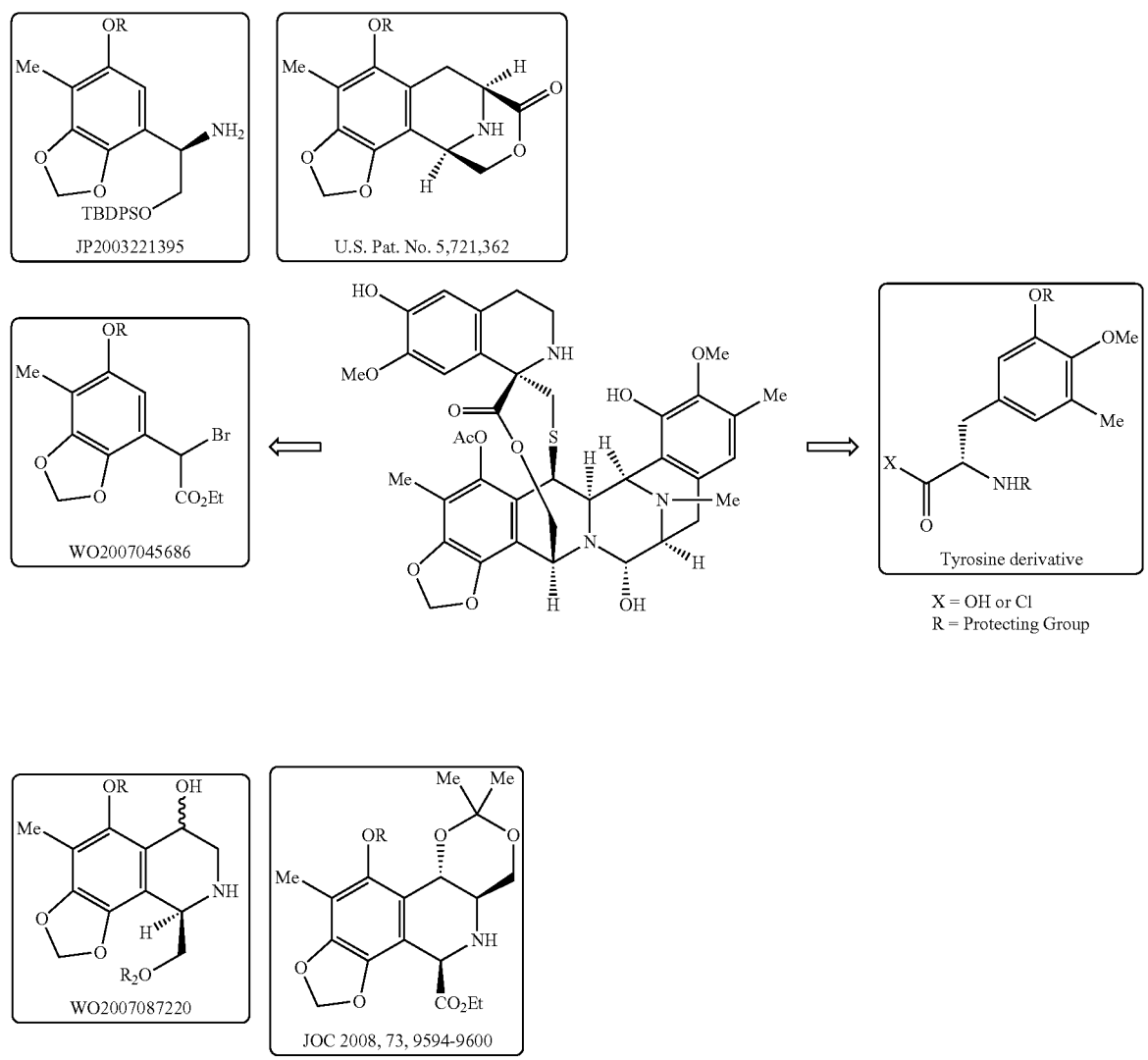

FIG. I

OBJECT OF THE INVENTION

The need remains for alternative hemisynthetic routes to the ecteinascidin compounds and related compounds. Such synthetic routes may provide more economic paths to the known antitumour agents as well as permitting the preparation of new active compounds.

SUMMARY OF THE INVENTION

This invention relates to a process for the synthesis of ecteinascidins. It also relates to intermediates for such process, to processes for their manufacture, and to their use in the synthesis of ecteinascidins.

In a first aspect, the invention relates to a process step for the manufacture of an ecteinascidin of formula I:

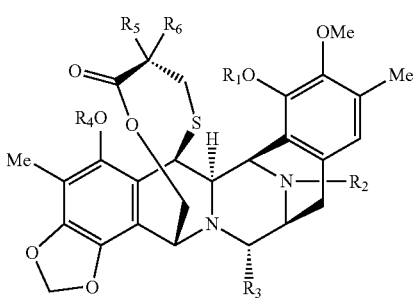

wherein
$R_1$ and $R_4$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $C(=O)R^a$, $C(=O)OR^b$, $C(=O)NR^cR^d$, and a protecting group for OH;

$R_2$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $C(=O)R^a$, $C(=O)OR^b$, $C(=O)NR^cR^d$, and a protecting group for amino;

$R_3$ is CN or OH;

$R_5$ and $R_6$ together to the carbon to which they are attached form a group:

(a) $C(=O)$;

(b) $CH(OR_7)$ or $CH(NR_8R_9)$ wherein $R_7$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for OH; and $R_8$ and $R_9$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for amino;

(c) a group of formula:

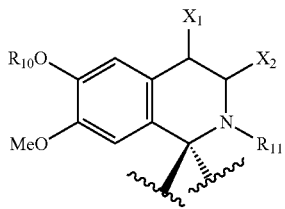

wherein $X_1$ and $X_2$ are independently selected from hydrogen and substituted or unsubstituted $C_1$-$C_{12}$ alkyl;

$R_{10}$ is selected from hydrogen, $C(=O)R^a$, $C(=O)OR^b$, $C(=O)NR^cR^d$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl and a protecting group for OH;

$R_{11}$ is selected from hydrogen, $C(=O)R^a$, $C(=O)OR^b$, $C(=O)NR^cR^d$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl and a protecting group for amino; or (d) a group of formula:

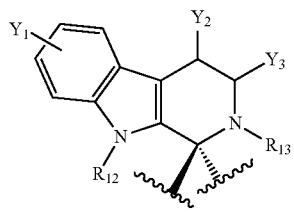

wherein $Y_1$ is selected from hydrogen, $OR^b$, $OC(=O)R^a$, $OC(=O)OR^b$, $OC(=O)NR^cR^d$, $SR^e$, $SOR^a$, $SO_2R^a$, $C(=O)R^a$, $C(=O)OR^b$, $C(=O)NR^cR^d$, $NO_2$, $NR^cR^d$, $N(R^c)C(=O)R^a$, $N(R^c)$—$OR^b$, $C(R^a)=NOR^b$, $N(R^c)C(=O)OR^b$, $N(R^c)C(=O)NR^cR^d$, CN, halogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;

$Y_2$ and $Y_3$ are independently selected from hydrogen and substituted or unsubstituted $C_1$-$C_{12}$ alkyl;

$R_{12}$ and $R_{13}$ are independently selected from hydrogen, $C(=O)R^a$, $C(=O)OR^b$, $C(=O)NR^cR^d$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and each $R^a$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group; each $R^b$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for OH;

each $R^c$ and $R^d$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for amino;

each $R^e$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for SH;

or a pharmaceutical acceptable salt thereof, wherein the process comprises the step of reducing a quinone of formula II followed by alkylation of the resulting hydroquinone with a suitable electrophilic reagent to give a compound of formula IIa in accordance with Scheme I:

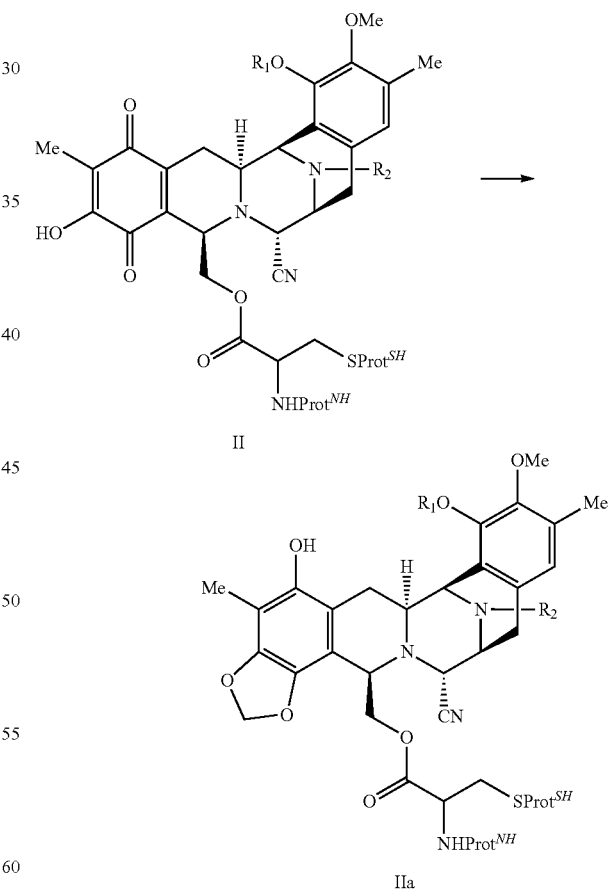

wherein $R_1$ is a protecting group for OH;

$R_2$ is selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $C(=O)R^a$, $C(=O)OR^b$, $C(=O)NR^cR^d$, and a protecting group for amino;

$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;

$R^b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for OH;

$R^c$ and $R^d$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for amino;

$Prot^{NH}$ is a protecting group for amino; and
$Prot^{SH}$ is a protecting group for SH.

In another aspect, the present invention provides intermediates of formula II:

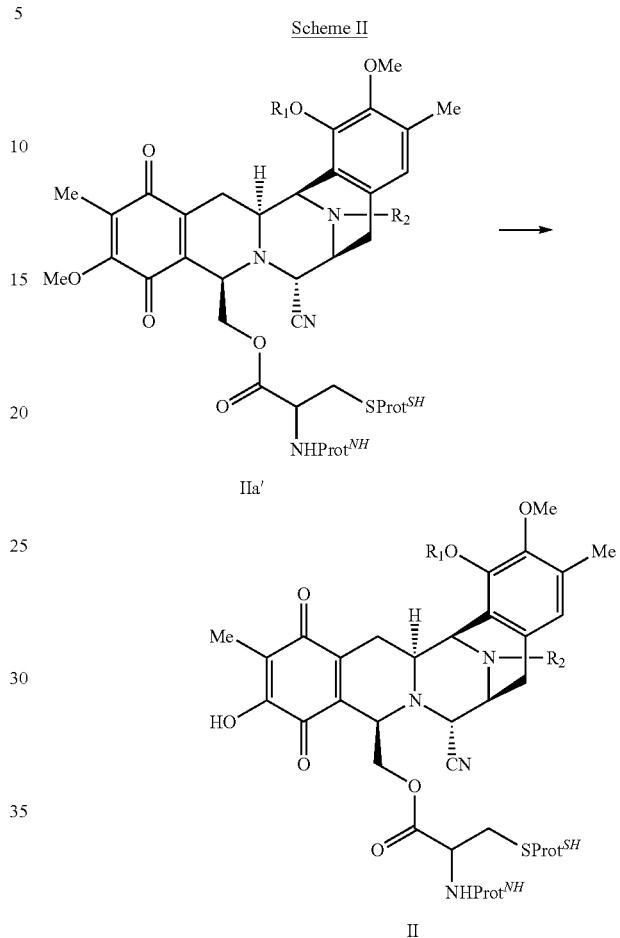

wherein
$R_1$ is a protecting group for OH;
$R_2$ is selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $C(=O)R^a$, $C(=O)OR^b$, $C(=O)NR^cR^d$, and a protecting group for amino;

$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;

$R^b$ is selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for OH;

$R^c$ and $R^d$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for amino;

$Prot^{NH}$ is a protecting group for amino; and
$Prot^{SH}$ is a protecting group for SH.

In one particular aspect, the invention relates to the use of intermediates of formula II in the manufacture of compounds of formula I.

In a further aspect, the invention relates to a process for the synthesis of a compound of formula II comprising the demethylation of a methoxybenzoquinone of formula IIa' in accordance to Scheme II:

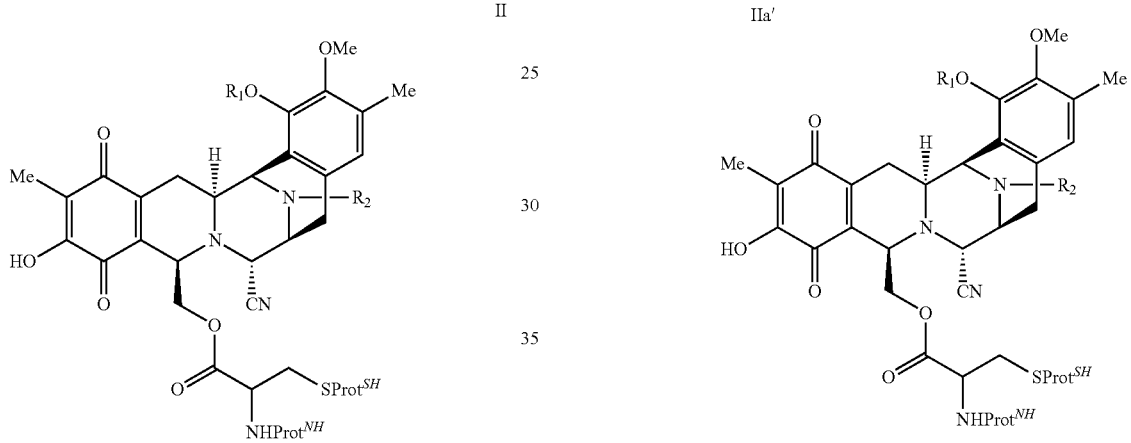

wherein $R_1$, $R_2$, $Prot^{NH}$, and $Prot^{SH}$ are as defined in formula II.

In another aspect, the invention relates to an alternative process for the synthesis of a compound of formula II comprising the deprotection and oxidation of a protected hydroquinone of formula IIa'' in accordance to Scheme III:

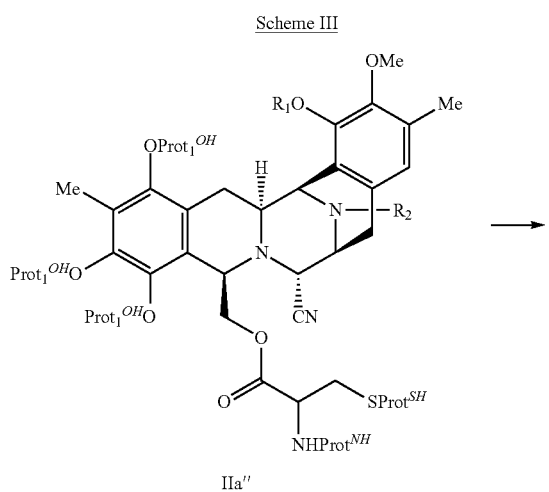

-continued

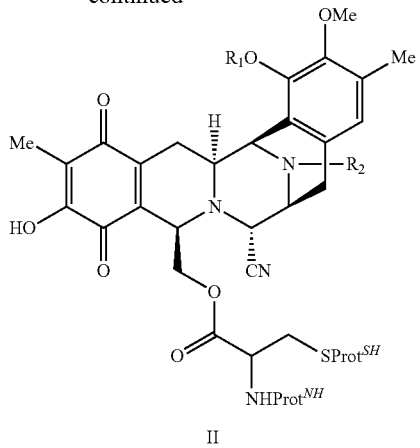

II wherein:

$R_1$ and $Prot_1^{OH}$ are protecting groups for OH, with the proviso that $R_1$ is selected to be removed selectively in the presence of $Prot_1^{OH}$ and vice versa; and $R_2$, $Prot^{NH}$, and $Prot^{SH}$ are as defined in formula II.

DETAILED DESCRIPTION OF PREFERRED EMBODIMENTS

The present invention relates to processes for the manufacture of compounds of general formula I and II as defined above.

In the compounds defined by Markush formulae in this specification, the groups can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, n-propyl, isopropyl and butyl, including n-butyl, tert-butyl, sec-butyl and isobutyl are particularly preferred alkyl groups in the compounds of the present invention.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 14 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl. The most preferred aryl group is substituted or unsubstituted phenyl.

Suitable heterocyclic groups include heteroaromatic and heteroalicyclic groups containing from 1 to 3 separated or fused rings and from 5 to about 18 ring atoms. Preferably heteroaromatic and heteroalicyclic groups contain from 5 to about 10 ring atoms, more preferably 5, 6 or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', $SO_2R'$, $NO_2$, NHR', NR'R', =N—R', NHCOR', $N(COR')_2$, $NHSO_2R'$, NR'C(=NR') NR'R', CN, halogen, COR', COOR', OCOR', OCONHR', OCONR'R', CONHR', CONR'R', protected OH, protected amino, protected SH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list.

Suitable halogen substituents in the compounds of the present invention include F, Cl, Br and I.

Suitable electrophilic reagents are compounds that react with a 1,2-dihydroxyaryl compound to give a [1,3]-dioxolo fused aryl compound. Examples of suitable electrophilic reagents include, but are not limited to, $LG_1$-$CH_2$-$LG_2$ and $LG_1$-CO-$LG_2$ where $LG_1$ and $LG_2$ are leaving groups which can be the same or different.

The term "pharmaceutically acceptable salts" refers to any pharmaceutically acceptable salt which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, nonaqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

Suitable protecting groups are well known for the skilled person in the art. A general review of protecting groups in organic chemistry is provided by Wuts, P. G. M. and Greene T. W. in Protecting groups in Organic Synthesis, 4th Ed. Wiley-Interscience, and by Kocienski P. J. in Protecting Groups, 3$^{rd}$ Ed. Georg Thieme Verlag. These references provide sections on protecting groups for OH, amino, and SH groups. All these references are incorporated by reference in their entirety.

Within the scope of the present invention an OH protecting group is defined to be the O-bonded moiety resulting from the protection of the OH group through the formation of a suitable protected OH group. Examples of such protected OH groups include ethers, silyl ethers, esters, sulfonates, sulfenates and sulfinates, carbonates, and carbamates. In the case of ethers the protecting group for the OH can be selected from methyl, methoxymethyl, methylthiomethyl, (phenyldimethylsilyl)-methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxy-phenoxy)-methyl, guaiacolmethyl, [(p-phenylphenyl)oxy]methyl, t-butoxy-methyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, O-bis(2-acetoxy-ethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxy-tetrahydrothiopyranyl S,S-dioxide, 1-[(2-chloro-4-methyl)-phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7α-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxide, 2-quinolinylmethyl, 6-methoxy-2-(4-methylphenyl-4-quinolinemethyl, 1-pyrenylmethyl, diphenylmethyl, 4-methoxydiphenylmethyl, 4-phenyl-diphenylmethyl, p,p'-dinitrobenzhydryl, 5-dibenzosuberyl, triphenylmethyl, tris (4-t-butylphenyl)methyl, α-naphthyldiphenylmethyl, p-methoxyphenyl-diphenylmethyl, di(p-methoxyphenyl) phenylmethyl, tri(p-methoxyphenyl)-methyl, 4-(4'-bromophenacyloxy)phenyldiphenyl-methyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 4,4'-dimethoxy-3"-[N-(imidazolyl-methyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenyl-methyl)-4,4"-dimethoxytrityl, 9-anthryl, 9-(9-phenyl) xanthenyl, 9-phenylthioxanthyl, 9-(9-phenyl-10-oxo) anthryl, 1,3-benzodithiolan-2-yl, and 4,5-bis (ethoxycarbonyl)-[1,3]-dioxolan-2-yl, benzisothiazolyl S,S-dioxide. In the case of silyl ethers the protecting group for the OH can be selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris (trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)-ethoxy]disiloxane-1-yl, and fluorous silyl. In the case of esters the protecting group for the OH together with the oxygen atom of the unprotected OH to which it is attached form an ester that can be selected from formate, benzoylformate, acetate, chloroacetate, dichloroacetate, trichloroacetate, trichloroacetamidate, trifluoroacetate, methoxyacetate, triphenyl-methoxy-acetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)-pentanoate, 5[3-bis(4-methoxyphenyl)hydroxymethylphenoxy] levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azido-butyrate, (2-azidomethyl)phenylacetate, 2-{[(tritylthio)oxy]methyl}benzoate, 2-{[(4-methoxytritylthio) oxy]methyl}-benzoate, 2-{[methyl(tritylthio)amino]-methyl}benzoate, 2-{{[(4-methoxytrityl)thio] methylamino}-methyl}benzoate, 2-(allyloxy)phenylacetate, 2-(prenyloxymethyl)benzoate, 6-(levulinyloxy-methyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzene-sulfonate, 4-(methylthiomethoxy)butyrate, 2-(methylthiomethoxy-methyl)benzoate, 2-(chloroacetoxymethyl)benzoate, 2-[(2-chloroacetoxy)-ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)-phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, and 2-chlorobenzoate. In the case of sulfonates, sulfenates and sulfinates the protecting group for the OH together with the oxygen atom of the unprotected OH to which it is attached form a sulfonate, sulfenate or sulfinate that can be selected from sulfate, allylsulfonate, methanesulfonate, benzylsulfonate, tosylate, 2-[(4-nitrophenyl)ethyl]-sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, and dimethylphosphinothiolyl. In the case of carbonates the protecting group for the OH together with the oxygen atom of the unprotected OH to which it is attached form a carbonate that can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl) propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH together with the oxygen atom of the unprotected OH to which it is attached form a carbamate that can be selected from dimethylthiocarbamate, N-phenylcarbamate, N-methyl-N-(o-nitrophenyl)-carbamate.

Within the scope of the present invention an amino protecting group is defined to be the N-bonded moiety resulting from the protection of the amino group through the formation of a suitable protected amino group. Examples of protected amino groups include carbamates, ureas, amides, heterocyclic systems, N-alkyl amines, N-alkenyl amines, N-alkynyl amines, N-aryl amines, imines, enamines, N-metal derivatives, N—N derivatives, N—P derivatives, N—Si derivatives, and N—S derivatives. In the case of carbamates the protecting group for the amino group together with the amino group to which it is attached form a carbamate that can be selected from methylcarbamate, ethylcarbamate, 9-fluorenylmethyl-carbamate, 2,6-di-t-butyl-9-fluorenylmethylcarbamate, 2,7-bis(trimethylsilyl)fluorenylmethylcarbamate, 9-(2-sulfo)fluorenylmethyl carbamate, 9-(2,7-dibromo)fluorenylmethylcarbamate, 17-tetrabenzo[a,c,g,i]fluorenylmethylcarbamate, 2-chloro-3-indenylmethylcarbamate, benz[f]inden-3-ylmethylcarbamate, 1,1-dioxobenzo[b]-thiophene-2-ylmethylcarbamate, 2-methylsulfonyl-3-phenyl-1-prop-2-enyloxycarbamate, 2,7-di-t-butyl-[9,(10,10-dioxo-10,10,10,10-tetraydrothioxanthyl)]methylcarbamate, 2,2,2-trichloroethylcarbamate, 2-trimethylsilylethylcarbamate, (2-phenyl-2-trimethylsilyl)ethylcarbamate, 2-phenylethylcarbamate, 2-chloroethylcarbamate, 1,1-dimethyl-2-haloethylcarbamate, 1,1-dimethyl-2,2-dibromoethylcarbamate, 1,1-dimethyl-2,2,2-trichloroethylcarbamate, 2-(2'-pyridyl) ethylcarbamate, 2-(4'-pyridyl)ethylcarbamate, 2,2-bis(4'-nitrophenyl)ethylcarbamate, 2-[(2-nitrophenyl)dithio]-1-phenylethylcarbamate, 2-(N,N-dicyclohexylcarboxamido) ethylcarbamate, t-butylcarbamate, $C_8F_{19}CH_2CH_2C(CH_3)_2$-carbamate, 1-adamantylcarbamate, 2-adamantyl carbamate, 1-(1-adamantyl)-1-methylethylcarbamate, 1-methyl-1-(4-byphenylyl)ethylcarbamate, 1-(3,5-di-t-butylphenyl)-1-methyl-ethylcarbamate, triisoropyliloxylcarbamate, vinylcarbamate, allylcarbamate, prenylcarbamate, 1-isopropylallylcarbamate, cinnamylcarbamate, 4-nitrocinnamylcarbamate, 3-(3'-pyridyl)prop-2-enylcarbamate, hexadienyloxycarbamate, propargyloxycarbamate, but-2-ynylbisoxycarbamate, 8-quinolyl-arbamate, N-hydroxypiperidinyl-carbamate, alkyldithiocarbamate, benzylcarbamate, 3,5-di-t-butylbenzylcarbamate, p-methoxybenzylcarbamate, p-nitrobenzylcarbamate, p-bromobenzylcarbamate, p-chlorobenzyl-carbamate, 2,4-dichlorobenzylcarbamate, 4-methylsulfinylbenzyl-carbamate, 4-trifluoromethylbenzylcarbamate, $C_8F_{17}CH_2CH_2$-carbamate, $(C_8F_{17}CH_2CH_2)_3Si$-carbamate, 2-naphthylmethylcarbamate, 9-anthryl-methylcarbamate, diphenylmethylcarbamate, 4-phenylacetoxybenzyl-carbamate, 4-azidobenzylcarbamate, 4-azidomethoxybenzylcarbamate, m-chloro-p-acyloxybenzylcarbamate, p-(dihydroxyboryl) benzylcarbamate, 5-benzisoxazolylmethylcarbamate, 2-(trifluoromethyl)-6-chromonylmethyl-carbamate, 2-methylthioethylcarbamate, 2-methylsulfonylethylcarbamate, 2-(p-toluenesulfonyl)-ethylcarbamate, 2-(4-nitrophenylsulfonyl) ethoxy-carbamate, 2-(2,4-dinitrophenylsulfonyl) ethoxycarbamate, 2-(4-trifluoromethylphenylsulfonyl) ethoxycarbamate, [2-(1,3-dithianyl)]methyl-carbamate, 2-phosphonioethylcarbamate, 2-[phenyl(methyl)sulfonio] ethyl-carbamate, 1-methyl-1-(triphenylphosphonio)ethylcarbamate, 1,1-dimethyl-2-cyanoethylcarbamate, 2-dansylethylcarbamate, 2-(4-nitrophenyl)ethylcarbamate, 4-methylthiophenylcarbamate, 2,4-dimethylthiophenylcarbamate, m-nitrophenylcarbamate, 3,5-dimethoxy-benzylcarbamate, 1-methyl-1-(3,5-dimethoxyphenyl)ethylcarbamate, α-methylnitro-piperonylcarbamate, o-nitrobenzylcarbamate, 3,4-dimethoxy-6-nitrobenzylcarbamate, phenyl(o-nitrophenyl)methylcarbamate, 2-nitrophenylethylcarbamate, 6-nitroveratrylcarbamate, 4-methoxyphenacyl-carbamate, 3',5'-dimethoxybenzoincarbamate, 9-xanthenylmethyl-carbamate, N-methyl-N-(o-nitrophenyl) carbamate, N-(2-acetoxyethyl)-aminecarbamate, t-amylcarbamate, 1-methylcyclobutylcarbamate, 1-methylcyclohexylcarbamate, 1-methyl-1-cyclopropylmethylcarbamate, cyclobutylcarbamate, cyclopentylcarbamate, cyclohexylcarbamate, isobutylcarbamate, isobornylcarbamate, cyclopropylmethylcarbamate, p-decyloxybenzylcarbamate, diisopropylmethylcarbamate, 2,2-dimethoxycarbonylyinylcarbamate, o-(N,N-dimethylcarboxamido) benzylcarbamate, 1,1-dimethyl-3-(N,N-dimethylcarboxamido)propylcarbamate, butynylcarbamate, 1,1-dimethylpropynylcarbamate, 2-iodoethylcarbamate, 1-methyl-1-(4'-pyridyl)ethylcarbamate, 1-methyl-1-(p-phenylazophenyl)ethyl-carbamate, p-(p'-methoxyphenylazo)benzylcarbamate, p-(phenylazo)benzylcarbamate, 2,4,6-trimethylbenzylcarbamate, isonicotinylcarbamate, 4-(trimethyl-ammonium)benzylcarbamate, p-cyanobenzylcarbamate, di(2-pyridyl)methylcarbamate, 2-furanylmethylcarbamate, phenylcarbamate, 2,4, 6-tri-t-butylphenylcarbamate, 1-methyl-1- phenylethylcarbamate, and S-benzyl thiocarbamate. In the case of ureas the protecting groups for the amino group can be selected from phenothiazinyl-(10)-carbonyl, N'-p-toluenesulfonylaminocarbonyl, N'-phenylaminothio-carbonyl, 4-hydroxyphenylaminocarbonyl, 3-hydroxytryptaminocarbonyl, and N'-phenyl-aminothiocarbonyl. In the case of amides the protecting group for the amino group together with the amino group to which it is attached form an amide that can be selected from formamide, acetamide, chloroacetamide, trichloroacetamide, trifluoroacetamide, phenyl-acetamide, 3-phenylpropanamide, pent-4-enamide, picolinamide, 3-pyridyl-carboxamide, N-benzoylphenylalanyl, benzamide, p-phenylbenzamide, o-nitrophenylacetamide, 2,2-dimethyl-2-(o-nitrophenyl)acetamide, o-nitrophenoxyacetamide, 3-(o-nitrophenyl)-propanamide, 2-methyl-2-(o-nitrophenoxy)propanamide, 3-methyl-3-nitrobutanamide, o-nitrocinnamide, o-nitrobenzamide, 3-(4-t-butyl-2,6-dinitrophenyl)-2,2-dimethylpropanamide, o-benzoyloxymethyl)-benzamide, 2-(acetoxymethyl)-benzamide, 2-[(t-butyldiphenylsiloxy)-methyl]benzamide, 3-(3',6'-dioxo-2',4', 5'-trimethylcyclohexa-1',4'-diene)-3,3-dimethylpropionamide, o-hydroxy-trans-cinnamide, 2-methyl-2-(O-phenylazophenoxy)propanamide, 4-chlorobutanamide, acetoacetamide, 3-(p-hydroxyphenyl)propanamide, (N-dithiobenzyloxycarbonylamino)-acetamide, and N-acetylmethionine amide. In the case of heterocyclic systems the protecting group for the amino group together with the amino group to which it is attached form a heterocyclic system that can be selected from 4,5-diphenyl-3-oxazolin-2-one, N-phthalimide, N-dichlorophthalimide, N-tetrachlorophthalimide, N-4-nitrophthalimide, N-thiodiglycoloyl, N-dithiasuccinimide, N-2,3-diphenylmaleimide, N-2,3-dimethylmaleimide, N-2,5-dimethylpyrrole, N-2,5-bis(triisopropylsiloxy)pyrrole, N-1,1,4,4-tetramethyldisilylazacyclo-pentane adduct, N-1,1,3,3-tetramethyl-1,3-disilaisoindoline, N-diphenylsilyldiethylene, N-5-substituted-1,3-dimethyl-1, 3,5-triazacyclohexan-2-one, N-5-substituted-1,3-benzyl-1, 3,5-triazacyclohexan-2-one, 1-substituted 3,5-dinitro-4-pyridone, and 1,3,5-dioxazine. In the case of N-alkyl, N-alkenyl, N-alkynyl or N-aryl amines the protecting group for the amino group can be selected from N-methyl, N-t-butyl, N-allyl, N-prenyl, N-cinnamyl, N-phenylallyl, N-propargyl, N-methoxymethyl, N-[2-(trimethylsilyl)ethoxy]methyl, N-3-acetoxypropyl, N-cyanomethyl, N-2-azanorbornenes, N-benzyl, N-4-methoxybenzyl, N-2,4-dimethoxybenzyl, N-2-hydroxybenzyl, N-ferrocenylmethyl, N-2,4-dinitrophenyl, o-methoxyphenyl, p-methoxyphenyl, N-9-phenylfluorenyl, N-fluorenyl, N-2-picolylamine N'-Oxide, N-7-methoxycoumar-4-ylmethyl, N-diphenylmethyl, N-bis(4-methoxyphenyl)methyl, N-5-dibenzosuberyl, N-triphenylmethyl, N-(4-methylphenyl)diphenylmethyl, and N-(4-methoxyphenyl)diphenylmethyl. In the case of imines the protecting group for the amino group can be selected from N-1,1-dimethylthiomethylene, N-benzylidene, N-p-methoxybenzylidene, N-diphenylmethylene, N-[2-pyridyl)mesityl]-methylene, N—(N',N'-dimethylaminomethylene), N—(N',N'-dibenzylaminomethylene), N—(N'-t-butylaminomethylene), N,N'-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene. In the case of enamines the protecting group for the amino group can be selected from N-(5,5-dimethyl-3-oxo-1-cyclohexenyl), N-2,7-dichloro-9-fluorenylmethylene, N-1-(4,4-dimethyl-2,6-dioxocyclohexylidene)ethyl, N-(1,3-dimethyl-2,4,6-(1H,3H,5H)-trioxopyrimidine-5-ylidene)methyl, N-4,4,4-trifluoro-3-oxo-1-butenyl, and N-(1-isopropyl-4-nitro-2-oxo-3-pyrrolin-3-yl). In the case of N-metal derivatives the protecting group for the amino group can be selected from N-borane, N-diphenylborinic acid, N-diethylborinic acid, N-9-borabicyclononane, N-difluoroborinic acid, and 3,5-bis(trifluoromethyl)phenylboronic acid; and also including N-[phenyl(pentacarbonylchromium)]carbenzyl, N-[phenyl(pentacarbonyltungsten)]carbenzyl, N-[methyl(pentacarbonylchromium)]carbenzyl, N-[methyl(pentacarbonyltungsten)]-carbenzyl, N-copper chelate, N-zinc chelate, and a 18-crown-6-derivative. In the case of N—N derivatives the protecting group for the amino group can be selected from N-nitro, N-nitroso, N-oxide, azide, triazene, and N-trimethylsilylmethyl-N-benzylhydrazine. In the case of N—P derivatives the protecting group for the amino group together with the amino group to which it is attached form a N—P derivative that can be selected from diphenylphosphinamide, dimethylthiophosphinamide, diphenylthiophosphinamide, dialkyl phosphoramidate, dibenzyl phosphoramidate, diphenyl phosphoramidate, and iminotriphenylphosphorane. In the case of N—Si derivatives the protecting group for the $NH_2$ can be selected from t-butyldiphenylsilyl and triphenylsilyl. In the case of N—S derivatives the protecting group for the amino group together with the amino group to which it is attached form a N—S derivative that can be selected from N-sulfenyl or N-sulfonyl derivatives. The N-sulfenyl derivatives can be selected from benzenesulfenamide, 2-nitrobenzenesulfenamide, 2,4-dinitrobenzenesulfenamide, pentachloro-benzenesulfenamide, 2-nitro-4-methoxybenzenesulfenamide, triphenyl-methylsulfenamide, 1-(2,2,2)-trifluoro-1,1-diphenyl)ethylsulfenamide, and N-3-nitro-2-pyridinesulfenamide. The N-sulfonyl derivatives can be selected from methanesulfonamide, trifluoromethanesulfonamide, t-butylsulfonamide, benzylsulfonamide, 2-(trimethylsilyl)ethanesulfonamide, p-toluene-sulfonamide, benzenesulfonamide, o-anisylsulfonamide, 2-nitrobenzenesulfonamide, 4-nitrobenzenesulfonamide, 2,4-dinitrobenzenesulfonamide, 2-naphthalenesulfonamide, 4-(4',8'-dimethoxynaphthylmethyl)benzenesulfonamide, 2-(4-methylphenyl)-6-methoxy-4-methylsulfonamide, 9-anthracenesulfonamide, pyridine-2-sulfonamide, benzothiazole-2-sulfonamide, phenacylsulfonamide, 2,3,6-trimethyl-4-methoxybenzenesulfonamide, 2,4,6-trimethoxybenzene-sulfonamide, 2,6-dimethyl-4-methoxybenzenesulfonamide, pentamethyl-benzenesulfonamide, 2,3,5,6-tetramethyl-4-methoxybenzenesulfonamide, 4-methoxybenzenesulfonamide, 2,4,6-trimethylbenzenesulfonamide, 2,6-dimethoxy-4-methylbenzenesulfonamide, 3-methoxy-4-t-butylbenzenesulfonamide, and 2,2,5,7,8-pentamethylchroman-6-sulfonamide.

Within the scope of the present invention an SH protecting group is defined to be the S-bonded moiety resulting from the protection of the SH group through the formation of a suitable protected SH group. Examples of such protected SH groups include thioethers, disulfides, silyl thioethers, thioesters, thiocarbonates, and thiocarbamates. In the case of thioethers the protecting group for the SH can be selected from S-alkyl, S-benzyl, S-p-methoxybenzyl, S-o-hydroxybenzyl, S-p-hydroxybenzyl, S-o-acetoxybenzyl, S-p-acetoxybenzyl, S-p-nitrobenzyl, S-o-nitrobenzyl, S-2,4, 6-trimethylbenzyl, S-2,4,6,-trimethoxybenzyl, S-4-picolyl, S-2-picolyl-N-oxide, S-2-quinolinylmethyl, S-9-anthrylmethyl, S-9-fluorenylmethyl, S-xanthenyl, S-ferrocenylmethyl, S-diphenylmethyl, S-bis(4-methoxyphenyl)methyl, S-5-dibenzosuberyl, S-triphenylmethyl, 4-methoxytrityl, S-diphenyl-4-pyridylmethyl, S-phenyl, S-2,4-dinitrophenyl, S-2-quinolyl, S-t-butyl, S-1-adamantyl, S-methoxymethyl monothioacetal, S-isobutoxymethyl monothioacetal, S-benzyloxymethyl, S-1-ethoxyethyl, S-2-tetrahydropyranyl monothioacetal, S-benzylthiomethyl dithioacetal, S-phenylthiomethyl dithioacetal, thiazolidine derivative, S-acetamidomethyl aminothioacetal (Acm), S-trimethylacetamidomethyl aminothioacetal, S-benzamidomethyl aminothioacetal, S-allyloxycarbonylaminomethyl, S—N-[2,3,5,6-tetrafluoro-4-(N'-piperidino)-phenyl-N-allyloxycarbonylamino-methyl, S-phthalimidomethyl, S-phenylacetamidomethyl, S-(2-nitro-1-phenyl)ethyl, S-2-(2,4-dinitrophenyl)ethyl, S-2-(4'-pyridyl)ethyl, S-2-cyanoethyl, S-2-(trimethylsilyl)ethyl, S-2,2-bis(carboethoxy)ethyl, S-(1-m-nitrophenyl-2-benzoyl)ethyl, S-2-phenylsulfonylethyl, S-1-(4-methylphenylsulfonyl)-2-methylprop-2-yl, and S-p-hydroxyphenacyl. In the case of disulfides the protecting group for the SH can be selected from S—S-Et, S—S-tBu [S-(tert-butylsulfanyl)cysteine, S—S-tbutyl) and S-Npys (S-3-nitro-2-pyridinesulfenyl). In the case of silyl thioethers the protecting group for the SH can be selected from the list of groups that was listed above for the protection of OH with silyl ethers. In the case of thioesters the protecting group for the SH can be selected from S-acetyl, S-benzoyl, S-2-methoxyisobutyryl, S-trifluoroacetyl, and the protecting group for the SH together with the SH group to which it is attached form a thioester that can be selected from S—N-[[p-biphenylyl)-isopropoxy]carbonyl]-N-methyl-γ-aminothiobutyrate, and S—N-(t-butoxycarbonyl)-N-methyl-γ-aminothiobutyrate. In the case of thiocarbonate protecting group for the SH can be selected from S-2,2,2-trichloroethoxycarbonyl, S-t-butoxycarbonyl, S-benzyloxycarbonyl, S-p-methoxybenzyloxycarbonyl, and S-fluorenylmethylcarbonyl. In the case of thiocarbamate the protecting group for the SH together with the SH group to which it is attached form a thiocarbamate that can be selected from S—(N-ethylcarbamate) and S—(N-Methoxymethylcarbamate).

The mention of these groups should not be interpreted as a limitation of the scope of the invention, since they have been mentioned as a mere illustration of protecting groups for OH, amino and SH groups, but further groups having said function may be known by the skill person in the art, and they are to be understood to be also encompassed by the present invention.

Suitable coupling agents are well known for the skilled person in the art. Examples of coupling agents are N,N'-dicyclohexylcarbodiimide (DCC), N-(3-dimethylaminopropyl)-N'-ethylcarbodiimide (EDC) and its salts, 1-[3-(dimethylamino)propyl]-3-ethylcarbodiimide methiodide (EDC methiodide), N,N'-diisopropylcarbodiimide, 1-tert-butyl-3-ethylcarbodiimide, N-cyclohexyl-N'-(2-morpholinoethyl) carbodiimide metho-p-toluenesulfonate (CMC), N,N'-di-tert-butylcarbodiimide, 1,3-Di-p-tolylcarbodiimide, 1,1'-carbonyldiimidazole (CDI), 1,1'-carbonyl-di-(1,2,4-triazole) (CDT), oxalic acid diimidazolide, 2-chloro-1,3-dimethylimidazolidinium chloride (DMC), 2-chloro-1,3-dimethylimidazolidinium tetrafluoroborate (CIB), 2-chloro-1,3-dimethylimidazolidinium hexafluorophosphate (CIP), 2-fluoro-1,3-dimethylimidazolidinium hexafluorophosphate (DFIH), (benzotriazol-1-yloxy)tris(dimethylamino)phosphonium hexafluorophosphate (BOP), (benzotriazol-1-yloxy)tripyrrolidinophosphonium hexafluorophosphate, 7-azabenzotriazol-1-yloxy)tripyrrolidinophosphonium hexafluorophosphate (PyAOP), bromotris(dimethylamino)phosphonium hexafluorophosphate (BRoP), chlorotripyrrolidinophosphonium hexafluorophosphate (PyClOP), bromotripyrrolidinophosphonium hexafluorophosphate, 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HBTU), O-(benzotriazol-1-yl)-N,N',N,'-tetramethyluronium tetrafluoroborate (TBTU), O-(7-azabenzotriazol-1-yl)-N,N,N',N'-tetramethyluronium hexafluorophosphate (HATU), 0-(benzotriazol-1-yl)-N,N,N',N'-bis(tetramethylene)uronium hexafluorophosphate (HBPyU), O-benzotriazol-1-yl-N,N,N',N'-bis(pentamethylene)uronium hexafluorophosphate (HBPipU), (benzotriazol-1-yloxy)dipiperidinocarbenium tetrafluoroborate (TBPipU), O-(6-chlorobenzotriazol-1-yl)-N,N,N',N'-tetramethyluronium hexafluorophosphate (HCTU), O-(6-chlorobenzotriazol-1-yl)-N,N,N',N'-tetramethyluronium (TCTU), O-(3,4-dihydro-4-oxo-1,2,3-benzotriazin-3-yl)-N,N,N',N'-tetramethyluronium tetrafluoroborate (TDBTU), O-(2-oxo-1(2H)pyridyl)-N,N,N',N'-tetramethyluronium tetrafluoroborate (TPTU), O-[(ethoxycarbonyl)cyanomethylenamino]-N,N,N',N'-tetramethyluronium hexafluorophosphate (HOTU), O-[(ethoxycarbonyl)cyanomethylenamino]-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU), dipyrrolidino (N-succinimidyloxy)carbenium (HSPyU), propylphosphonic anhydride (T3P) and S-(1-oxido-2-pyridyl)-N,N,N',N'-tetramethylthiouronium tetrafluoroborate (TOTT).

In the present description and definitions, when there are several groups $R^a$, $R^b$, $R^c$, $R^d$ or $R^e$ present in the compounds of the invention, and unless it is stated explicitly so, it should be understood that they can be each independently different within the given definition, i.e. $R^a$ does not represent necessarily the same group simultaneously in a given compound of the invention.

The compounds of formula I can be obtained synthetically from intermediates of formula II following the sequence of key reactions indicated in Scheme IV:

Scheme IV
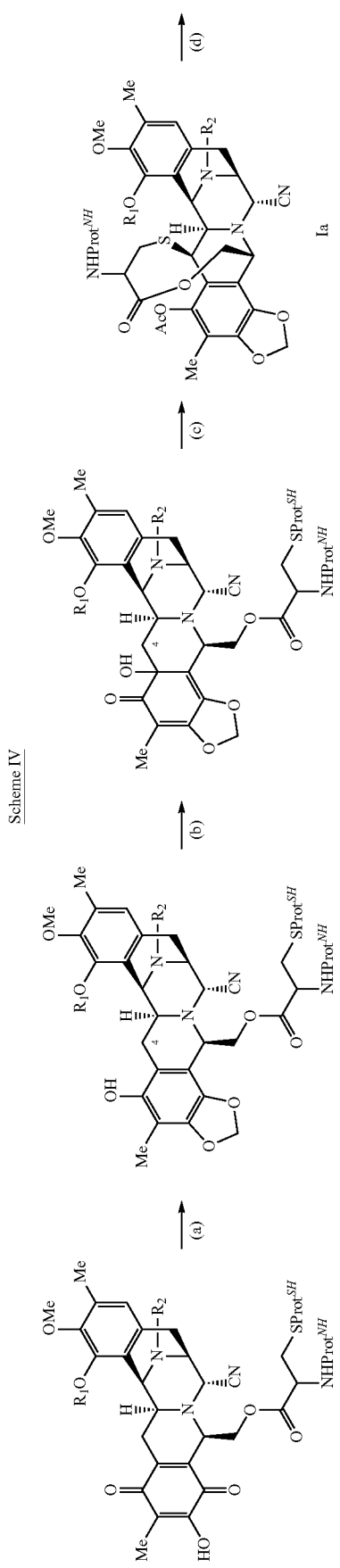

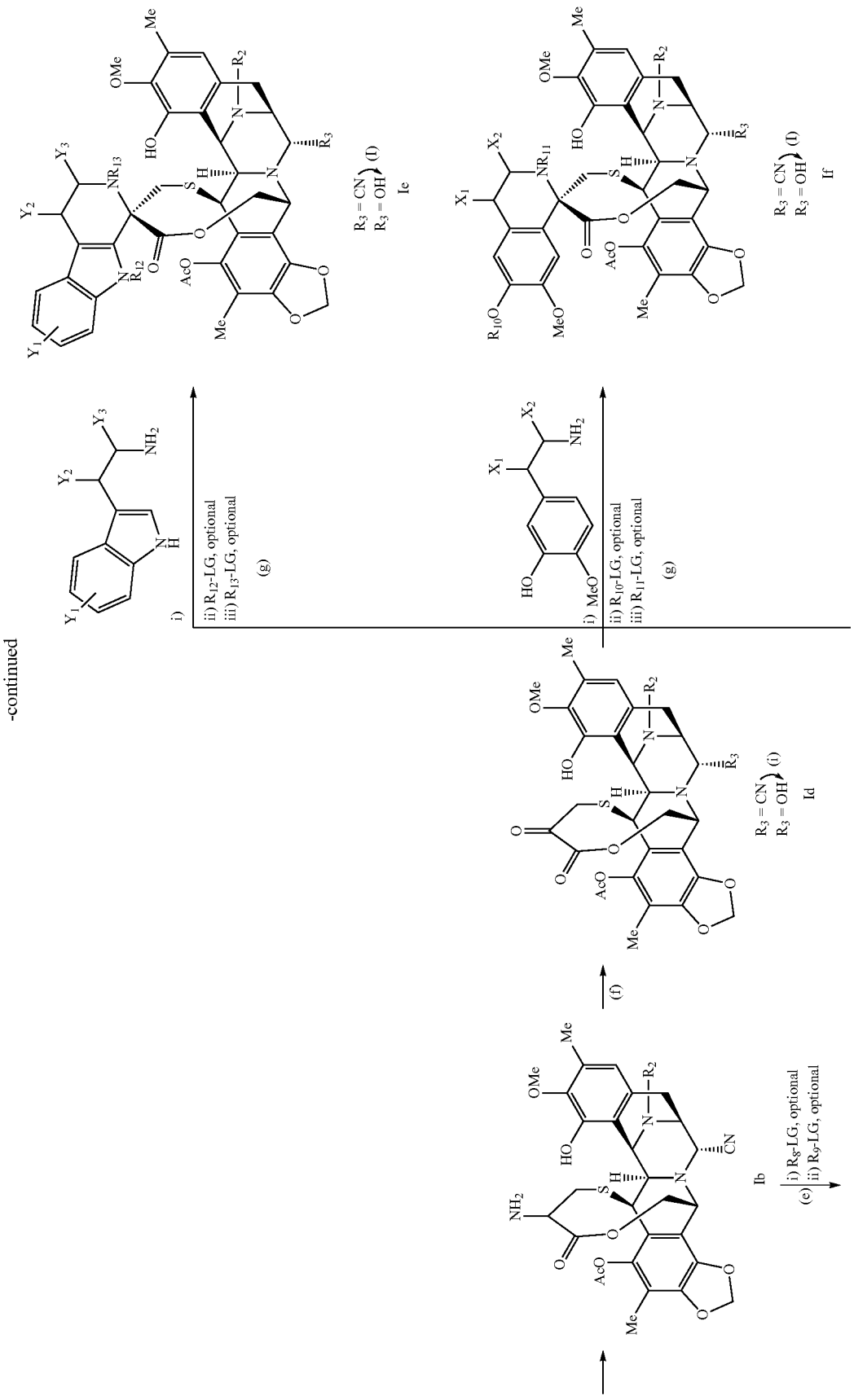

-continued
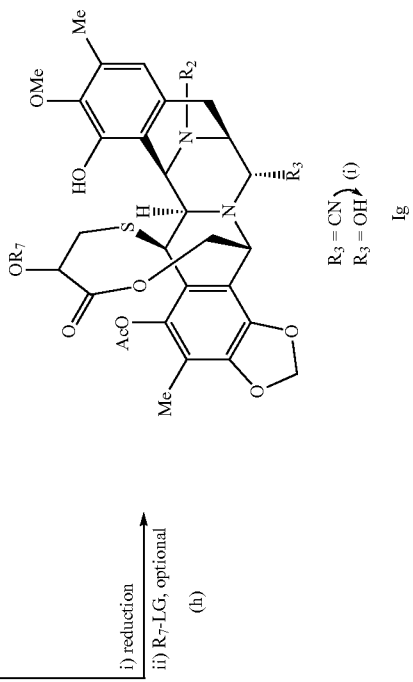
$R_3 = CN$
$R_3 = OH$ (i)
Ig
i) reduction
ii) $R_7$-LG, optional
(h)
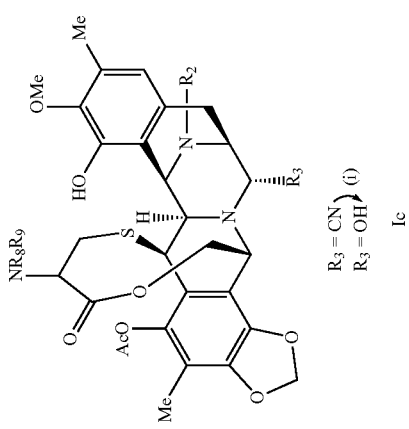
$R_3 = CN$
$R_3 = OH$ (i)
Ic wherein R₁, R₂, Prot^{NH}, and Prot^{SH} in the compounds of formula II, IIa, IIIb, Ia, and Ib are as defined above in intermediates of formula II;

R₂, R₃, R₇, R₈, R₉, R₁₀, R₁₁, R₁₂, R₁₃, X₁, X₂, Y₁, Y₂, and Y₃ in the compounds of formula Ic, Id, Ie, If, and Ig are as defined above in ecteinascidins of formula I;

LG is a leaving group; and

R₇, R₈, R₉, R₁₀, R₁₁, R₁₂, and R₁₃ in the compounds of formula R₇-LG, R₈-LG, R₉-LG, R₁₀-LG, R₁₁-LG, R₁₂-LG, and R₁₃-LG, respectively, are as defined above in ecteinascidins of formula I with the proviso that they are not hydrogen.

Examples of leaving groups include, but are not limited to, iodine, bromine, chlorine, tosylate, mesylate, nosylate, betylate, alkyl fluorosulfonate, triflate, and nonaflate.

In general, the conversion of the intermediates of formula II to an ecteinascidin compound of formula I may involve one or more of the following key transformations as needed:

(a) Reduction of the quinone group in the compound of formula II followed by alkylation of the resulting hydroquinone with a suitable electrophilic reagent to give a compound of formula IIa.

(b) Oxidation of the compound of formula IIa to give a compound of formula IIb.

(c) Formation of the bridged ring system to provide a compound of formula Ia.

(d) Deprotection of the phenol and amino groups to give a compound of formula Ib.

(e) Conversion of the compound of formula Ib to give a compound of formula Ic.

(f) Oxidation of the α-aminolactone of formula Ib to the corresponding α-ketolactone of formula Id by transamination.

(g) Stereospecifically forming of a spirotetrahydro-1H-pyrido[3,4-b]indole of formula Ie or a spirotetrahydroisoquinoline of formula If by a Pictet-Spengler reaction from the α-ketolactone of formula Id.

(h) Reduction of the α-ketolactone of formula Id to the corresponding α-hydroxylactone of formula Ig.

(i) Replacing the cyano in R₃ by a hydroxy group.

Step (a) is typically effected by reduction of the quinone system into a hydroquinone using a transition-metal catalysed hydrogenation or a reducing reagent such as Na₂S₂O₄, followed by trapping with a suitable electrophile reagent, such as CH₂Br₂, BrCH₂Cl or a similar divalent reagent, directly yielding the methylenedioxy ring system; or with a divalent reagent, such as thiocarbonyldiimidazole, which yields a substituted methylenedioxy ring system that can be converted to the desired ring.

Step (b) is typically effected by reaction with a suitable oxidant, for example with hydrogen peroxide, an organic peroxide, a perbenzoic acid, a periodate, lead tetraacetate, lead oxide, selenium dioxide, hypervalent iodine oxidants such as 2-iodoxybenzoic acid (IBX), or with an organic seleninic anhydride such as (PhSeO)₂O. More preferred oxidants are organic seleninic anhydrides and hypervalent iodine oxidants. Organic seleninic anhydrides are even more preferred. The most preferred oxidant is (PhSeO)₂O.

Step (c) is typically effected by forming an exendo quinone methide at the 4-position of ring B, allowing the methide to react with the sulphur atom of the cysteine residue and capturing the resulting phenoxide with an acetylating reagent such as acetic anhydride, a mixed acetyl anhydride, or acetyl chloride to give a compound of formula Ia. Suitable the methide is formed by reaction of the compound of formula IIb with the in situ-generated Swern reagent, followed by treatment with a base. Suitable the cyclization is carried out by removing the protecting group for SH under conditions that allow the formation of a thiolate ion, followed by nucleophile addition of sulphur to the quinone methide to generate the 10-membered lactone bridge, and the resulting phenoxide is captured to give the acetate of formula Ia.

Step (d) is preferably effected by deprotection of the phenol and amino groups in a single step rather than as two separate steps. More preferably, the one-pot deprotection is carried out under acidic conditions.

Step (e) is carried out when R₈ and/or R₉ are not hydrogen and is typically effected by reaction with a compound of formula R₈LG or R₉LG and, when both R₈ and R₉ are not hydrogen, followed by a second reaction with a compound of formula R₉LG or R₈LG, respectively.

Step (f) is typically effected by an oxidative conversion of the amino group into the corresponding oxo group by reaction with a suitable carbonyl reagent such as a hindered 1,2-benzoquinone or a pyridine- or pyridinium carboxaldehyde. More preferred carbonyl reagents are the methiodide of pyridine-4-carboxaldehyde and the methylbencene-sulfonate of pyridine-4-carboxaldehyde.

Step (g) is typically effected by Pictet-Spengler reaction with a β-arylethylamine of formula:

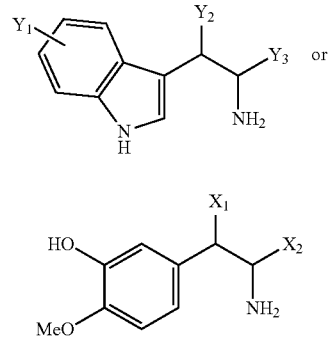

wherein Y₁, Y₂, Y₃, X₁, and X₂ are as defined above in ecteinascidins of formula I.

Step (h) is typically effected by reaction with a suitable reducing reagent. Examples of suitable reducing reagents are alkoxy aluminum hydrides and boron hydrides, for example borohydrides and cyanoborohydrides. More preferred reducing reagents are borohydrides and cyanoborohydrides. The most preferred reducing reagent is NaCNBH₃ in the presence of acetic acid.

Step (i) is typically carried out by reaction with a nitrile-coordinating transition metal salt. More preferred salts are salts of Ag(I) or Cu(I). The most preferred salts are AgNO₃ and CuCl.

Further transformations may be required to obtain certain compounds of formula I and for this purpose the procedures described in WO 01/87895, WO 03/014127, WO 03/66638, WO 03/08423 and WO 01/77115, which are incorporated herein in full by reference, can be followed.

Preferred processes for the synthesis of compounds of formula Ie are those that provide compounds of formula Ie':

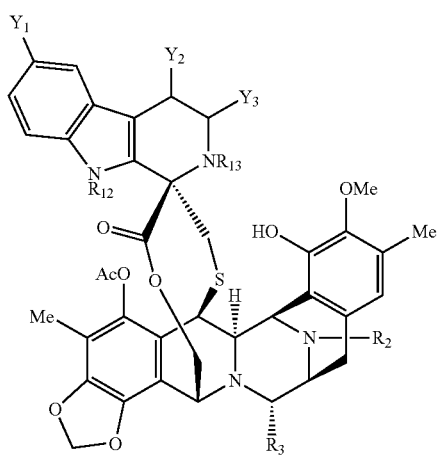

Ie' where $R_2$, $R_3$, $R_{12}$, $R_{13}$, $Y_1$, $Y_2$, and $Y_3$ are as defined above in ecteinascidins of formula I.

Particularly preferred processes for the synthesis of compounds of formula I are those that provide compounds of formula Ic, Id, Ie, Ie', If, or Ig wherein $R_2$ is methyl, $R_3$ is hydroxy, $X_1$, $X_2$, $Y_2$, $Y_3$, $R_7$, $R_8$, $R_9$, $R_{10}$, $R_{11}$, $R_{12}$, and $R_{13}$ are hydrogen, and $Y_1$ is selected from hydrogen and methoxy.

Particularly preferred processes for the synthesis of compounds of formula I are those that employ ether protected OH groups. More preferably ether protected OH groups are methoxyethoxymethyl ether and methoxymethyl ether. The most preferred ether protected OH group is methoxyethoxymethyl ether.

Particularly preferred processes for the synthesis of compounds of formula I are those that employ carbamate protected amino groups. More preferably carbamate protected amino groups are selected from allylcarbamate, 2,2,2-trichloroethylcarbamate, benzylcarbamate, 9-fluorenylmethyl-carbamate, and t-butylcarbamate. The most preferred carbamate protected amino group is t-butylcarbamate.

Particularly preferred processes are those that employ thioether protected SH groups. More preferably thioether protected SH groups are substituted or unsubstituted S-9-fluorenylmethyl thioethers. The most preferred thioether protected SH group is S-9-fluorenylmethyl (Fm) thioether.

More preferred processes for the synthesis of compounds of formula I are those that give compounds of formula:

ET-743

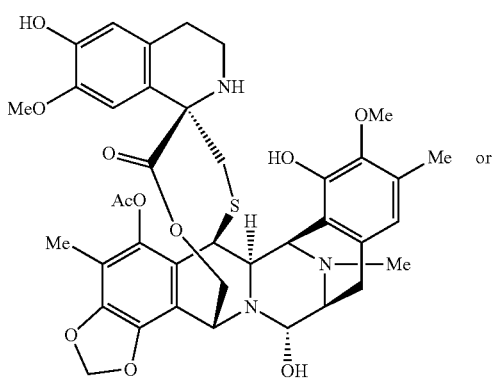

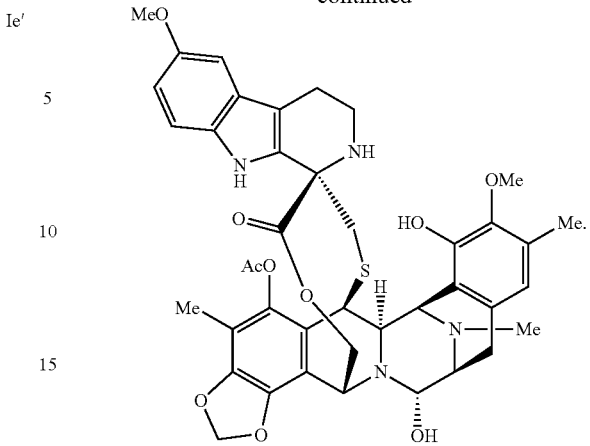

In addition, with this invention we provide novel intermediate compounds of formula II:

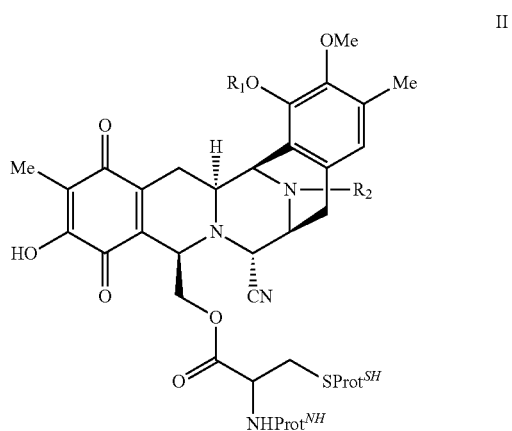

II wherein $R_1$, $R_2$, $Prot^{SH}$ and $Prot^{NH}$ are as defined above in the previous disclosure of intermediates of formula II.

In compounds of formula II, particularly preferred $R_1$ is a protecting group for OH that together with the O atom to which it is attached form an ether. More preferably $R_1$ is methoxyethoxymethyl or methoxymethyl. The most preferred $R_1$ is methoxyethoxymethyl.

Particularly preferred $R_2$ is a substituted or unsubstituted $C_1$-$C_6$ alkyl, a substituted or unsubstituted $C_2$-$C_6$ alkenyl or $C(=O)OR^b$, where $R^b$ is selected from substituted or unsubstituted $C_1$-$C_6$ alkyl and substituted or unsubstituted $C_2$-$C_6$ alkenyl. Particularly preferred $R_2$ is an unsubstituted $C_1$-$C_6$ alkyl or an unsubstituted $C_2$-$C_6$ alkenyl. More preferably $R_2$ is methyl or allyl. The most preferred $R_2$ is methyl.

Particularly preferred $Prot^{NH}$ is a protecting group for amino that together with the N atom to which is attached form a carbamate. More preferably $Prot^{NH}$ is selected from allyloxycarbonyl, 2,2,2-trichloroethyloxycarbonyl, benzyloxycarbonyl, 9-fluorenylmethyloxycarbonyl, and t-butyloxycarbonyl. The most preferred $Prot^{NH}$ is t-butyloxycarbonyl.

Particularly preferred $Prot^{SH}$ is a protecting group for SH that together with the S group to which is attached form a thioether. More preferably $Prot^{SH}$ is a substituted or unsubstituted S-9-fluorenylmethyl. The most preferred $Prot^{SH}$ is S-9-fluorenylmethyl (Fm).

Suitable starting materials for the synthesis of the intermediates of formula II include compounds related to the natural bis(tetrahydroisoquinoline) alkaloids. Such starting materials may be prepared either from the different classes of saframycin and safracin antibiotics available from different culture broths as detailed in WO 00/69862 or by other synthetic or biochemical processes such as those disclosed in U.S. Pat. No. 5,721,362, U.S. Pat. No. 6,815,544, JP 2003221395, WO 2007/045686, WO 2007/087220 and J. Org. Chem. 2008, 73, 9594-9600, which are all incorporated herein in full by reference.

In one embodiment, compounds of formula II are obtained from cyanosafracin B following the sequence of reactions indicated in Scheme V:

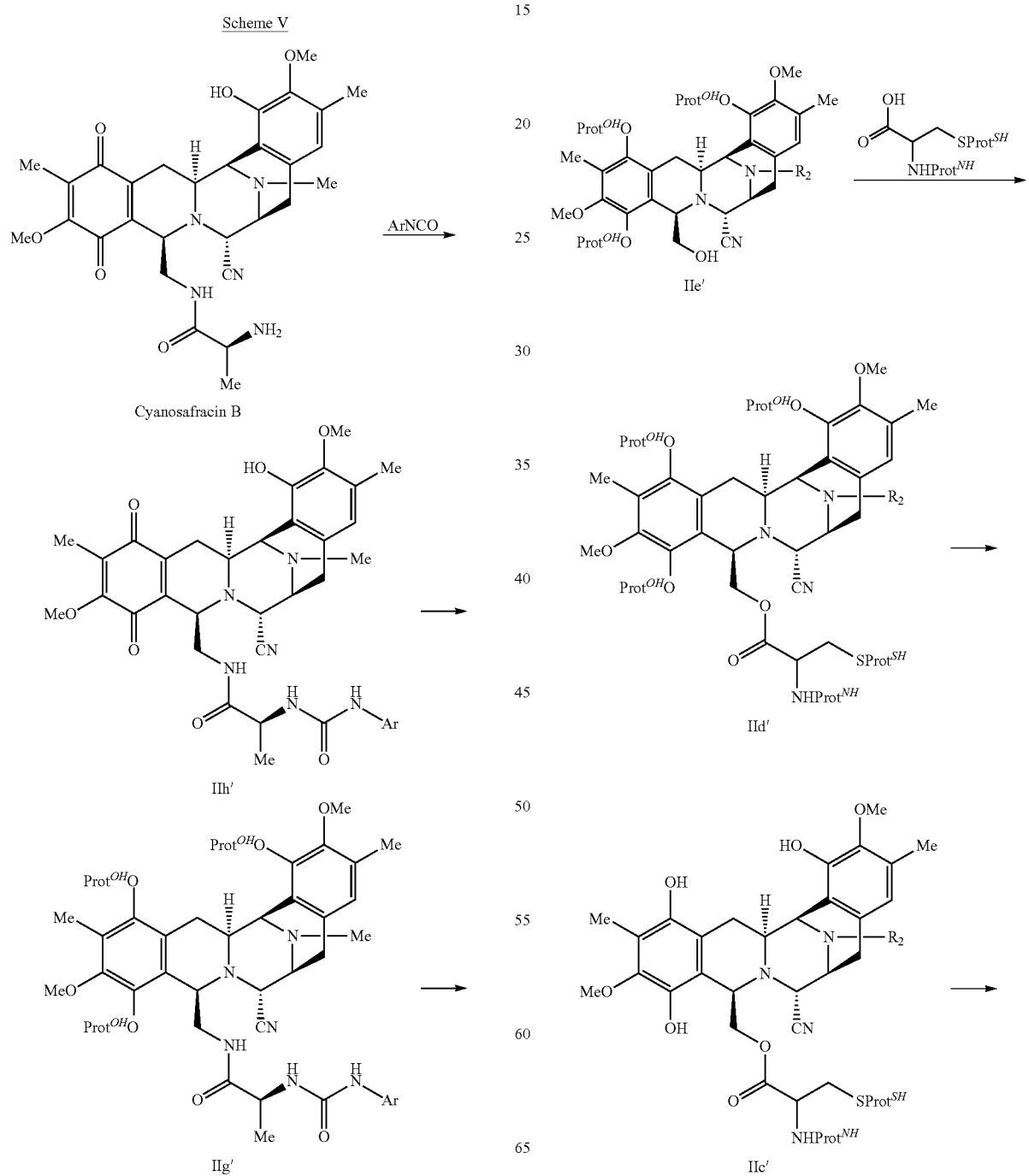

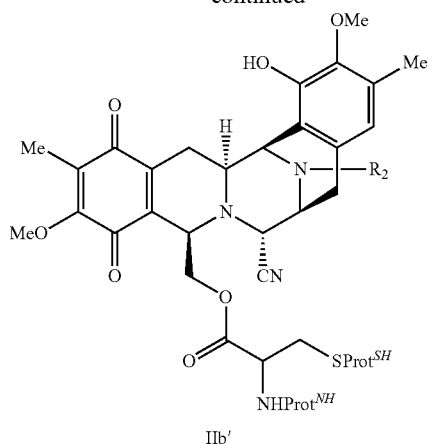

IIb'

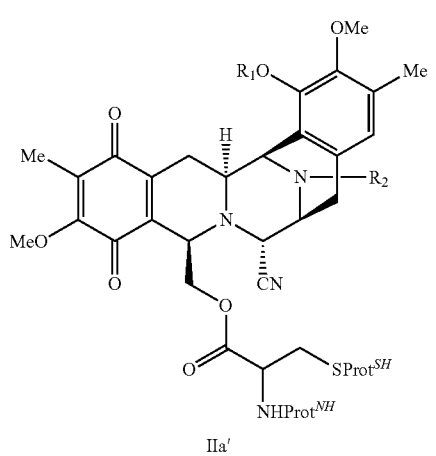

IIa'

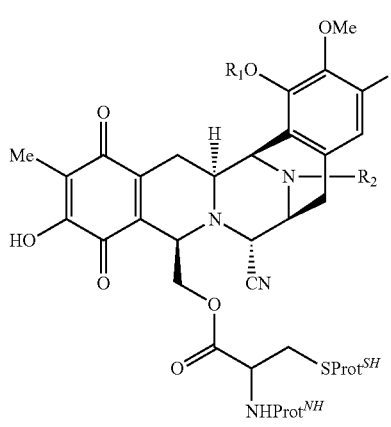

II wherein:
Prot$^{OH}$ is a protecting group for OH;
Ar is a substituted or unsubstituted aryl group;
Prot$^{NH}$ is a protecting group for amino;
Prot$^{SH}$ is a protecting group for SH; and
R$_1$ and R$_2$ are as defined above in formula II.

Accordingly, in this embodiment, the process for the synthesis of a compound of formula II comprises the step of demethylating a methoxyquinone of formula IIa':

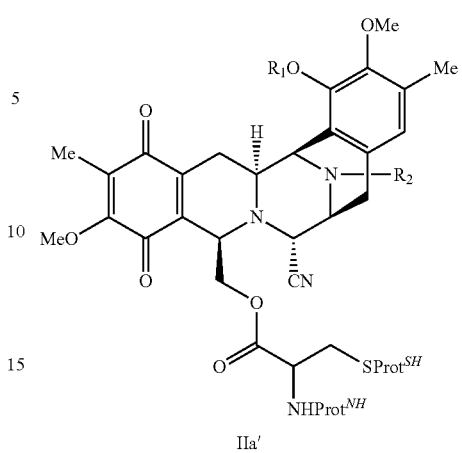

IIa'

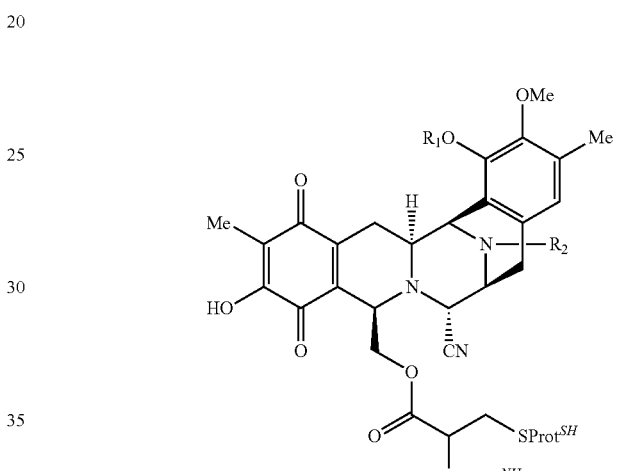

II wherein R$_1$, R$_2$, Prot$^{NH}$ and Prot$^{SH}$ are as defined above in the previous disclosure of intermediates of formula II.

Moreover, this process can further comprise the step of preparing the compound of formula IIa' by protecting a phenol of formula IIb':

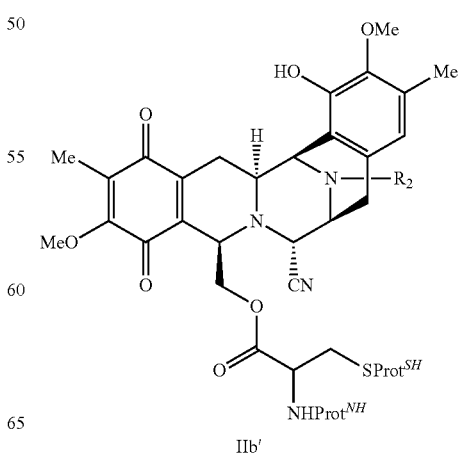

IIb'

-continued

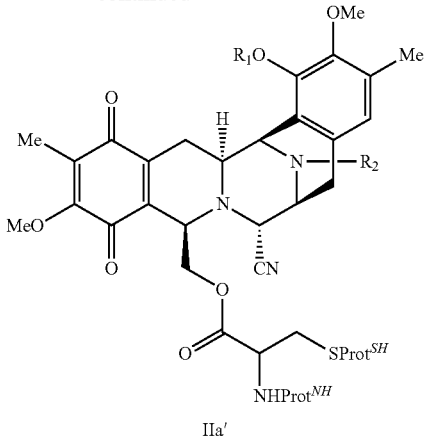

IIa' wherein $R_1$, $R_2$, $Prot^{NH}$ and $Prot^{SH}$ are as defined above in the previous disclosure of intermediates of formula II.

Moreover, this process can further comprise the step of preparing the compound of formula IIb' by oxidation of a hydroquinone of formula IIc':

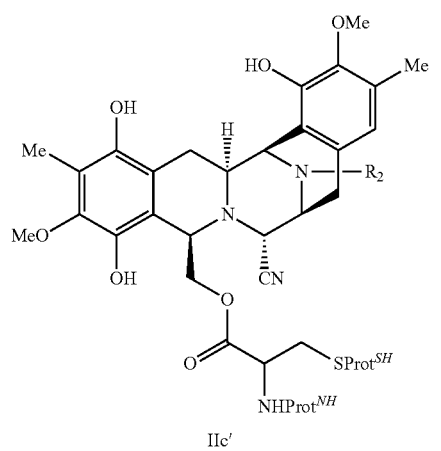

IIc'

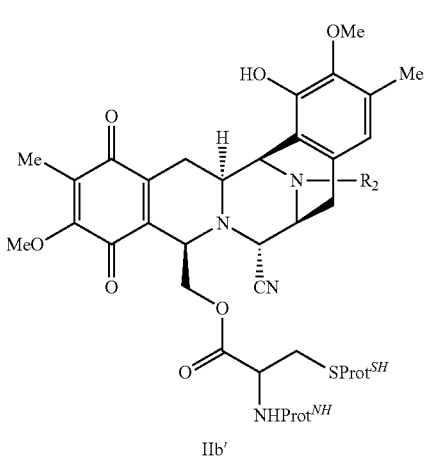

IIb' wherein $R_2$, $Prot^{NH}$ and $Prot^{SH}$ are as defined above in the previous disclosure of intermediates of formula II.

Moreover, this process can further comprise the step of preparing a compound of formula IIc' by deprotection of a compound of formula IId':

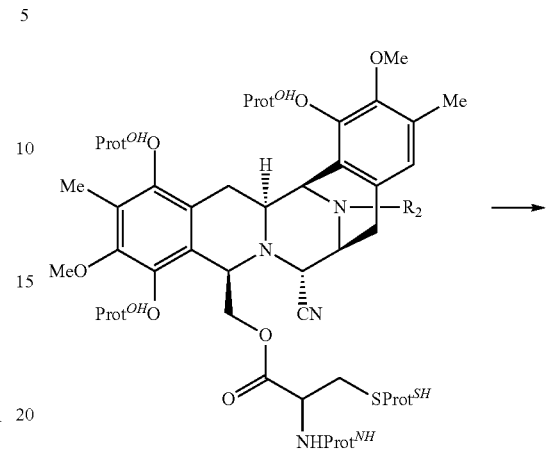

IId'

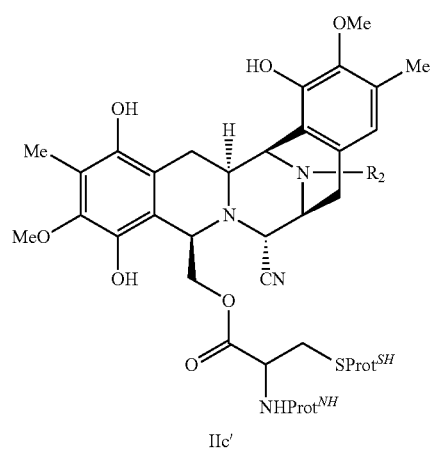

IIc' wherein $R_2$, $Prot^{OH}$, $Prot^{NH}$ and $Prot^{SH}$ are as defined above in the previous disclosure of intermediates of formula II.

Moreover, this process can further comprise the step of preparing the compound of formula IId' by coupling the primary hydroxyl group in a compound of formula IIe' with a protected cysteine derivative:

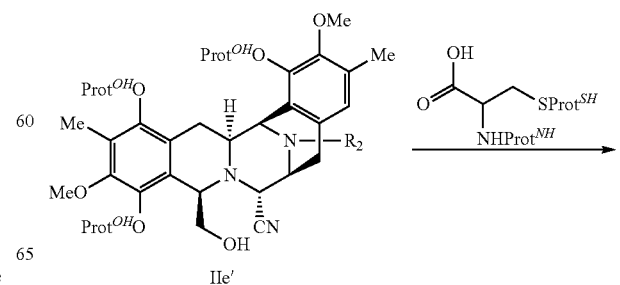

IIe'

-continued

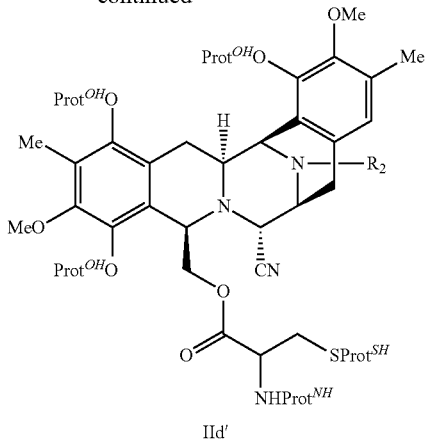

IId' wherein $R_2$, $Prot^{OH}$, $Prot^{NH}$ and $Prot^{SH}$ are as defined above in the previous disclosure of intermediates of formula II.

Moreover, this process can further comprise the step of preparing the compound of formula IIe' by converting a primary amine of formula IIf' to a primary alcohol with a suitable oxidizing reagent and, optionally, when $R_2$ in the compound of formula IIe' is not methyl, followed by protecting the primary alcohol with a silyl protecting group for OH, demethylating the NMe group, reacting the resulting secondary amine with a compound of formula $R_2$-LG wherein LG is a leaving group and $R_2$ is as defined in formula II except methyl and hydrogen, and deprotecting the silyl-protected primary alcohol:

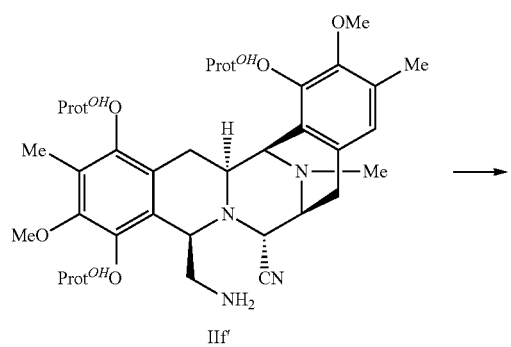

IIf'

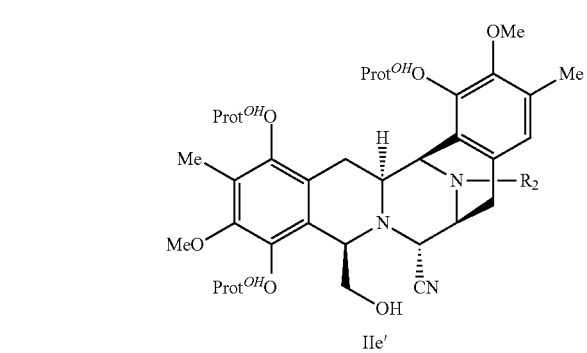

IIe' wherein $R_2$ is as defined above in the previous disclosure of intermediates of formula II and $Prot^{OH}$ is a protecting group for OH.

Moreover, this process can further comprise the step of preparing the compound of formula IIf' by amidolysis of a compound of formula IIg':

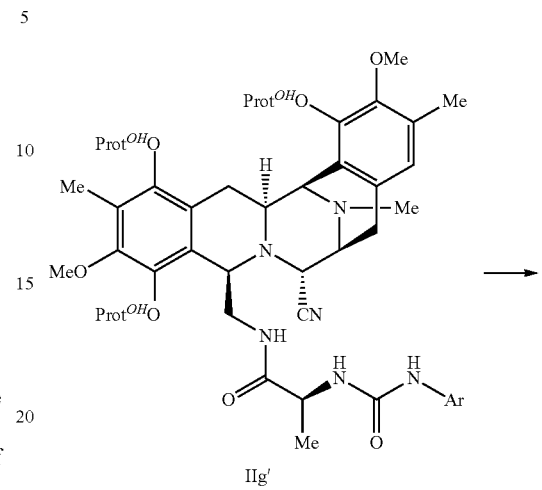

IIg'

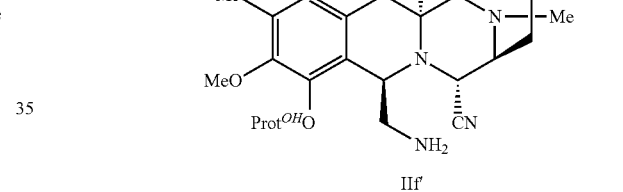

IIf' wherein $Prot^{OH}$ is a protecting group for OH and Ar is a substituted or unsubstituted aryl group.

Moreover, this process can further comprise the step of preparing a compound of formula IIg' by reduction of the quinone of formula IIh' followed by protection of the hydroxy groups:

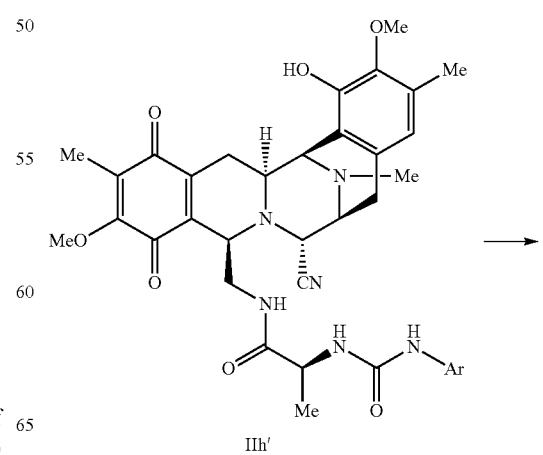

IIh'

-continued

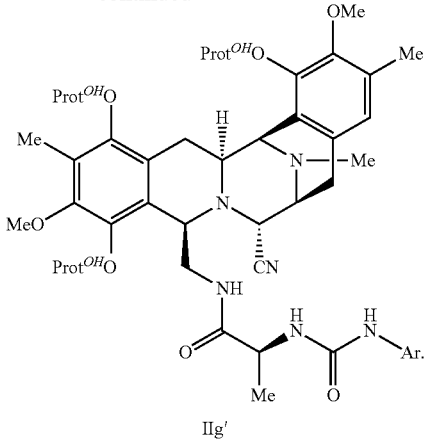

IIg' wherein Prot$^{OH}$ is a protecting group for OH and Ar is a substituted or unsubstituted aryl group.

Moreover, this process can further comprise the step of preparing a compound of formula IIh' by reaction of cyanosafracin B with a substituted or unsubstituted arylisocyanate:

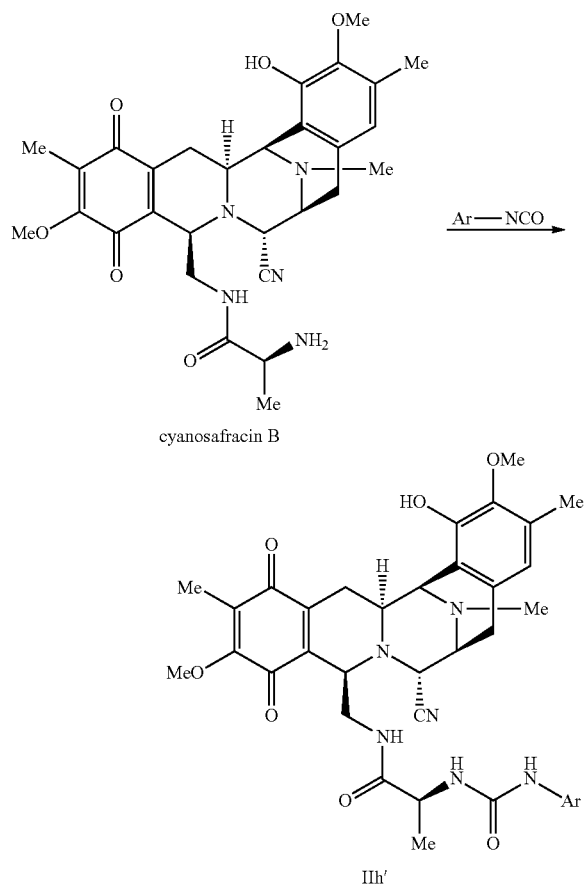

wherein Ar is a substituted or unsubstituted aryl group.

The conversion of the methoxyquinone of formula IIa' to give the compound of formula II is typically carried out by reaction with a suitable reagent for the deprotection of methoxy groups. Preferred reagent for such reaction is LiI in presence of a base such as an optionally substituted quinoline or collidine. More preferred base is a collidine. The most preferred base is 2,4,6-collidine.

The protection of the phenol of formula IIb' to give a compound of formula IIa' is typically carried out by reaction with a suitable reagent for the protection of phenol groups. Preferred reagents for such reaction are alkoxymethyl chlorides, alkoxymethylbromides and alkoxyalkoxymethyl chlorides. Alkoxyalkoxymethyl chlorides are particularly preferred reagents. The most preferred reagent is methoxyethoxymethyl chloride (MEMCl).

The oxidation of the hydroquinone of formula IIc' to give a compound of formula IIb' is carried out by reaction with a suitable oxidizing reagent. Particularly preferred oxidants are oxygen and Pd-oxygen. The most preferred oxidant is Pd/C-oxygen.

Deprotection of the phenol groups in a compound of formula IId' to give a hydroquinone of formula IIc' is carried out under conditions very well known by an expert in the art taking into account the structure of Prot$^{OH}$. Particularly preferred conditions are those employed for the deprotection of allyl protected phenol groups. Most preferred is a palladium catalyzed deprotection in presence of a reducing reagent such as a trialkyltin hydride.

The preparation of a compound of formula IId' from a compound of formula IIe' is typically carried out by reaction with an amino- and sulphur-protected cysteine amino acid wherein the amino acid is activated by a coupling agent such as a carbodiimide, a phosphonium salt, an uronium salt, a guanidinium salt, an imidazolium derived reagent, or a triazolium derived reagent. Particularly preferred coupling agents are carbodiimides. Most preferred coupling agents are 1-ethyl-3-(3-dimethylaminopropyl)-carbodiimide (EDC) and its chlorohydrate (EDC.HCl).

The conversion of the primary amine of formula IIf' to the primary alcohol of formula IIe' is typically carried out by reaction with a suitable oxidizing reagent such as an inorganic nitrite, nitrogen tetroxide or a nitroferricyanide. More preferred oxidizing reagents are inorganic nitrites. Sodium nitrite is the most preferred oxidizing reagent for this step.

The optional demethylation during the synthesis of a compound of formula IIe' typically involves a reaction with a suitable oxidant to provide the corresponding N-oxide. Particularly preferred oxidants for such reaction are peracids. The most preferred oxidant is m-chloroperbenzoic acid.

The conversion of the compound of formula IIg' to provide a primary amine of formula IIf' is carried out by reaction with a suitable amidolysis reagent. Particularly preferred is the use of chlorotrimethylsilane/methanol or iodotrimethylsilane as amidolysis reagents.

The reduction of the quinone group in the compound of formula IIh' is typically carried out using a transition metal catalysed hydrogenation or a reducing reagent such as Na$_2$S$_2$O$_4$. A transition metal catalysed hydrogenation is particularly preferred. The most preferred transition metal catalyst is Pd/C. The protection of the hydroxy groups of the intermediate compound to give a compound of formula IIg' is typically carried out by reaction with a suitable reagent for the protection of phenol groups. Preferred reagents for such reaction are allyl halides and allyloxycarbonyl halides. More preferred reagents for such reactions are allyl halides. The most preferred reagent is allyl bromide.

The formation of the urea of formula IIh' from cyanosafracin B is typically carried out by reaction with an aryl isocyanate. The most preferred reagent is phenylisocyanate.

In this process, the use of ether protected OH groups is particularly preferred. More preferably the ether protected groups are selected from alkyl silyl ethers, allyl ether, methoxyethoxymethyl ether, and methoxymethyl ether. The most preferred ether protected OH groups are allyl and methoxyethoxymethyl ether.

In this process, particularly preferred Ar group is phenyl.

In this process, the use of carbamate protected NH groups is particularly preferred. More preferably carbamate protected amino groups are selected from allylcarbamate, 2,2,2-trichloroethylcarbamate, benzylcarbamate, 9-fluorenylmethyl-carbamate, and t-butylcarbamate. The most preferred carbamate protected amino group is t-butylcarbamate.

In this process, the use of thioether protected SH groups is particularly preferred. More preferably thioether protected SH groups are substituted or unsubstituted S-9-fluorenylmethyl thioethers. The most preferred thioether protected SH group is S-9-fluorenylmethyl (Fm) thioether.

In another embodiment, the compounds of formula II can also be obtained from cyanosafracin B following the sequence of reactions indicated in Scheme VI:

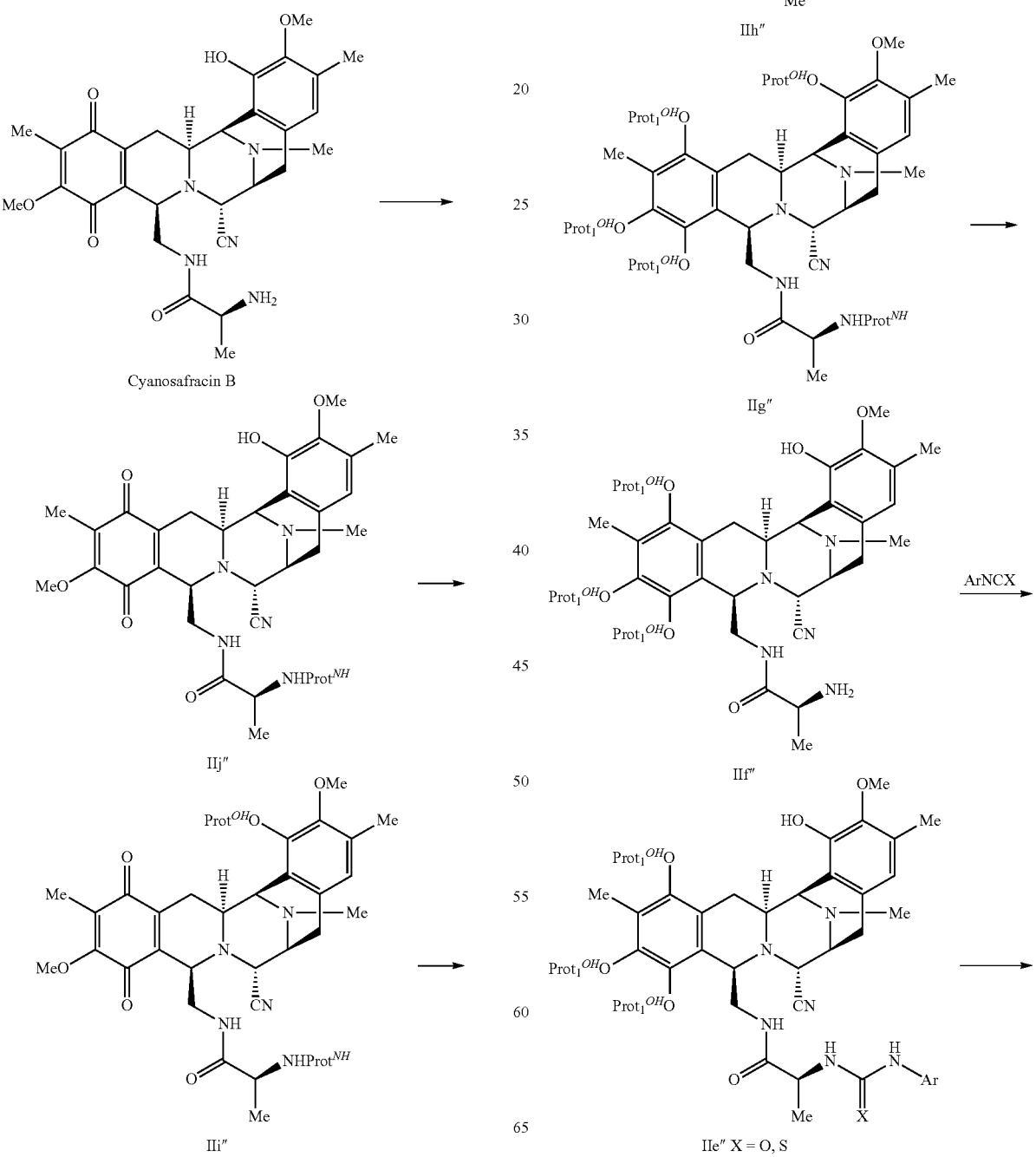

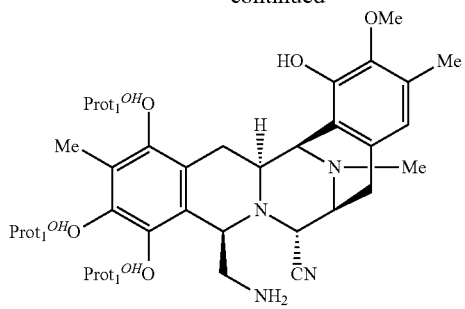

IId″

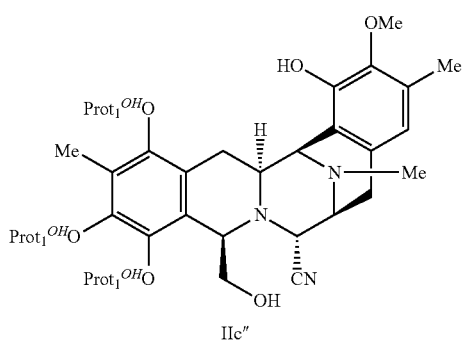

IIc″

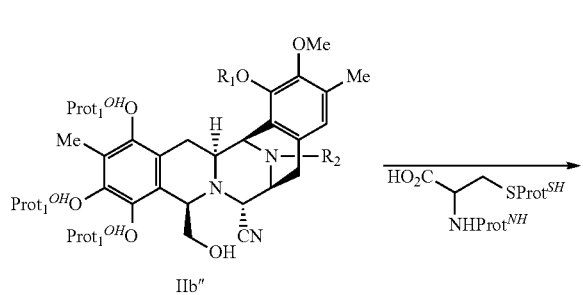

IIb″

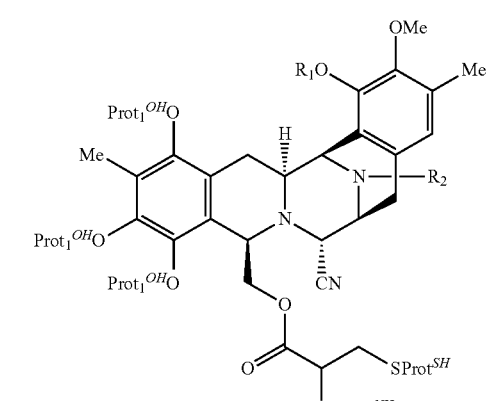

IIa″

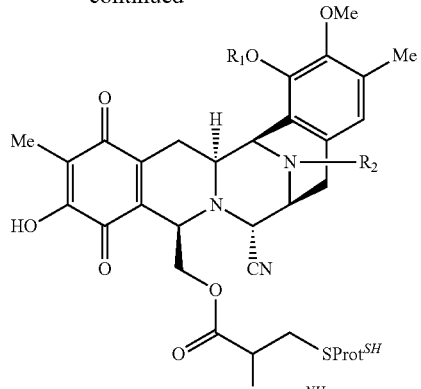

II wherein:
Prot$_1^{OH}$, Prot$^{OH}$ and R$_1$ are protecting groups for OH, with the proviso that Prot$^{OH}$ and R$_1$ are selected to be removed selectively in the presence of Prot$_1^{OH}$ and vice versa.
Ar is a substituted or unsubstituted aryl group;
Prot$^{NH}$ is a protecting group for amino;
Prot$^{SH}$ is a protecting group of SH;
and R$_2$ is as defined above in formula II.

Accordingly, in this embodiment, the process for the synthesis of a compound of formula II comprises the step of deprotecting the Prot$_1^{OH}$O-groups of a compound of formula IIa′ and oxidating the resulting hydroquinone:

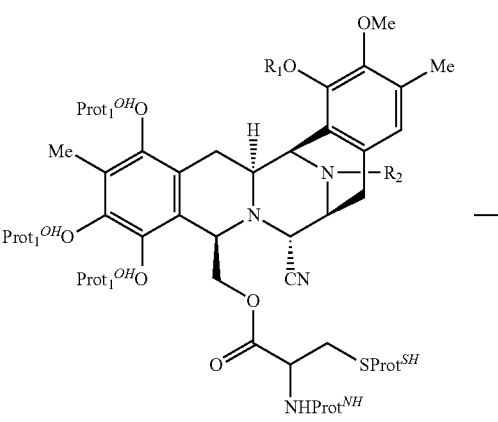

IIa″

→

II wherein
Prot$_1^{OH}$ and R$_1$ are protecting groups for OH, with the proviso that R$_1$ is selected to be removed selectively in the presence of Prot$_1^{OH}$ and vice versa; and
R$_2$, Prot$^{NH}$ and Prot$^{SH}$ are as defined above in the previous disclosure of intermediates of formula II.

Moreover, this process can further comprise the step of preparing the compound of formula IIa" by coupling the primary hydroxyl group in a compound of formula IIb" with a protected cysteine derivative:

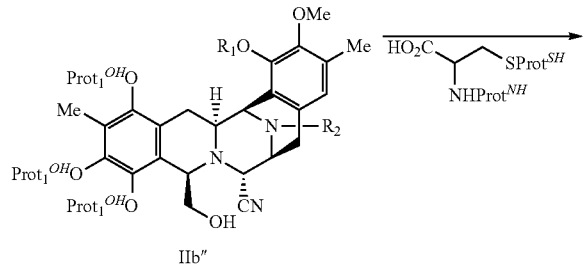

IIb"

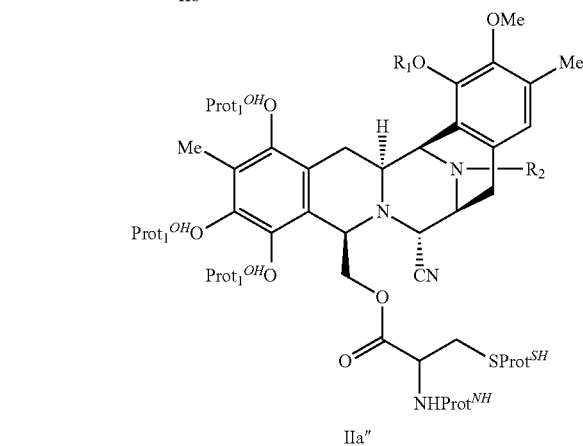

IIa"

wherein
Prot$_1^{OH}$ and R$_1$ are protecting groups for OH, with the proviso that R$_1$ is selected to be removed selectively in the presence of Prot$_1^{OH}$ and vice versa; and
R$_2$, Prot$^{NH}$ and Prot$^{SH}$ are as defined above in the previous disclosure of intermediates of formula II.

Moreover, this process can further comprise the step of preparing the compound of formula IIb" by protecting of the phenol of formula IIc" and, optionally, when R$_2$ in the compound of formula IIb" is not methyl, followed by protecting the primary alcohol with a silyl protecting group for OH, demethylating the NMe group, reacting the resulting secondary amine with a compound of formula R$_2$-LG wherein LG is a leaving group and R$_2$ is as defined in formula II except methyl, and deprotecting the silyl-protected primary alcohol:

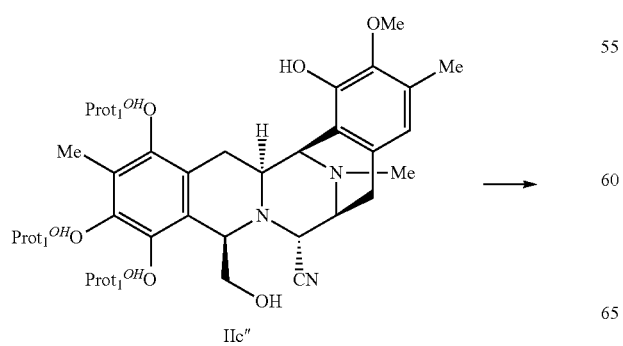

IIc"

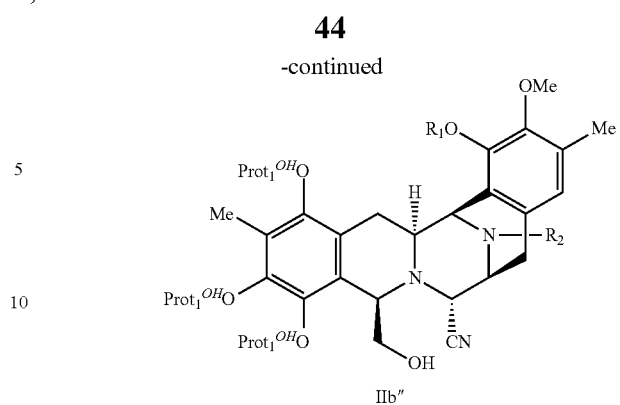

IIb"

wherein
Prot$_1^{OH}$ and R$_1$ are protecting groups for OH, with the proviso that R$_1$ is selected to be removed selectively in the presence of Prot$_1^{OH}$ and vice versa; and
R$_2$ is as defined above in the previous disclosure of intermediates of formula II.

Moreover, this process can further comprise the step of preparing a compound of formula IIc" by converting the primary amine in a compound of formula IId" to a primary alcohol with a suitable oxidizing reagent:

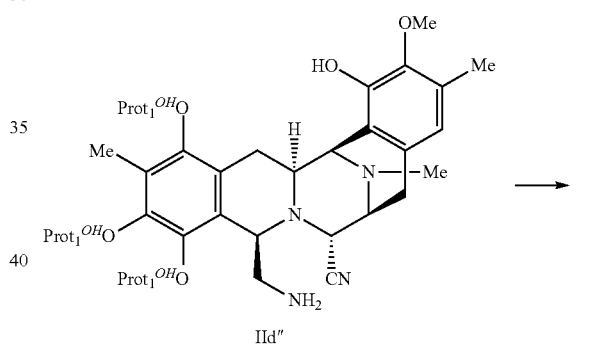

IId"

IIc"

wherein Prot$_1^{OH}$ is a protecting group for OH.

Moreover, this process can further comprise the step of preparing the compound of formula IId" by amidolysis of a compound of formula IIe" to give a primary amine:

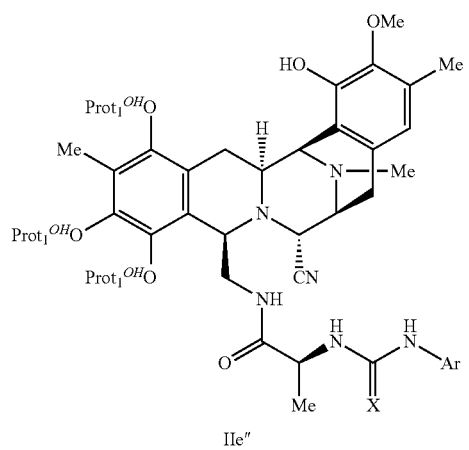

IIe″

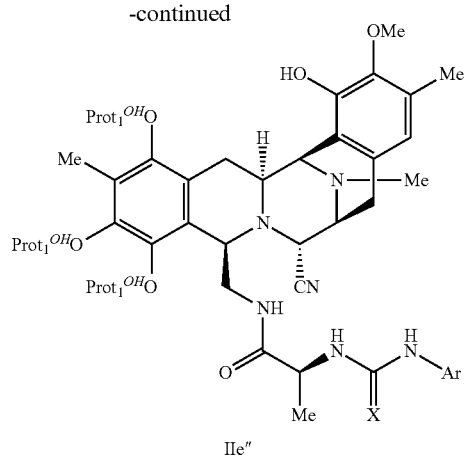

IIe″ wherein $Prot_1^{OH}$ is a protecting group for OH, Ar is a substituted or unsubstituted aryl group, and X is O or S.

Moreover, this process can further comprise the step of partial deprotecting a compound of formula IIg″ to provide a compound of formula IIf″:

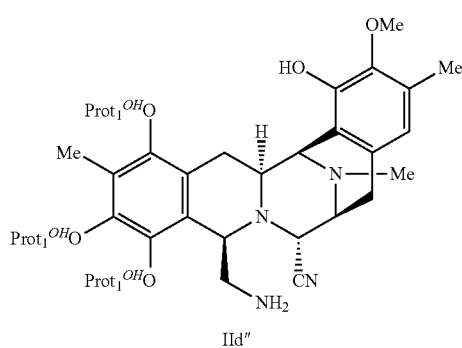

IId″ wherein $Prot_1^{OH}$ is a protecting group for OH, Ar is a substituted or unsubstituted aryl group, and X is O or S.

Moreover, this process can further comprise the step of preparing a compound of formula IIe″ by reaction of a compound of formula IIf″ with a substituted or unsubstituted arylisocyanate or arylisothiocyanate:

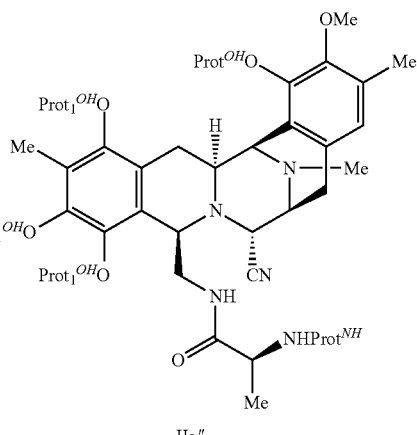

IIg″

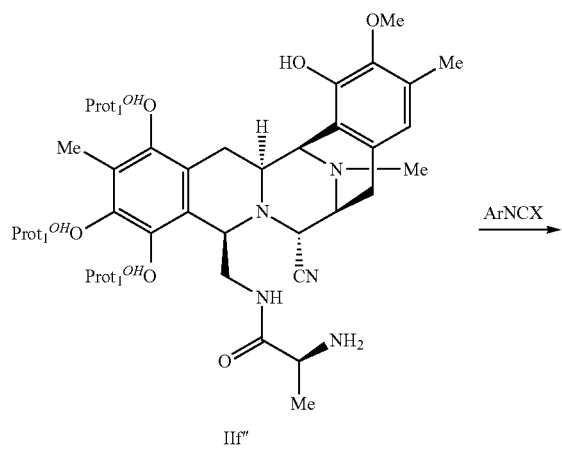

IIf″

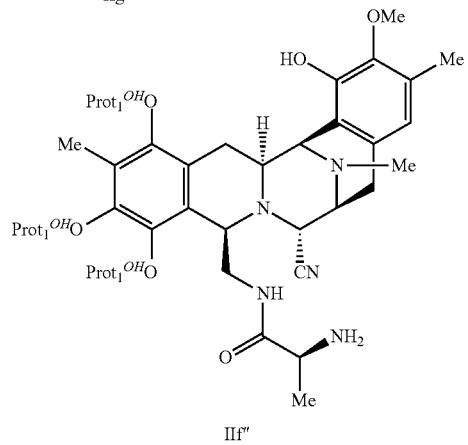

IIf″ wherein $Prot_1^{OH}$ and $Prot^{OH}$ are protecting groups for OH, with the proviso that $Prot^{OH}$ is selected to be removed selectively in the presence of $Prot_1^{OH}$ and vice versa; and $Prot^{NH}$ is a protecting group for amino.

Moreover, this process can further comprise the step of preparing a compound of formula IIg" by reduction of the hydroxyquinone of formula IIh" followed by protection of the hydroxy groups:

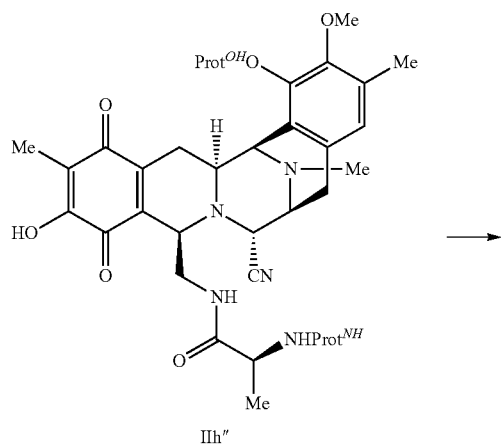

IIh"

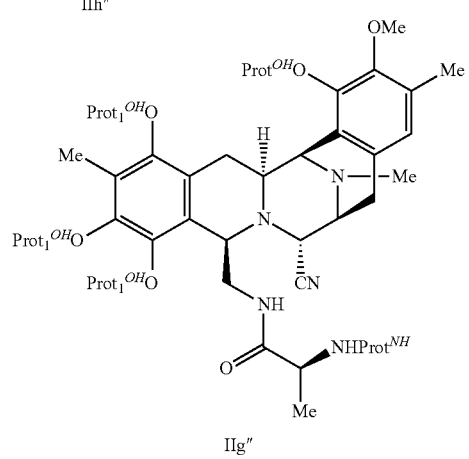

IIg"

wherein
$Prot_1^{OH}$ and $Prot^{OH}$ are protecting groups for OH, with the proviso that $Prot^{OH}$ is selected to be removed selectively in the presence of $Prot_1^{OH}$ and vice versa; and
$Prot^{NH}$ is a protecting group for amino.

Moreover, this process can further comprise the step of hydrolysing or demethylating a methoxyquinone of formula IIi" to provide a compound of formula IIh":

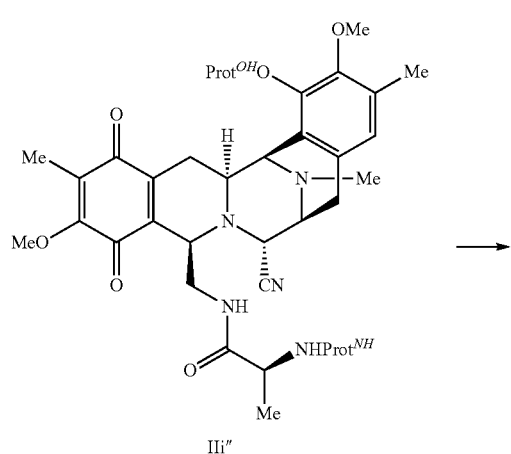

IIi"

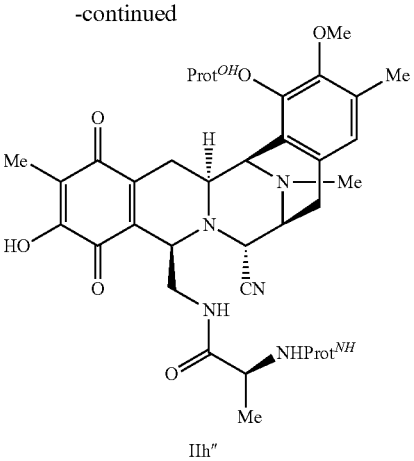

IIh"

wherein $Prot^{OH}$ is a protecting group for OH and $Prot^{NH}$ is a protecting group for amino.

Moreover, this process can further comprise the step of protecting the phenol of formula IIj" to provide a compound of formula IIi":

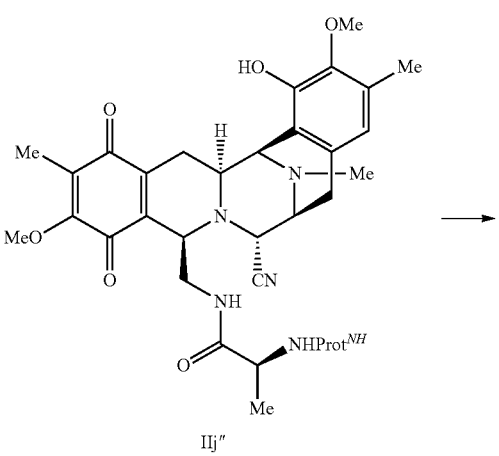

IIj"

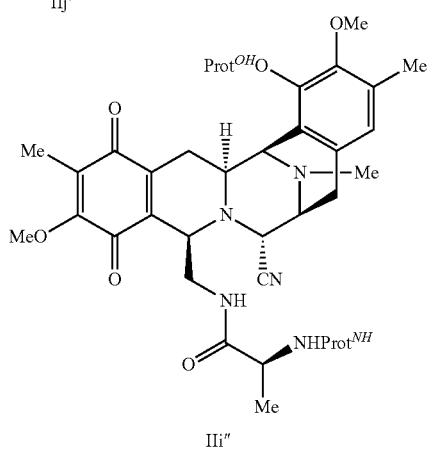

IIi"

wherein $Prot^{OH}$ is a protecting group for OH and $Prot^{NH}$ is a protecting group for amino.

Moreover, this process can further comprise the step of preparing a compound of formula IIj" by protecting the amino group of cyanosafracin B:

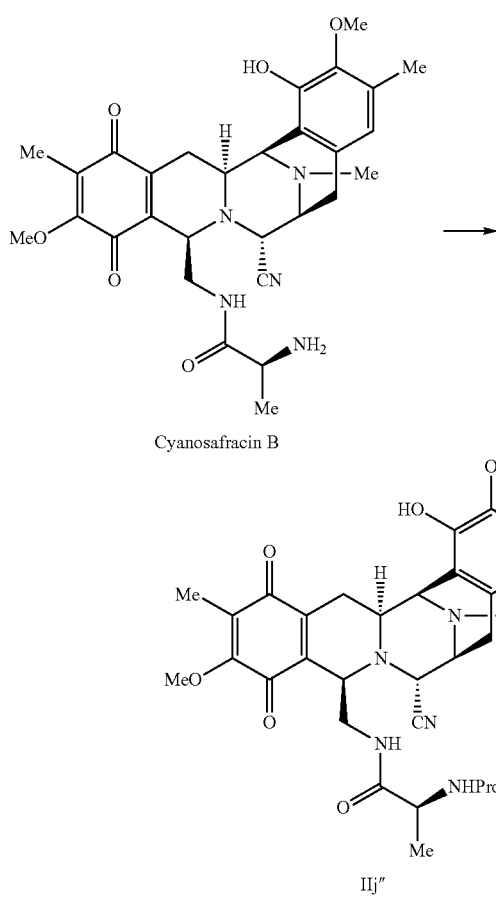

Cyanosafracin B

IIj″ wherein Prot$^{NH}$ is a protecting group for amino.

The deprotection of the compound of formula IIa″ is carried out following standard procedures very well known by a skilled person. The oxidation of the deprotected intermediate is carried out by reaction with a suitable oxidizing reagent. Particularly preferred oxidants are oxygen and Pd-oxygen. The most preferred oxidant is Pd/C-oxygen.

The preparation of a compound of formula IIa″ from a compound of formula IIb″ is typically carried out by reaction with an amino- and sulphur-protected cysteine amino acid wherein the amino acid is activated by a coupling agent such as a carbodiimide, a phosphonium salt, an uronium salt, a guanidinium salt, an imidazolium derived reagent, or a triazolium derived reagent. Particularly preferred coupling agents are carbodiimides. Most preferred coupling agents are 1-ethyl-3-(3-dimethylaminopropyl)-carbodiimide (EDC) and its chlorohydrate (EDC.HCl).

The protection of the phenol of formula IIc″ to give a compound of formula IIb″ is typically carried out by reaction with a suitable reagent for the protection of phenol groups. Preferred reagents for such reaction are alkoxymethyl chlorides, alkoxymethylbromides and alkoxyalkoxymethyl chlorides. Alkoxyalkoxymethyl chlorides are particularly preferred reagents. The most preferred reagent is methoxyethoxymethyl chloride (MEMCl). The optional demethylation during the synthesis of a compound of formula IIb″ typically involves a reaction with a suitable oxidant to provide the corresponding N-oxide. Particularly preferred oxidants for such reaction are peracids. The most preferred oxidant is m-chloroperbenzoic acid.

The conversion of the primary amine of formula IId″ to provide the primary alcohol of formula IIc″ is typically carried out by reaction with a suitable oxidizing reagent such as an inorganic nitrite, nitrogen tetroxide or a nitroferricyanide. More preferred oxidizing reagents are inorganic nitrites. Sodium nitrite is the most preferred oxidizing reagent for this step.

The conversion of the compound of formula IIe″ to a primary amine of formula IId″ is typically carried out by reaction with a suitable amidolysis reagent. Particularly preferred is the use of chlorotrimethylsilane/methanol or iodotrimethylsilane as amidolysis reagents.

The formation of a urea or thiourea of formula IIe″ from a compound of formula IIf″ is typically carried out by reaction with an aryl isocyanate or with an arylisothiocyanate. Particularly preferred reagents for such reaction are arylisothiocyanates. The most preferred reagent is phenylisothiocyanate.

The partial deprotection of the compound of formula IIg″ to provide a compound of formula IIf″ is preferably carried out in a one-pot step using acidic conditions.

The reduction of the hydroxyquinone of formula IIh″ is typically carried out using a transition metal catalysed hydrogenation or a reducing reagent such as $Na_2S_2O_4$. A transition metal catalysed hydrogenation is particularly preferred. The most preferred transition metal catalyst is Pd/C. The hydroxy groups in the intermediate hydroquinone are protected to provide a compound of formula IIg″. Protection of the hydroxy groups is typically carried out by reaction with a suitable reagent for the protection of phenol groups. Particularly preferred protecting groups for this step are allyl and allyloxycarbonyl groups. The most preferred protecting group is allyl.

The conversion of the methoxyquinone of formula IIi″ to give the hydroxyquinone of formula IIh″ is typically carried out by reaction with a suitable reagent for the deprotection of methoxy groups or by reaction with a hydroxide. Preferred reagents for such reaction are a hydroxide or LiI in presence of a base. More preferably the reaction is carried out with an alkaline hydroxide. The most preferred alkaline hydroxide is LiOH.

The protection of the phenol of formula IIj″ to give a compound of formula IIi″ is typically carried out by reaction with a suitable reagent for the protection of phenol groups. Preferred reagents for such reaction are alkoxymethyl chlorides, alkoxymethylbromides and alkoxyalkoxymethyl chlorides. Alkoxyalkoxymethyl chlorides are particularly preferred reagents. The most preferred reagent is methoxyethoxymethyl chloride (MEMCl).

The protection of Cyanosafracin B to give a compound of formula IIj″ is typically carried out by reaction with a suitable reagent for the protection of amino groups. Preferred reagents for such reaction are dicarbonates and alkoxycarbonylchlorides. Dicarbonates are particularly preferred reagents. The most preferred reagent is di-tert-butyl dicarbonate ($Boc_2O$).

In this process, particularly preferred Prot$^{OH}$ groups are those that together with the O atom to which they are attached form an ether group. More preferably Prot$^{OH}$ groups are methoxyethoxymethyl and methoxymethyl. The most preferred Prot$^{OH}$ group is methoxyethoxymethyl. Particularly preferred Prot$_1^{OH}$ groups are those that together with the O atom to which they are attached form an ether or a carbonate groups. More preferably Prot$_1^{OH}$ groups are allyl and allyloxycarbonyl. The most preferred Prot$_1^{OH}$ group is allyl.

In this process, the most preferred Ar group is phenyl.

In this process, the use of carbamate protected NH groups is particularly preferred. More preferably carbamate protected amino groups are selected from allylcarbamate, 2,2,2-trichloroethylcarbamate, benzylcarbamate, 9-fluorenylmethyl-carbamate, and t-butylcarbamate. The most preferred carbamate protected amino group is t-butylcarbamate.

In this process, the use of thioether protected SH groups is particularly preferred. More preferably thioether protected SH groups are substituted or unsubstituted S-9-fluorenylmethyl thioethers. The most preferred thioether protected SH group is S-9-fluorenylmethyl (Fm) thioether.

Examples of suitable starting materials for the synthesis of compounds of formula II include:

(a) Saframycin A, saframycin H, saframycin S, saframycin $Y_3$, saframycin $Y_{d1}$, saframycin $A_{d1}$, saframycin $Y_{d2}$, saframycin $AH_2$, saframycin $AH_2Ac$, saframycin $AH_1$, and saframycin $AH_1Ac$ of formula:

| Compound | $R_3$ | $R_{15a}$ | $R_{15b}$ | $R_{15c}$ |
|---|---|---|---|---|
| Saframycin A | CN | O | | Me |
| Saframycin H | CN | OH | $CH_2COMe$ | Me |
| Saframycin S | OH | O | | Me |
| Saframycin $Y_3$ | CN | $NH_2$ | H | Me |
| Saframycin $Y_{d1}$ | CN | $NH_2$ | H | $C_2H_5$ |
| Saframycin $A_{d1}$ | CN | O | | $C_2H_5$ |
| Saframycin $Y_{d2}$ | CN | $NH_2$ | H | H |
| Saframycin $AH_2$ | CN | $H^a$ | $OH^a$ | Me |
| Saframycin $AH_2Ac$ | CN | H | OAc | Me |
| Saframycin $AH_1$, | CN | $OH^a$ | $H^a$ | Me |
| Saframycin $AH_1Ac$ | CN | OAc | H | Me |

$^a$Assignments are interchangeable.

(b) Safracin B and cyanosafracin B of formula:

| Compound | $R_3$ | $R_{15a}$ | $R_{15b}$ | $R_{15c}$ |
|---|---|---|---|---|
| Safracin B | OH | $NH_2$ | H | Me |
| Cyanosafracin B | CN | $NH_2$ | H | Me |

(c) Jorumycin, cyanojorumycin, renieramycin E, jorunnamycin A, and jorunnamycin C of formula:

| Compound | $R_3$ | R |
|---|---|---|
| Jorumycin | OH | COMe |
| Cyanojorumycin | CN | COMe |
| Renieramycin E | OH | CO—C(CH$_3$)=CH—CH$_3$ |
| Jorunnamycin A | CN | H |
| Jorunnamycin C | CN | $COCH_2CH_3$ | that are disclosed in Charupant, K. et. al. Bioorganic Medicinal Chemistry, 2009, 17, 4548-4558.

d) Renieramycin T (described in Daikuhara, N. et. al. Tetrahedron Letters, 2009, 50, 4276-4278)

and e) Saframycin R

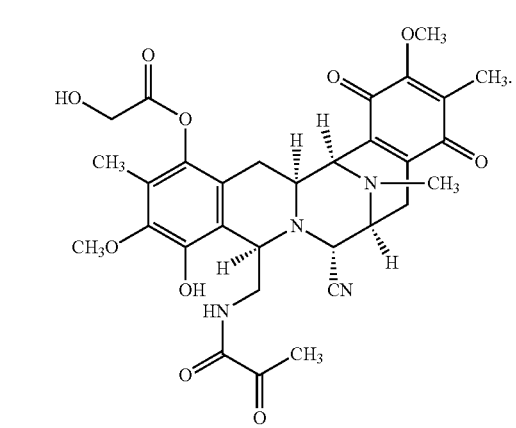

The most preferred starting material for the synthesis of compounds of formula II is cyanosafracin B of formula:

Cyanosafracin B

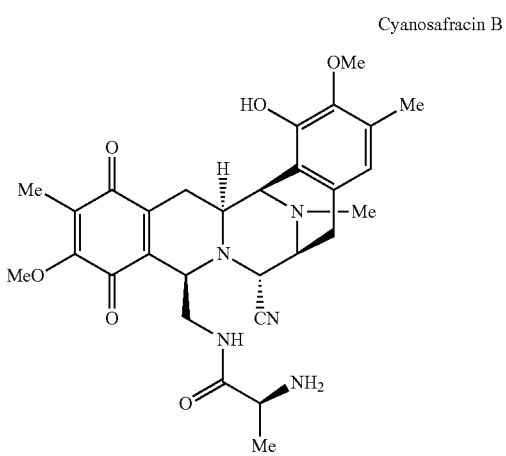 [SMILES: COC1=C(C)C(=O)C2=C(C1=O)[C@H](CNC(=O)[C@H](C)N)N1[C@@H](C#N)[C@@H]3Cc4cc(C)c(OC)c(O)c4[C@H]([C@@H]1C2)N3C]

This invention also relates to the use of intermediates of formula II in the manufacture of compounds of formula I, and in particular in the manufacture of:

ET-743

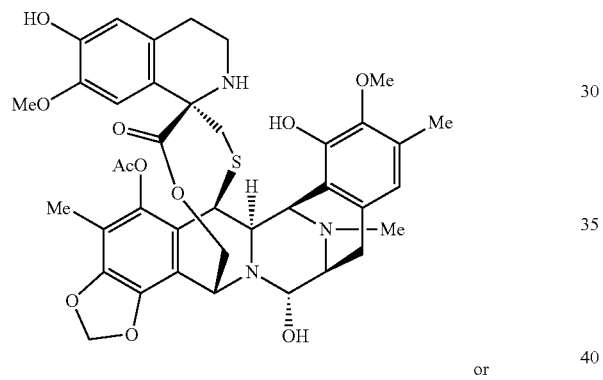

or

-continued

In additional preferred embodiments, the preferences described above for the different groups and substituents are combined. The present invention is also directed to such combinations of preferred groups and substitutions in the formulae above.

EXAMPLES

Example 1

Synthesis of Intermediate 10

Route A

Scheme VII provides an example of the synthesis of intermediate 10 (a compound of formula II).

Scheme VII

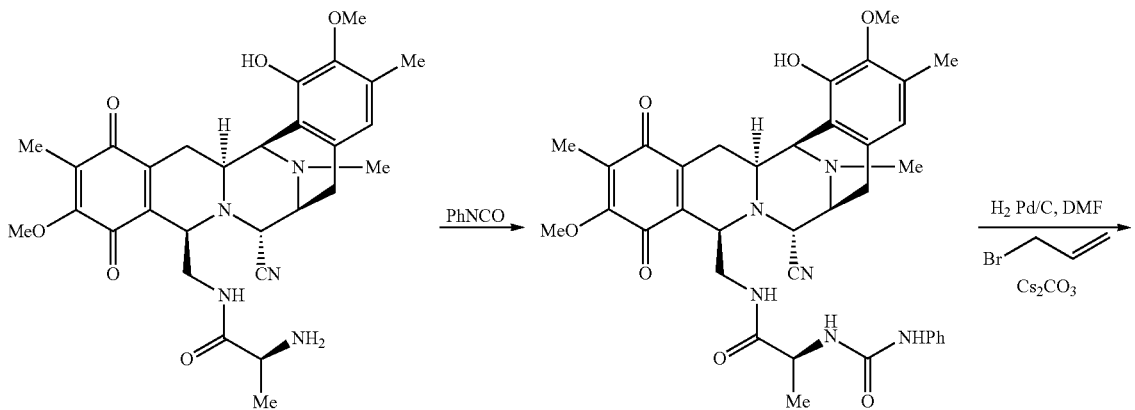

-continued
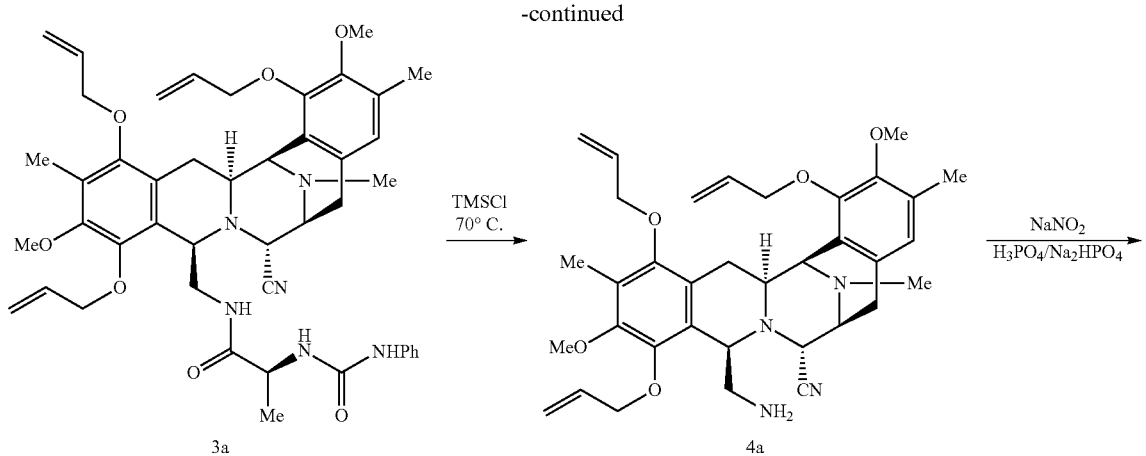
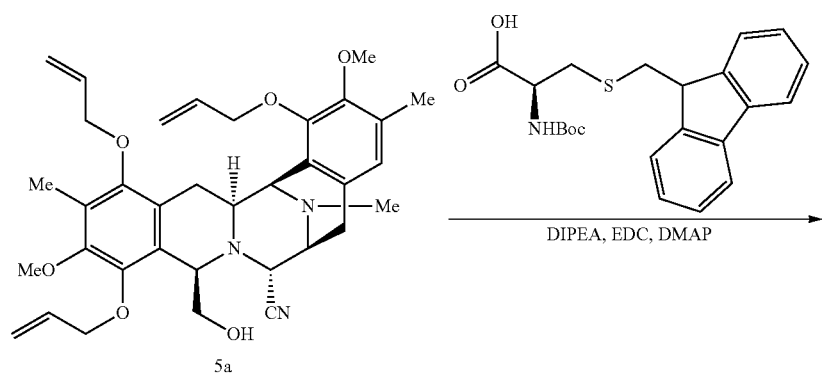
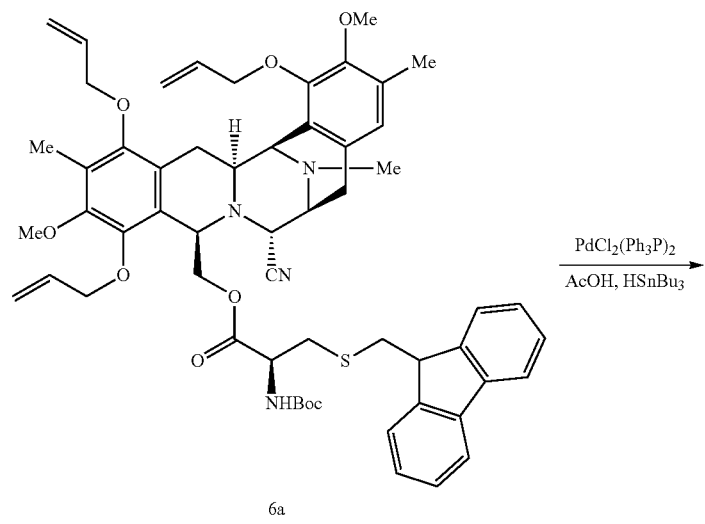

-continued
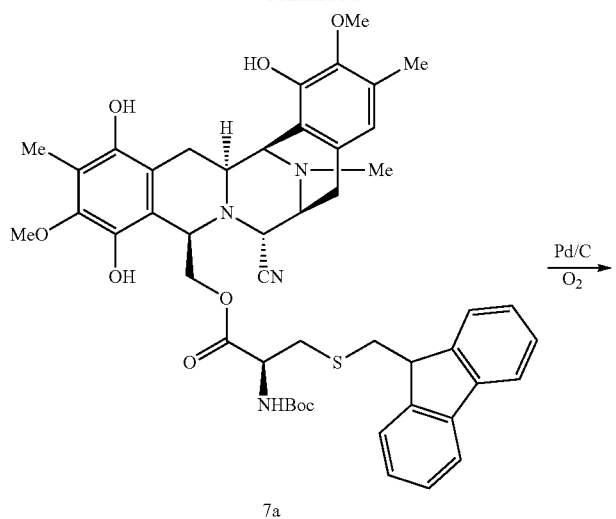
7a
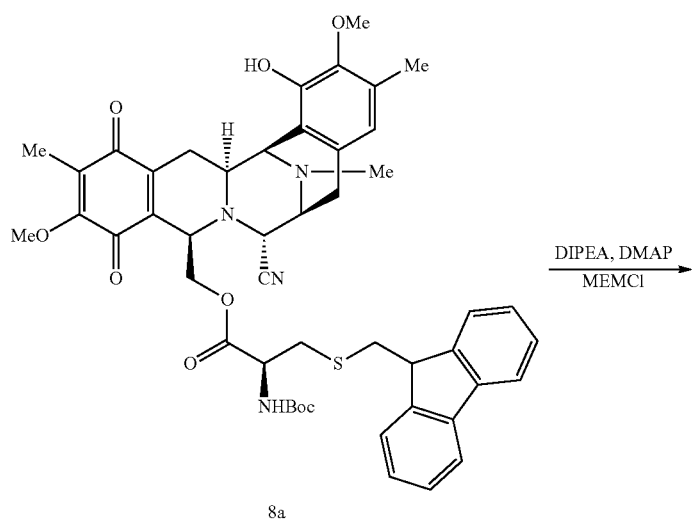
8a
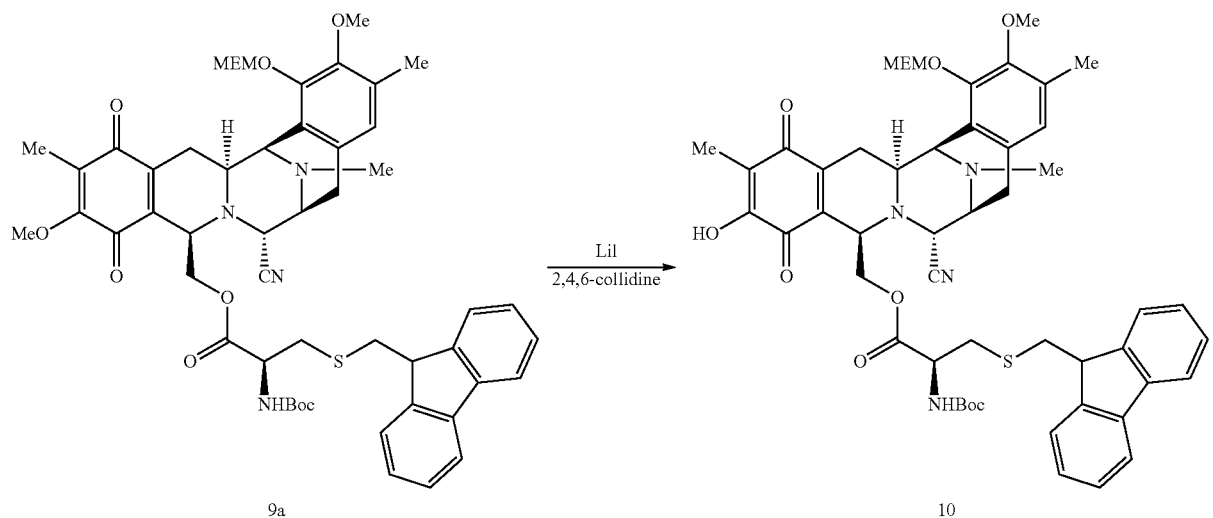
9a                                                10

Synthesis of Intermediate 2a

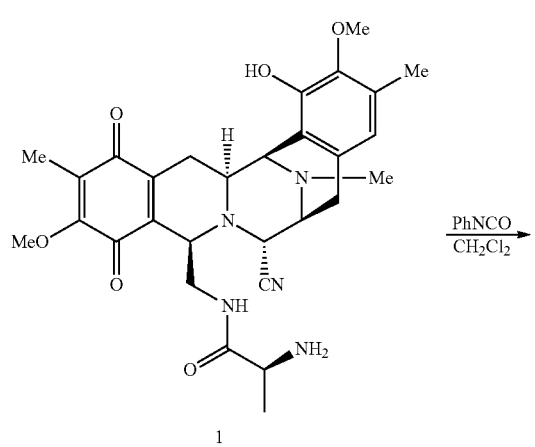

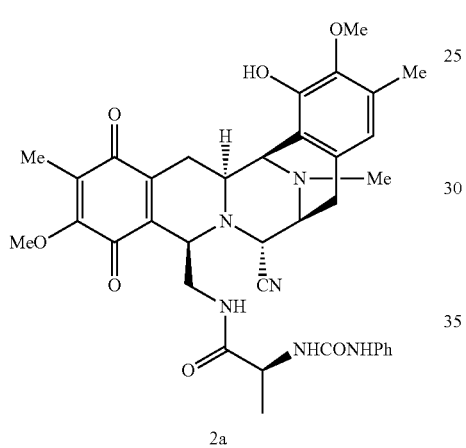

A mixture of cyanosafracin B (1) (3.06 g, 5.6 mmol) and phenyl isocyanate (0.6 mL, 5.6 mmol) in $CH_2Cl_2$ (29 mL, 5.2 mL/mmol) was stirred for 4 h at 23° C. The reaction mixture was concentrated under vacuum and the crude was purified by column flash chromatography over $SiO_2$ eluted with Hexane:EtOAc (from 60:40 to 20:80) to give pure 2a (3.7 g, 100% yield).

$^1$H-NMR (CDCl$_3$, 300 MHz): δ 7.23-6.95 (m, 6H), 6.47 (s, 1H), 6.37 (s, 1H), 5.51 (d, 1H, J=7.7 Hz), 5.40 (m, 1H), 4.18 (s, 1H), 4.02 (m, 1H), 3.86 (s, 3H), 3.76 (m, 1H), 3.71 (s, 3H), 3.35-3.02 (m, 6H), 2.48-2.41 (d, 1H, J=18.0 Hz), 2.35 (s, 3H), 2.24 (s, 3H), 1.95-1.85 (m, 1H), 1.00 (d, 3H, J=6.0 Hz).

$^{13}$C-NMR (CDCl$_3$, 75 MHz): δ 185.6, 181.1, 173.9, 155.6, 154.7, 147.4, 143.6, 142.4, 138.6, 135.0, 130.5, 129.5, 129.0, 128.6, 123.0, 120.2, 119.7, 117.5, 117.0, 60.8, 60.5, 59.0, 56.0, 55.7, 55.1, 54.8, 49.4, 41.7, 41.4, 25.5, 24.2, 18.6, 15.7, 8.6.

MS (ES): m/z 669.2 [M+1]$^+$.

Synthesis of Intermediate 3a

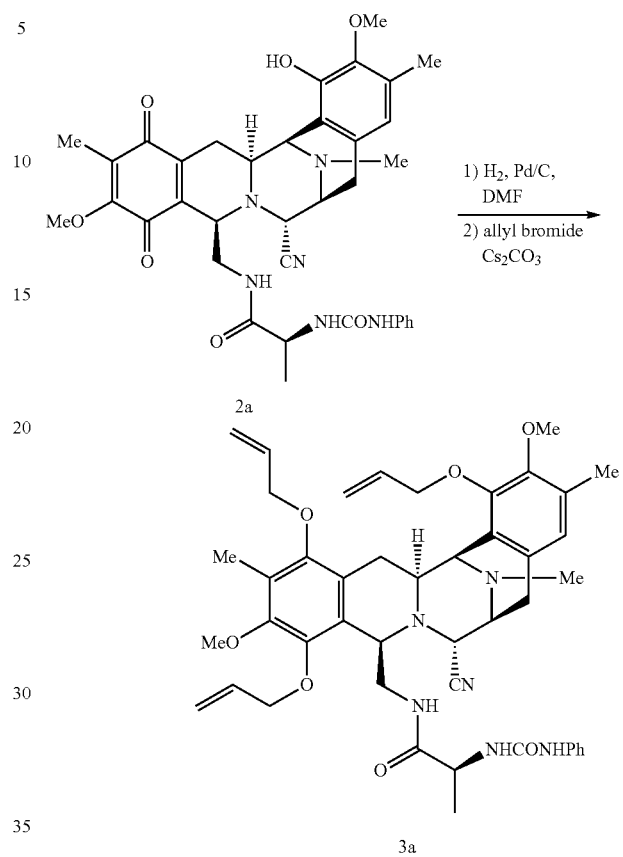

A suspension of 2a (450 mg, 0.67 mmol) and Pd on carbon (90 mg, 10%) in anhydrous DMF (10 mL, 15 mL/mmol) was degasified under vacuum and stirred under an hydrogen atmosphere for 2 h at 23° C. The reaction mixture was filtered through a 0.45 μm PTFE filter over anhydrous $Cs_2CO_3$ (1.3 g, 4.0 mmol), washed with DMF (5 mL), and allyl bromide (1.7 mL, 20 mmol) was added at 23° C. The reaction mixture was stirred for 4 h at 23° C. and filtered through Celite®. An aqueous saturated solution of NaCl was added to the filtered solution which was extracted with $CH_2Cl_2$. The combined organic layers were dried over $Na_2SO_4$, filtered, and concentrated under vacuum. The crude was purified by column flash chromatography over $SiO_2$ eluted with $CH_2Cl_2$:EtOAc (40:60) to afford pure 3a (296 mg, 56% yield).

$^1$H-NMR (CDCl$_3$, 300 MHz): δ 7.31-6.87 (m, 5H), 6.62 (s, 1H), 6.24 (d, 1H, J=7.8 Hz), 6.13-6.00 (m, 3H), 5.86 (m, 1H), 5.43 (s, 1H), 5.37 (s, 2H), 5.31-5.19 (m, 4H), 4.73 (dd, 1H, J=12.3 and 5.7 Hz), 4.50 (m, 1H), 4.27 (m, 2H), 4.11 (m, 3H), 3.92 (m, 1H), 3.79 (s, 3H), 3.76 (m, 1H), 3.61 (s, 3H), 3.50 (m, 1H), 3.20 (m, 2H), 3.0 (dd, 2H, J=18.0 and 8.4 Hz), 2.45 (d, 1H, J=18.0 Hz), 2.28 (s, 3H), 2.18 (s, 3H), 2.12 (s, 3H), 1.86 (m, 1H), 1.03 (d, 3H, J=9 Hz).

$^{13}$C-NMR (CDCl$_3$, 75 MHz): δ 173.8, 154.5, 150.5, 150.4, 149.7, 149.1, 144.2, 139.0, 134.1, 133.8, 130.9, 129.6, 128.6, 125.0, 124.9, 124.5, 123.7, 122.2, 119.1, 118.0, 117.8, 117.7, 117.6, 74.0, 73.8, 73.3, 60.2, 60.0, 56.7, 56.4, 55.1, 49.3, 43.6, 41.6, 26.3, 25.5, 19.2, 15.8, 9.6, 6 carbon signals overlap.

MS (ES): m/z 791.3 [M+1]$^+$.

Synthesis of Intermediate 4a

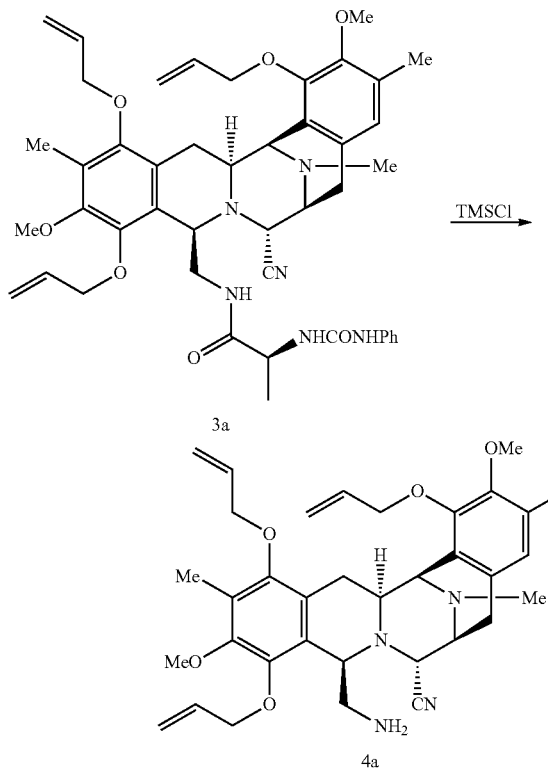

A solution of 3a (90 mg, 0.13 mmol) and TMSCl (0.2 mL, 1.6 mmol) in MeOH (2.45 mL, 18.8 mL/mmol) was stirred for 6 h at 70° C. The reaction mixture was cooled to 23° C. and concentrated under vacuum. The crude obtained was diluted with EtOAc and acidified with HCl 1M until acid pH. The aqueous layer was washed with EtOAc (3×), basified with $K_2CO_3$ until basic pH, and extracted with $CH_2Cl_2$. The combined organic layers were dried over $Na_2SO_4$, filtered, and concentrated under vacuum to give crude 4a (61 mg, 76% yield) which was used in the next step without further purification.

$^1$H-NMR (CDCl$_3$, 300 MHz): δ 6.69 (s, 1H), 6.13-6.04 (m, 3H), 5.44-5.20 (m, 3H), 4.71 (dd, 1H, J=12.3 and 5.4 Hz), 4.59-4.41 (m, 2H), 4.33-4.01 (m, 8H), 3.76 (s, 6H), 3.34-3.05 (m, 4H), 2.72-2.50 (m, 3H), 2.34 (s, 3H), 2.21 (s, 3H), 2.16 (s, 3H), 1.76 (dd, 1H, J=15.6 and 12.0 Hz).

$^{13}$C-NMR (CDCl$_3$, 75 MHz): δ 150.1, 149.9, 149.5, 149.0, 144.4, 134.2, 134.2, 133.8, 130.8, 129.9, 129.1, 128.2, 125.8, 125.2, 124.7, 124.2, 123.8, 118.0, 74.0, 73.7, 73.5, 60.7, 60.2, 59.9, 58.9, 57.2, 56.6, 55.4, 46.5, 41.7, 29.7, 26.5, 25.8, 15.8, 9.6.

MS (ES): m/z 601.3 [M+1]$^+$, 623.2 [M+23]$^+$.

Synthesis of Intermediate 5a

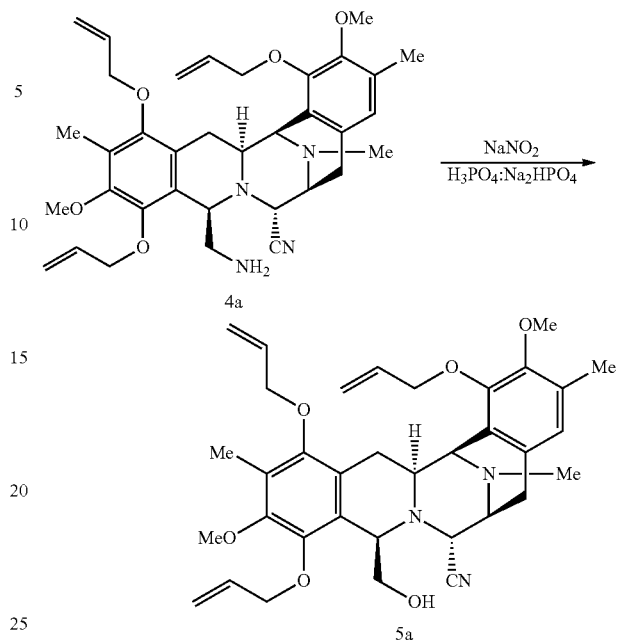

To a mixture of 4a (6.89 g, 11.5 mmol) and $H_3PO_4$:$Na_2HPO_4$ aqueous solution (35 mL, 0.018 g $H_3PO_4$:0.186 g $Na_2HPO_4$ per mL of $H_2O$) in $CH_2Cl_2$ (69 mL, 6 mL/mmol), an aqueous solution of NaNO$_2$ (7.9 mL, 23.0 mmol, 20%) was portion wise added over 1 h at 23° C. The reaction mixture was stirred overnight at 23° C., diluted with $H_2O$, and extracted with $CH_2Cl_2$. The combined organic layers were dried over $Na_2SO_4$, filtered, and concentrated under vacuum. The crude was purified by column flash chromatography over SiO$_2$ eluted with $CH_2Cl_2$:EtOAc (40:60) to afford pure 5a (4.62 g, 67% yield).

$^1$H-NMR (CDCl$_3$, 300 MHz): δ 6.72 (s, 1H), 6.16-6.05 (m, 3H), 5.44-5.2 (m, 6H), 4.71 (dd, 1H, J=12.3 and 5.4 Hz), 4.60-4.44 (m, 2H), 4.34-4.04 (m, 6H), 3.76 (s, 3H), 3.75 (s, 3H), 3.60-3.56 (m, 1H), 3.35 (d, 1H, J=7.5 Hz), 3.28-3.22 (m, 3H), 3.13 (dd, 1H, J=18.0 and 7.5 Hz), 2.52 (d, 1H, J=18.0 Hz), 2.37 (s, 3H), 2.21 (s, 3H), 2.16 (s, 3H), 1.90 (dd, 1H, J=8.5 and 4.0 Hz), 1.76 (dd, 1H, J=16.0 and 12.5 Hz).

$^{13}$C-NMR (CDCl$_3$, 75 MHz): δ 150.1, 149.7, 149.6, 149.2, 144.5, 134.1, 133.8, 130.9, 129.5, 125.6, 124.8, 124.6, 124.2, 123.7, 117.8, 117.6, 117.5, 73.9, 73.7, 73.5, 65.7, 60.8, 60.1, 59.8, 58.6, 57.2, 56.7, 55.4, 41.7, 26.2, 25.8, 15.7, 9.5, two carbon signals overlap.

MS (ES): m/z 602.3 [M+1]$^+$, 624.2 [M+23]$^+$.

Synthesis of Intermediate 6a

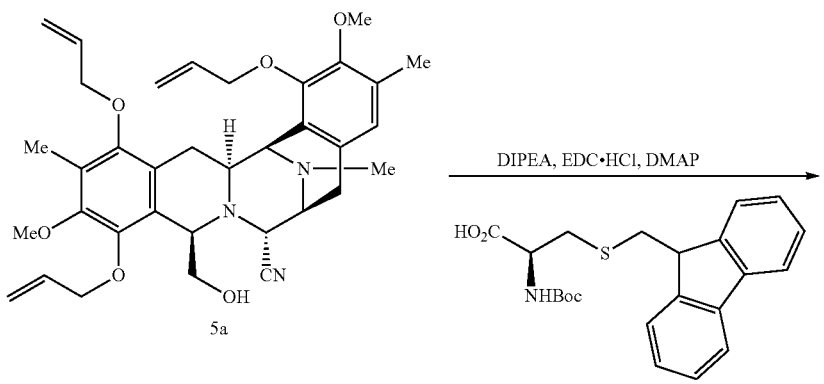

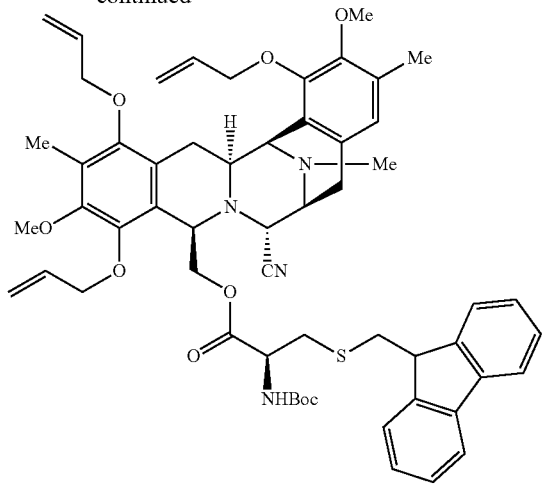

6a

To a solution of 5a (4.65 g, 7.7 mmol) and Boc-L-Cys (Fm)-OH (6.1 g, 15.4 mmol) in $CH_2Cl_2$ (264 mL, 34 mL/mmol), DIPEA (2.67 mL, 15.4 mmol), EDC.HCl (4.41 g, 23.0 mmol) and DMAP (0.938 g, 7.7 mmol) were added at 23° C. The reaction mixture was stirred for 1.5 h at 23° C., diluted with $CH_2Cl_2$, and washed with an aqueous saturated solution of $NaHCO_3$. The combined organic layers were dried over $Na_2SO_4$, filtered, and concentrated under vacuum. The crude was purified by column flash chromatography over $SiO_2$ eluted with Hexane:EtOAc (from 90:10 to 80:20) to afford pure 6a (7.12 g, 94% yield).

$^1$H-NMR (CDCl$_3$, 300 MHz): δ 7.75-7.28 (m, 8H), 6.60 (s, 1H), 6.13-5.99 (m, 3H), 5.42-5.16 (m, 7H), 4.73-4.67 (m, 1H), 4.56-4.51 (m, 1H), 4.43-3.80 (m, 10H), 3.76 (s, 3H), 3.73 (s, 3H), 3.28-2.81 (m, 7H), 2.61-2.48 (m, 2H), 2.28 (s, 3H), 2.19 (s, 3H), 2.13 (s, 3H), 1.77-1.68 (m, 1H), 1.45 (s, 9H).

$^{13}$C-NMR (CDCl$_3$, 75 MHz): δ 170.9, 155.2, 150.5, 150.0, 149.7, 148.9, 146.0, 144.9, 141.2, 134.5, 134.2, 133.9, 130.7, 130.6, 127.8, 127.2, 125.5, 125.0, 124.8, 124.4, 123.8, 120.1, 118.4, 118.2, 117.9, 117.7, 80.34, 74.3, 74.1, 73.6, 69.0, 61.6, 60.4, 60.2, 57.4, 57.2, 56.5, 55.7, 53.6, 47.0, 41.9, 37.3, 35.6, 29.9, 28.6, 26.6, 25.8, 15.9, 9.8.

MS (ES): m/z 983.3 [M+1]$^+$.

Synthesis of Intermediate 7a

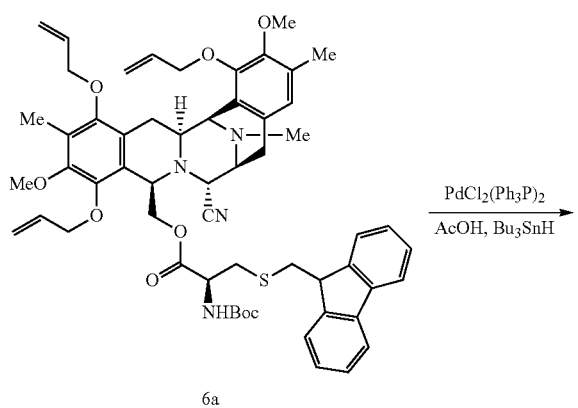

6a

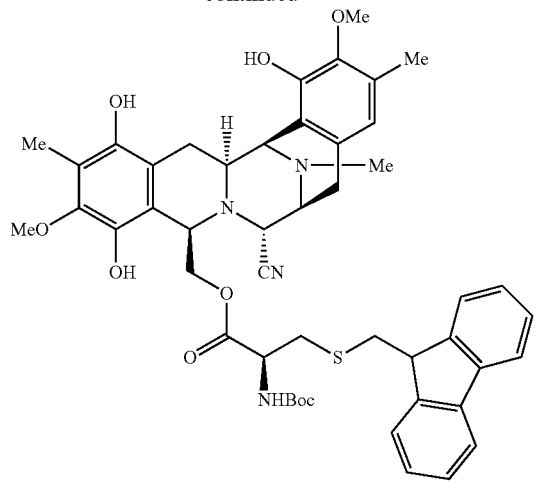

7a

To a suspension of 6a (7.12 g, 7.2 mmol) and PdCl$_2$(Ph$_3$P)$_2$ (814 mg, 1.16 mmol) in $CH_2Cl_2$ (132 mL, 18 mL/mmol), AcOH (4.14 mL, 72.4 mmol) and Bu$_3$SnH (11.68 mL, 43.4 mmol) were added at 23° C. The reaction mixture was stirred for 1 h at 23° C., loaded into a column flash chromatography over $SiO_2$ and eluted with Hexane:EtOAc (from 80:20 to 60:40) to afford pure 7a (6.28 g, 100% yield).

$^1$H-NMR (CD$_3$OD, 300 MHz): δ 7.76-7.56 (m, 4H), 7.37-7.23 (m, 4H), 6.44-6.34 (m, 1H), 4.28-4.01 (m, 6H), 3.85-3.80 (m, 1H), 3.68 (s, 3H), 3.62 (s, 3H), 3.25 (m, 1H), 3.07-2.86 (m, 5H), 2.71-2.54 (m, 2H), 2.41-2.34 (m, 1H), 2.21 (s, 3H), 2.17 (s, 3H), 2.08 (s, 3H), 1.84 (m, 1H), 1.41 (s, 9H).

$^{13}$C-NMR (CD$_3$OD, 75 MHz): δ 171.1, 147.6, 146.2, 144.3, 143.9, 143.6, 141.2, 139.9, 131.2, 129.3, 127.4, 126.9, 124.9, 124.8, 120.9, 120.2, 119.6, 118.3, 117.6, 79.6, 67.3, 61.1, 59.7, 57.8, 56.9, 56.6, 55.7, 53.8, 40.6, 36.5, 34.5, 27.5, 25.9, 25.5, 14.9, 8.6, twelve carbon signals overlap.

MS (ES): m/z 863.0 [M+1]$^+$.

Synthesis of Intermediate 8a

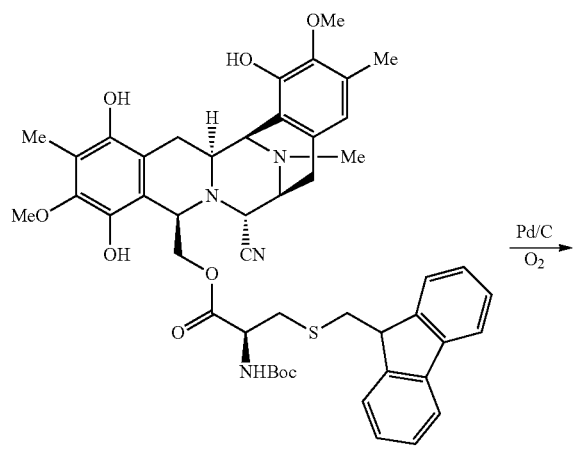

7a

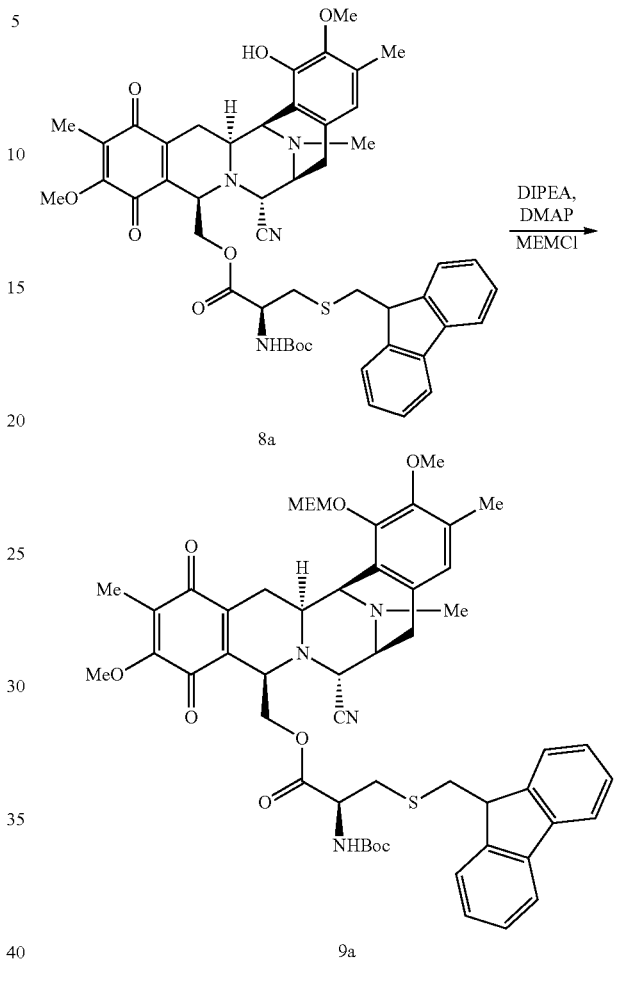

8a

9a

A suspension of 7a (1.7 g, 2.0 mmol) and Pd on carbon (855 mg, 10%) in MeOH (50 mL, 25.5 mL/mmol) was stirred for 24 h under an air atmosphere at 23° C. The reaction mixture was filtered through Celite®, washed with $CH_2Cl_2$, and concentrated. The crude was purified by column flash chromatography over $SiO_2$ eluted with Hexane:EtOAc (from 70:30 to 60:40) to afford pure 8a (1.41 g, 82% yield).

$^1$H-NMR (CDCl$_3$, 300 MHz): δ 7.74-7.58 (m, 4H), 7.4-7.25 (m, 4H), 6.37 (s, 1H), 5.81 (s, 1H), 4.90 (d, 1H, J=8.4 Hz), 4.57 (m, 1H), 4.13-4.01 (m, 5H), 3.95 (s, 3H), 3.70 (s, 3H), 3.31 (d, 1H, J=8.1 Hz), 3.15-2.88 (m, 5H), 2.53 (d, 1H, J=18.6 Hz), 2.39 (m, 1H), 2.26 (s, 3H), 2.21 (s, 3H), 1.85 (s, 3H), 1.69 (m, 1H), 1.38 (s, 9H).

$^{13}$C-NMR (CDCl$_3$, 75 MHz): δ 185.6, 181.2, 170.4, 155.5, 154.8, 146.8, 145.8, 142.9, 142.8, 140.9, 140.8, 134.8, 131.1, 130.9, 129.1, 128.6, 127.5, 126.9, 124.9, 124.8, 120.7, 119.8, 117.4, 116.1, 79.8, 63.1, 61.0, 60.8, 59.1, 56.4, 55.8, 55.4, 55.1, 52.7, 46.9, 46.6, 41.7, 41.6, 36.9, 36.6, 34.7, 34.4, 29.6, 28.2, 24.7, 15.8, 8.7.

MS (ES): m/z 861.2 [M+1]$^+$.

Synthesis of Intermediate 9a

To a solution of 8a (4.5 g, 5.2 mmol) in $CH_3CN$ (166 mL, 32 mL/mmol), DIPEA (18.2 mL, 104 mmol), MEMCl (8.86 mL, 78 mmol) and catalytic DMAP were added at 23° C. The reaction mixture was stirred for 5 h at 23° C., diluted with $CH_2Cl_2$, and washed with HCl 1M and an aqueous saturated solution of $NaHCO_3$. The combined organic layers were dried over $Na_2SO_4$, filtered, and concentrated under vacuum. The crude was purified by column flash chromatography over $SiO_2$ eluted with $CH_2Cl_2$:EtOAc (from 90:10 to 70:30) to afford pure 9a (2.51 g, 51% yield).

$^1$H-NMR (CDCl$_3$, 300 MHz): δ 7.73-7.58 (m, 4H), 7.40-7.29 (m, 4H), 6.56 (s, 1H), 5.28-5.14 (m, 2H), 4.94 (m, 1H), 4.48 (m, 1H), 4.20 (bs, 1H), 4.09-3.94 (m, 5H), 3.94 (s, 3H), 3.80 (m, 1H), 3.68 (s, 3H), 3.58 (t, 2H, J=4.8 Hz), 3.38 (s, 3H), 3.31 (m, 1H), 3.14-2.87 (m, 6H), 2.53 (d, 1H, J=18.6 Hz), 2.40 (m, 1H), 2.28 (s, 3H), 2.16 (s, 3H), 1.83 (s, 3H), 1.56 (m, 1H), 1.38 (s, 9H).

$^{13}$C-NMR (CDCl$_3$, 75 MHz): δ 185.5, 181.1, 170.4, 155.5, 154.7, 148.7, 148.2, 145.7, 142.9, 140.9, 140.8, 134.7, 130.9, 130.3, 128.5, 127.5, 127.0, 124.8, 124.7, 123.1, 119.8, 117.4, 98.1, 79.9, 71.6, 69.3, 63.3, 61.0, 60.0, 59.2, 58.9, 56.3, 56.1, 55.2, 55.0, 52.8, 46.6, 46.4, 41.4, 37.3, 36.6, 34.6, 28.2, 24.8, 24.6, 15.7, 8.6.

MS (ES): m/z 949.2 [M+1]$^+$.

Synthesis of Intermediate 10

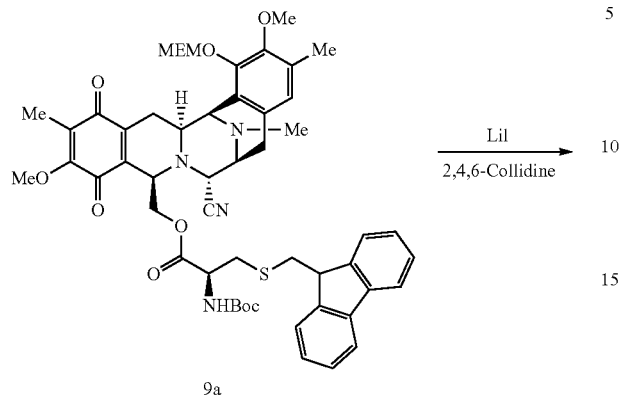

9a

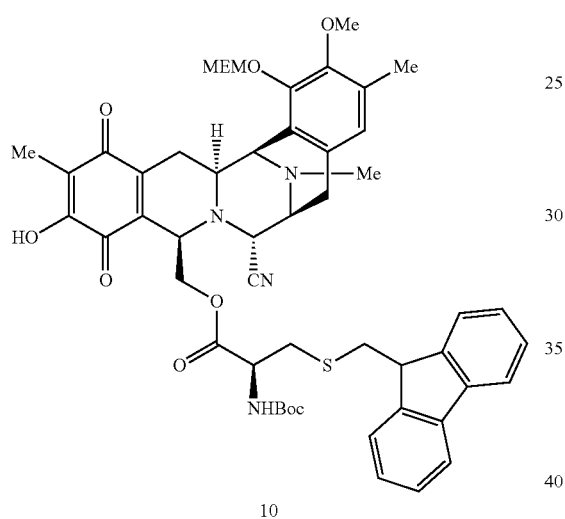

10

A solution of 9a (194 mg, 0.2 mmol) in 2,4,6-collidine (4.3 mL, 21.5 mL/mmol) was degasified and LiI (401 mg, 3.0 mmol) was added at 23° C. The reaction mixture was stirred for 24 h at 23° C., diluted with CH$_2$Cl$_2$, and washed with HCl 1M. The combined organic layers were dried over Na$_2$SO$_4$, filtered, and concentrated under vacuum. The crude was purified by column flash chromatography over SiO$_2$ eluted with Hexane:EtOAc (from 50:50 to 40:60) to afford pure 10 (115 mg, 57% yield).

$^1$H-NMR (CDCl$_3$, 300 MHz): δ 7.74-7.57 (m, 4H), 7.40-7.28 (m, 4H), 6.58 (s, 1H), 5.29-5.14 (m, 2H), 5.00 (m, 1H), 4.43 (m, 1H), 4.21 (bs, 1H), 4.09-3.79 (m, 8H), 3.69 (s, 3H), 3.58 (t, 2H, J=4.8 Hz), 3.39 (s, 3H), 3.32 (m, 1H), 3.14-2.88 (m, 5H), 2.53 (d, 1H, J=18.6 Hz), 2.38 (m, 1H), 2.28 (s, 3H), 2.17 (s, 3H), 1.85 (s, 3H), 1.39 (s, 9H).

$^{13}$C-NMR (CDCl$_3$, 75 MHz): δ 184.9, 181.1, 170.6, 154.7, 151.0, 148.8, 148.3, 145.7, 145.6, 140.9, 132.7, 131.1, 130.3, 127.6, 127.0, 124.8, 123.1, 119.9, 117.4, 117.1, 98.2, 80.2, 71.7, 69.3, 63.1, 60.0, 59.3, 59.0, 56.1, 55.8, 55.3, 55.1, 52.8, 46.7, 41.4, 36.7, 34.8, 29.7, 28.2, 25.2, 24.8, 15.8, 8.0.

MS (ES): m/z 935.3 [M+1]$^+$.

Route B

Scheme VIII provides another example of the synthesis of intermediate 10.

Scheme VIII

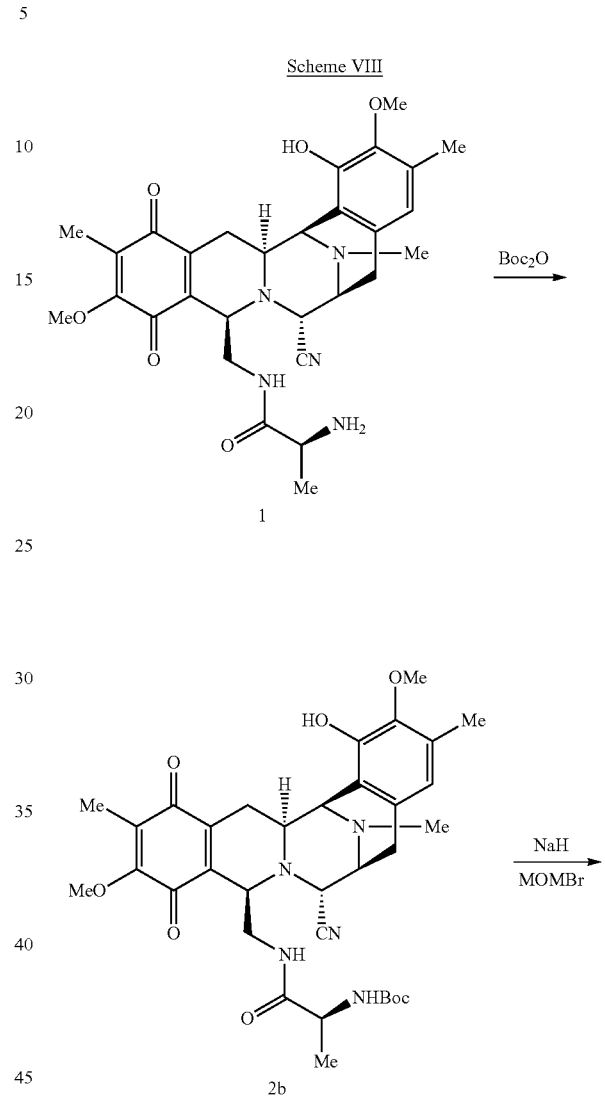

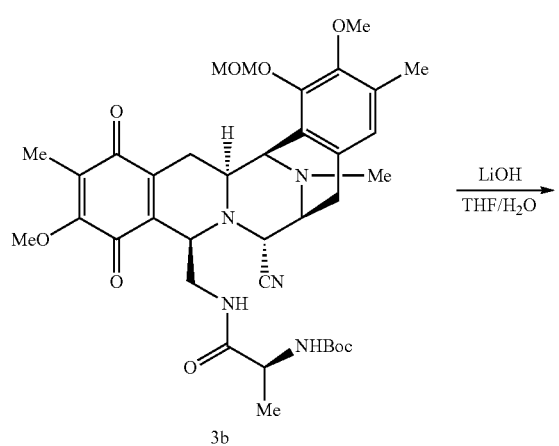

3b

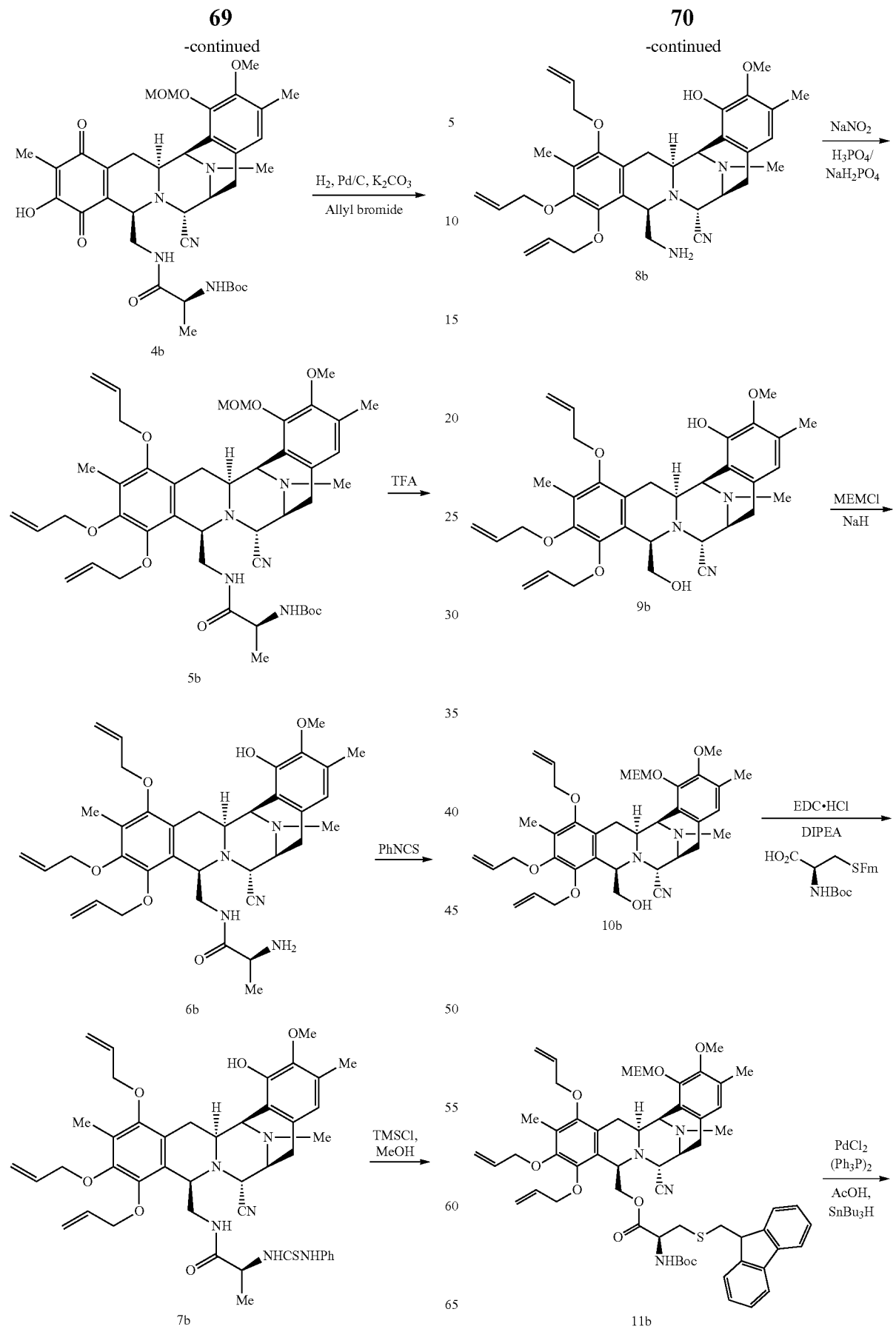

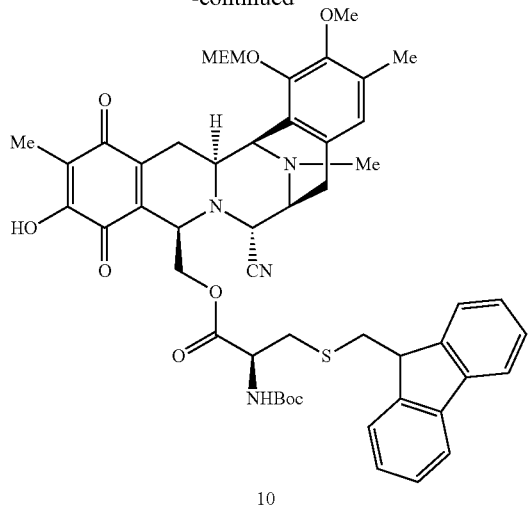

Synthesis of Intermediate 5b

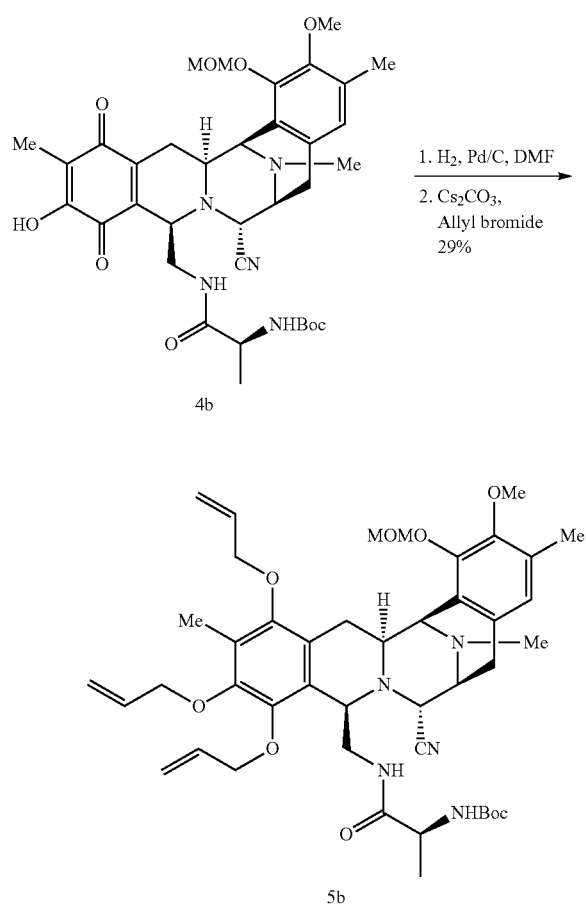

Compound 4b was obtained as disclosed in WO 00/69862. A suspension of 4b (1.14 g, 1.68 mmol) and 10% Palladium on Carbon (228 mg, 20% w/w) in anhydrous DMF (15 mL) was stirred for 2 h at 23° C. under a H₂ atmosphere. The reaction mixture was filtered through Celite® to a flask containing anhydrous Cs₂CO₃ (3.28 g, 10.1 mmol), washed with DMF (10 mL), and allyl bromide (2.9 mL, 33.6 mol) added at 23° C. The reaction mixture was stirred for 3 h at 23° C., was filtered through Celite®, and washed with CH₂Cl₂. The combined organic layers were washed with an aqueous saturated solution of NaCl, dried over anhydrous Na₂SO₄, filtered, and concentrated to dryness in vacuo by rotary evaporation. The resulting crude was purified by column flash chromatography over SiO₂ eluted with Hexane:EtOAc (from 70:30 to 50:50) to afford pure 5b (384 mg, 29% yield).

$^1$H-NMR (300 MHz, CDCl₃): δ 6.70 (s, 1H), 6.05 (m, 3H), 5.51 (bs, 1H), 5.38-5.17 (m, 6H), 5.11 (s, 2H), 4.88, (bs, 1H), 4.62-463 (m, 3H), 4.30-4.01 (m, 6H), 3.73 (s, 3H), 3.56 (s, 3H), 3.52-3.16 (m, 6H), 3.04 (dd, J=18.0 and 7.9 Hz, 1H), 2.56 (d, J=18.0 Hz, 1H), 2.31 (s, 3H), 2.25 (s, 3H), 2.14 (s, 3H), 1.82 (m, 1H), 1.30 (s, 9H), 0.98 (d, J=6.9 Hz, 1H).

$^{13}$C-NMR (75 MHz, CDCl₃): δ 171.8, 154.8, 150.1, 148.7, 148.5, 148.4, 144.5, 133.9, 133.8, 133.8, 130.9, 130.2, 125.1, 125.0, 124.8, 124.6, 124.0, 118.0, 117.9, 117.5, 117.2, 99.2, 79.3, 77.2, 73.7, 73.6, 73.4, 59.9, 59.7, 57.7, 57.7, 57.2, 56.7, 56.1, 55.1, 49.6, 43.0, 41.5, 28.1, 26.3, 25.4, 18.7, 15.7, 9.8.

MS (ES): m/z 802.4 [M+1]⁺.

Synthesis of Intermediate 6b

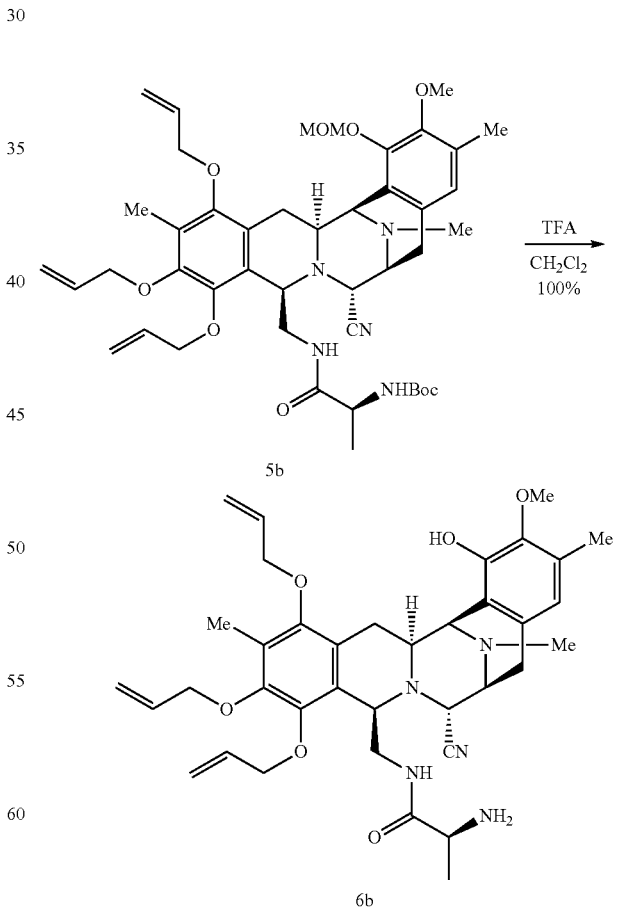

To a solution of 5b (370 mg, 0.46 mmol) in CH₂Cl₂ (7.6 mL), TFA (1.42 mL, 18.4 mmol) was added at 23° C. The reaction mixture was stirred for 1.5 h at 23° C. and concentrated to dryness in vacuo by rotary evaporation. The crude obtained was dissolved with CH$_2$Cl$_2$, neutralized by addition of an aqueous saturated solution of K$_2$CO$_3$ until basic pH, and extracted with CH$_2$Cl$_2$. The combined organic layers were dried over anhydrous Na$_2$SO$_4$, filtered, and concentrated to dryness in vacuo by rotary evaporation to give crude 6b (340 mg, 100% yield) which was used in the next step without further purification $^1$H-NMR (300 MHz, CDCl$_3$): δ 6.55 (m, 1H), 6.49 (s, 1H), 6.15-5.99 (m, 3H), 5.37-5.11 (m, 7H), 4.60-4.03 (m, 9H), 3.76 (s, 3H), 3.46-3.17 (m, 5H), 3.04-2.87 (m, 3H), 2.60 (d, J=18.3 Hz, 1H), 2.30 (s, 3H), 2.25 (s, 3H), 2.16 (s, 3H), 1.96-1.88 (m, 1H).

MS (ES): m/z 658.3 [M+1]$^+$.

Synthesis of Intermediate 7b

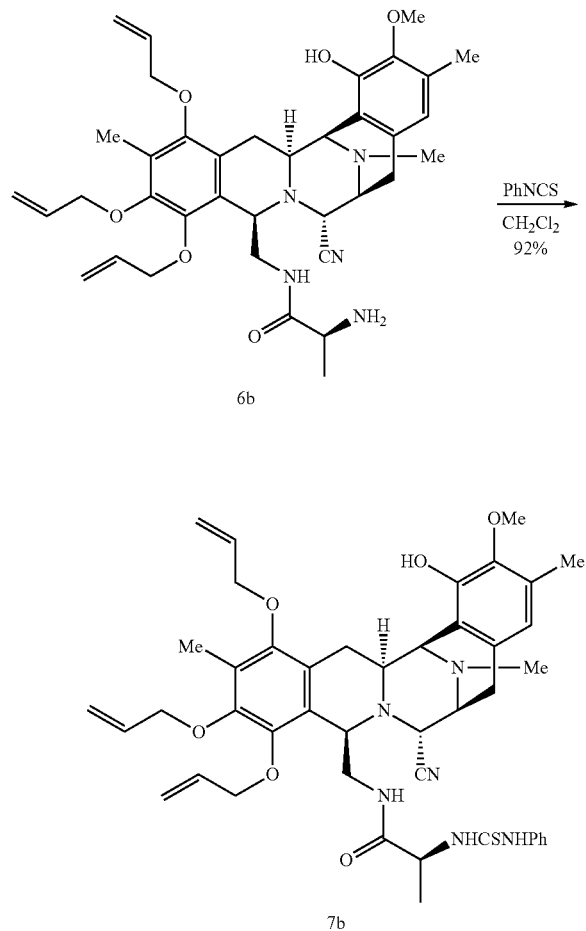

A solution of 6b (236 mg, 0.3 mmol) and phenyl isothiocyanate (0.21 mL, 1.8 mmol) in CH$_2$Cl$_2$ (65.7 mL) was stirred for 2 h at 23° C. The reaction mixture was loaded into a column flash chromatography over SiO$_2$ eluted with Hexane:EtOAc (from 90:10 to 40:60) to afford pure 7b (220 mg, 92% yield).

$^1$H-NMR (300 MHz, CDCl$_3$): δ 7.65 (s, 1H), 7.39 (t, J=7.5 Hz, 2H), 7.15 (d, J=7.5 Hz, 2H), 6.93 (d, J=7.5 Hz, 1H), 6.30 (s, 1H), 6.13-5.96 (m, 3H), 5.79 (s, 1H), 5.45-5.11 (m, 8H), 4.62-4.34 (m, 3H), 4.34-3.99 (m, 8H), 3.77 (s, 3H), 3.56 (m, 2H), 3.35-3.16 (m, 4H), 3.0 (dd, J=18.0 and 7.9 Hz, 1H), 2.50 (d, J=18.0 Hz, 1H), 2.28 (s, 3H), 2.19 (s, 3H), 2.14 (s, 3H), 1.84 (m, 1H), 0.96 (d, J=6.9 Hz, 1H).

Synthesis of Intermediate 8b

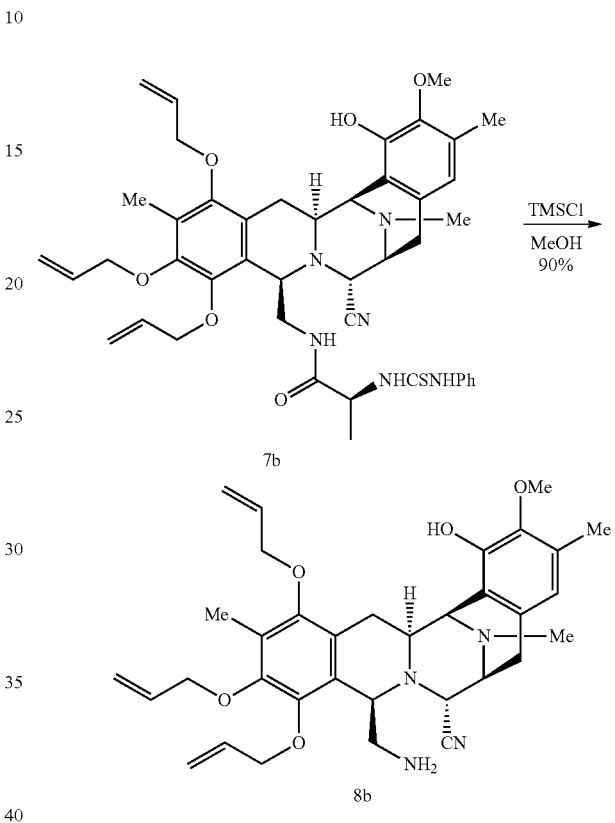

To a solution of 7b (295 mg, 0.32 mmol) in MeOH (2.5 mL), chlorotrimethylsilane (0.24 mL, 1.92 mmol) was added at 23° C. The reaction mixture was stirred for 1.5 h at 23° C. and concentrated to dryness in vacuo by rotary evaporation. The crude obtained was dissolved with EtOAc, HCl 1M was added until acid pH, and extracted with EtOAc. The aqueous layer was basified with solid K$_2$CO$_3$ and extracted with CH$_2$Cl$_2$. The combined organic layers were dried over anhydrous Na$_2$SO$_4$, filtered, and concentrated to dryness in vacuo by rotary evaporation to obtain crude 8b (196 mg, 90% yield) which was used in the next step without further purification.

$^1$H-NMR (300 MHz, CDCl$_3$): δ 6.52 (s, 1H), 6.15-5.97 (m, 3H), 5.43-5.19 (m, 6H), 4.63-4.42 (m, 3H), 4.31-4.10 (m, 7H), 3.76 (s, 3H), 3.34-3.22 (m, 3H), 3.10 (dd, J=18.2 and 7.6 Hz, 1H), 2.80 (m, 1H), 2.62 (d, J=17.7 Hz, 1H), 2.35 (s, 3H), 2.26 (s, 3H), 2.17 (s, 3H), 1.77 (m, 1H).

$^{13}$C-NMR (75 MHz, CDCl$_3$): δ 150.7, 149.0, 146.8, 144.6, 143.2, 134.2, 134.0, 130.8, 129.4, 125.3, 121.3, 118.6, 118.2, 117.8, 117.8, 117.0, 74.3, 73.7, 61.0, 60.7, 57.5, 56.8, 55.7, 46.3, 41.9, 29.9, 26.5, 25.8, 16.1, 10.3, four carbon signals overlap.

Synthesis of Intermediate 9b

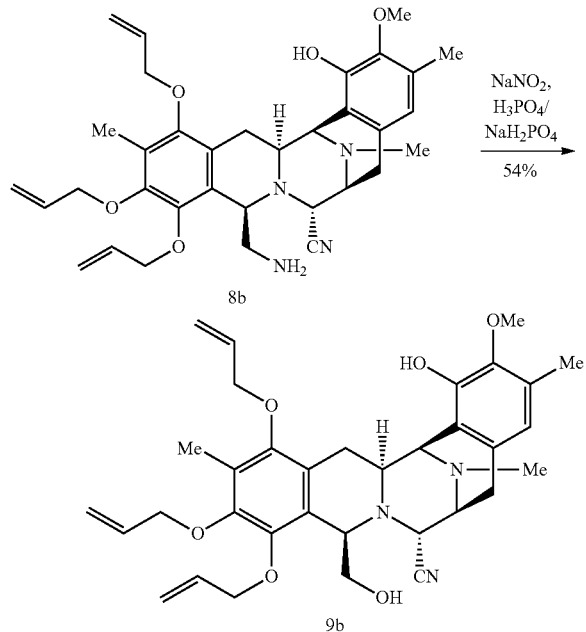

To a mixture of 8b (120 mg, 0.21 mmol) and $H_3PO_4$: $Na_2HPO_4$ solution (0.63 mL, 8.6 mL $H_2O$:0.151 g $H_3PO_4$: 1.6 g $Na_2HPO_4$) in $CH_2Cl_2$ (1.3 mL), an aqueous solution of $NaNO_2$ (7.9 mL, 0.31 mmol, 20%) was slowly added over 1 h at 23° C. The reaction mixture was stirred for 18 h at 23° C., diluted with $H_2O$, and extracted with $CH_2Cl_2$. The combined organic layers were dried over anhydrous $Na_2SO_4$, filtered, and concentrated to dryness in vacuo by rotary evaporation. The crude was purified by column flash chromatography over $SiO_2$ eluted with Hexane:EtOAc (from 70:30 to 60:40) to afford pure 9b (68 mg, 54% yield).

$^1$H-NMR (300 MHz, $CDCl_3$): δ 6.49 (s, 1H), 6.16-5.97 (m, 3H), 5.79 (s, 1H), 5.44-5.18 (m, 6H), 4.61-4.41 (m, 3H), 4.31-4.18 (m, 4H), 4.05 (m, 2H), 3.73 (s, 3H), 3.59 (m, 1H), 3.35-3.08 (m, 6H), 2.53 (d, J=18.0 Hz, 1H), 2.36 (s, 3H), 2.24 (s, 3H), 2.15 (s, 3H), 1.84 (m, 1H).

$^{13}$C-NMR (75 MHz, $CDCl_3$): δ 150.1, 148.5, 146.6, 144.5, 143.0, 134.0, 133.9, 130.3, 129.0, 125.7, 125.0, 124.4, 120.7, 117.9, 117.5, 117.4, 117.3, 116.8, 77.2, 74.0, 73.6, 73.5, 65.9, 60.8, 60.7, 58.5, 57.1, 56.7, 55.4, 41.6, 26.0, 25.8, 15.7, 9.9.

Synthesis of Intermediate 10b

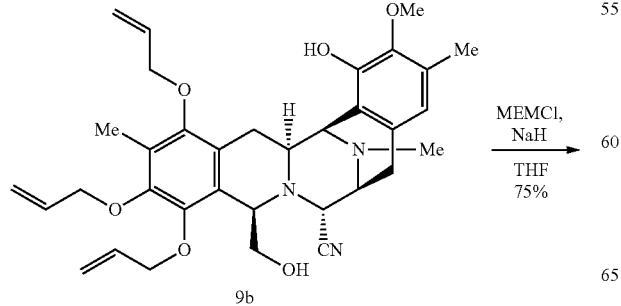

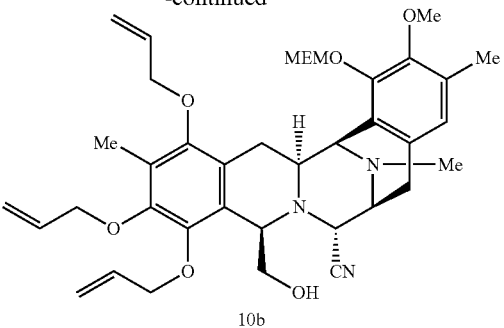

To a solution of 9b (20 mg, 0.033 mmol) in THF (0.2 mL), 1-chloromethoxy-2-methoxyethane (4.4 μL, 0.039 mmol) and NaH (1.5 mg, 0.038 mmol, 60% dispersion in mineral oil) were added at 0° C. The reaction mixture was stirred for 1 h at 23° C., catalytic amount of NaH was added and the stirring was maintained for an additional 1 h at 23° C. Then the reaction mixture was diluted with an aqueous saturated solution of NaCl, and extracted with $CH_2Cl_2$. The combined organic layers were dried over anhydrous $Na_2SO_4$, filtered, and concentrated to dryness in vacuo by rotary evaporation. The crude was purified by column flash chromatography over $SiO_2$ eluted with Hexane:EtOAc (from 70:30 to 60:40) to afford pure 10b (16.5 mg, 75% yield).

$^1$H-NMR (300 MHz, $CDCl_3$): δ 6.72 (s, 1H), 6.16-5.97 (m, 3H), 5.47-5.16 (m, 8H), 4.61-4.41 (m, 3H), 4.30-4.19 (m, 4H), 4.05-3.81 (m, 4H), 3.68 (s, 3H), 3.59 (m, 4H), 3.39 (s, 3H), 3.34-3.10 (m, 5H), 2.50 (d, J=18.0 Hz, 1H), 2.37 (s, 3H), 2.20 (s, 3H), 2.14 (s, 3H), 1.78 (m, 1H).

MS (ES): m/z 676.2 [M+1]$^+$.

Synthesis of Intermediate 11b

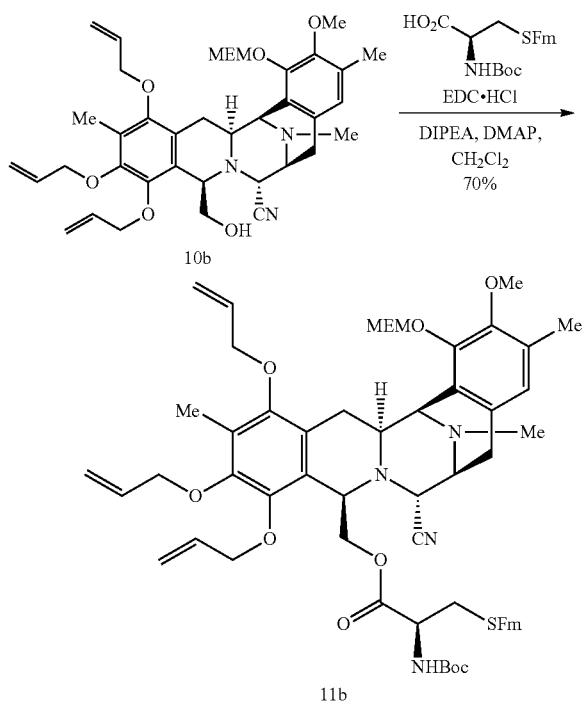

To a solution of 10b (75 mg, 0.11 mmol) and Boc-L-Cys (Fm)-OH (88 mg, 0.22 mmol) in $CH_2Cl_2$ (2.3 mL), DIPEA (38 μL, 0.22 mmol), N-(3-dimethylaminopropyl)-N-ethylcarbodiimide hydrochloride (63 mg, 0.33 mmol) and DMAP (13 mg, 0.11 mmol) were added at 23° C. The reaction mixture was stirred for 3 h at 23° C., diluted with $CH_2Cl_2$, and washed with an aqueous saturated solution of $NaHCO_3$. The combined organic layers were dried over anhydrous $Na_2SO_4$, filtered, and concentrated to dryness in vacuo by rotary evaporation. The crude was purified by column flash chromatography over $SiO_2$ eluted with Hexane:EtOAc (from 70:30 to 60:40) to afford pure 11b (81 mg, 70% yield).

$^1$H-NMR (300 MHz, $CDCl_3$): δ 7.76-7.61 (m, 4H), 7.38-7.26 (m, 4H), 6.60 (s, 1H), 6.12-5.96 (m, 3H), 5.44-5.13 (m, 8H), 4.53-3.82 (m, 13H), 3.70 (s, 3H), 3.57 (m, 2H), 3.38 (s, 3H), 3.25-2.83 (m, 8H), 2.63-2.48 (m, 2H), 2.30 (s, 3H), 2.17-2.14 (m, 6H), 1.72 (m, 1H), 1.44 (s, 9H).

$^{13}$C-NMR (75 MHz, $CDCl_3$): δ 170.6, 154.9, 150.2, 150.1, 148.5, 148.4, 148.2, 145.7, 144.8, 144.7, 140.9, 140.9, 134.0, 133.84, 133.76, 130.5, 127.6, 127.0, 125.3, 124.9, 124.8, 124.1, 123.7, 119.9, 118.2, 118.0, 117.5, 117.4, 117.3, 98.2, 80.1, 77.2, 73.9, 73.4, 71.7, 69.3, 61.4, 59.7, 59.0, 57.2, 56.9, 56.3, 55.4, 53.4, 46.9, 46.8, 41.5, 37.0, 35.4, 29.7, 28.3, 26.2, 25.5, 23.6, 15.7, 9.9.

Synthesis of Intermediate 10 from Intermediate 11b

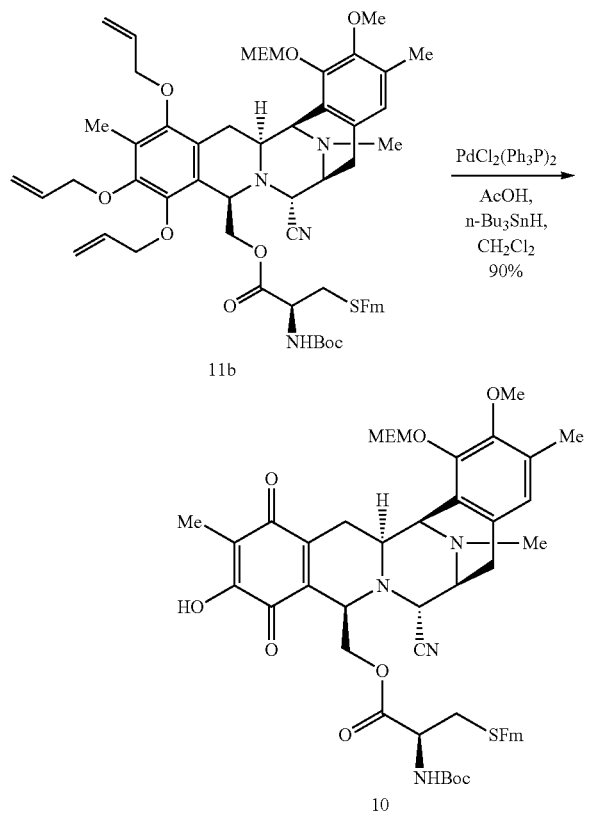

To a suspension of 11b (13 mg, 0.013 mmol) and $PdCl_2(Ph_3P)_2$ (1.5 mg, 0.0021 mmol) in $CH_2Cl_2$ (0.3 mL), AcOH (7 μL, 0.13 mmol) and n-$Bu_3SnH$ (21 μL, 0.078 mmol) were added at 23° C. The reaction mixture was stirred for 45 minutes at 23° C. and loaded into a column flash chromatography over $SiO_2$ eluted with different mixtures of Hexane:EtOAc (90:10, 70:30, 40:60) to afford pure 10 (10.4 mg, 90% yield).

$^1$H-NMR ($CDCl_3$, 300 MHz): δ 7.74-7.57 (m, 4H), 7.40-7.28 (m, 4H), 6.58 (s, 1H), 5.29-5.14 (m, 2H), 5.00 (m, 1H), 4.43 (m, 1H), 4.21 (bs, 1H), 4.09-3.79 (m, 8H), 3.69 (s, 3H), 3.58 (t, 2H, J=4.8 Hz), 3.39 (s, 3H), 3.32 (m, 1H), 3.14-2.88 (m, 5H), 2.53 (d, 1H, J=18.6 Hz), 2.38 (m, 1H), 2.28 (s, 3H), 2.17 (s, 3H), 1.85 (s, 3H), 1.39 (s, 9H).

$^{13}$C-NMR ($CDCl_3$, 75 MHz): δ 184.9, 181.1, 170.6, 154.7, 151.0, 148.8, 148.3, 145.7, 145.6, 140.9, 132.7, 131.1, 130.3, 127.6, 127.0, 124.8, 123.1, 119.9, 117.4, 117.1, 98.2, 80.2, 71.7, 69.3, 63.1, 60.0, 59.3, 59.0, 56.1, 55.8, 55.3, 55.1, 52.8, 46.7, 41.4, 36.7, 34.8, 29.7, 28.2, 25.2, 24.8, 15.8, 8.0.

MS (ES): m/z 935.3 $[M+1]^+$.

Example 2

Synthesis of ET-743

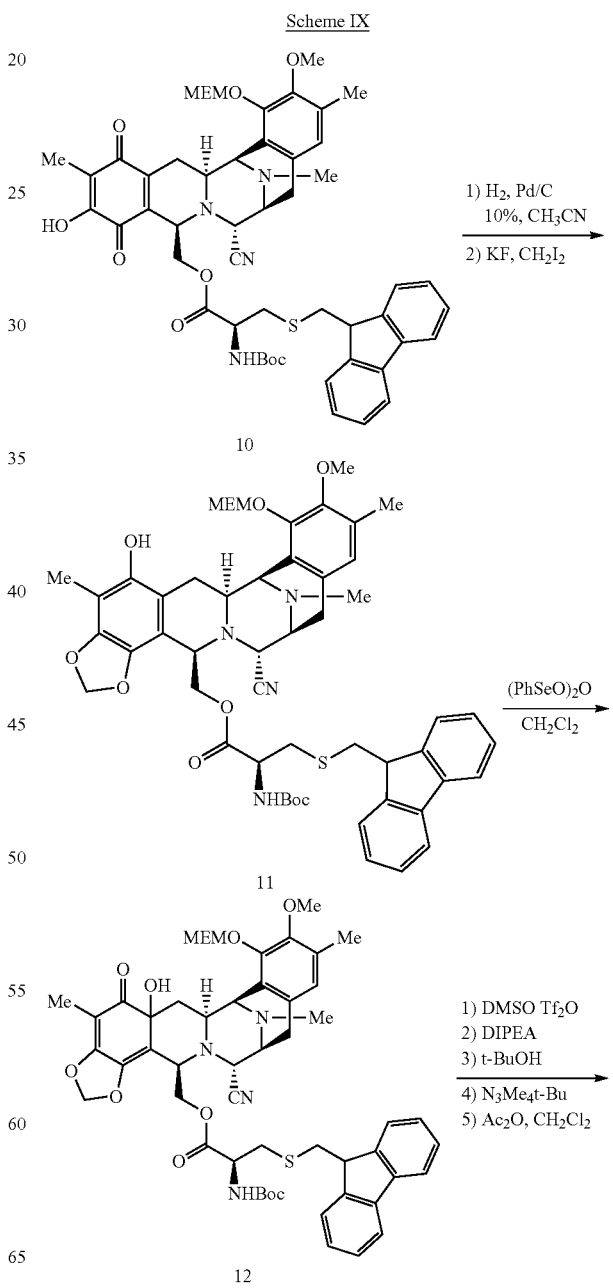

-continued

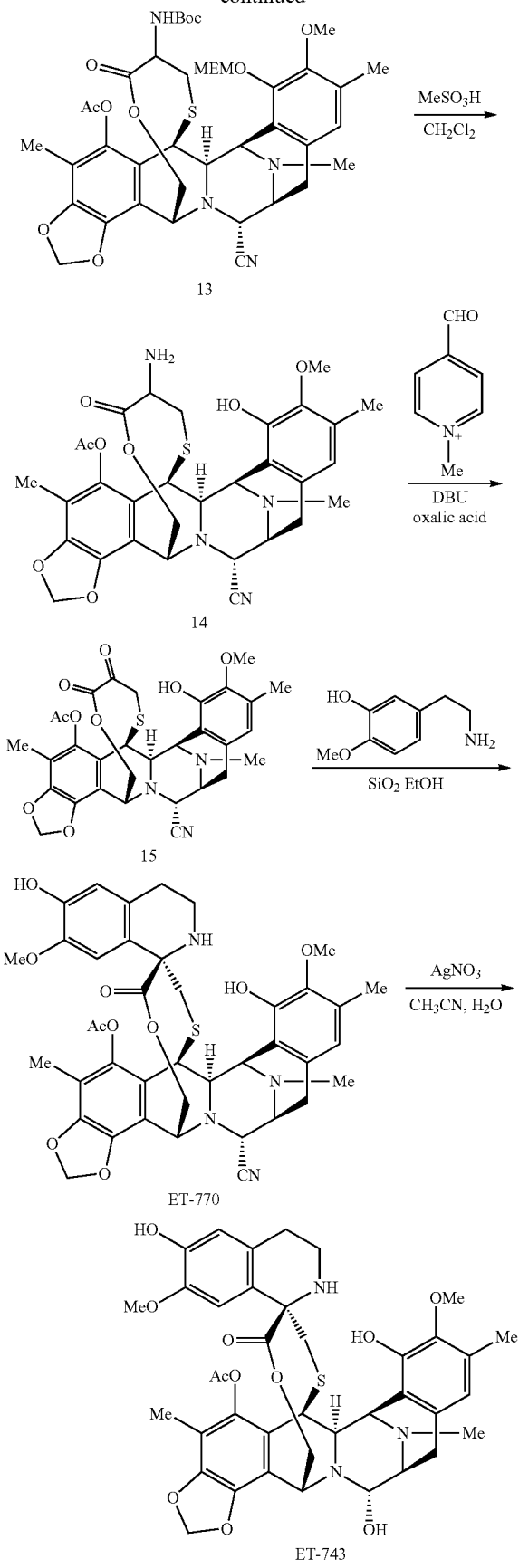

Scheme IX above provides an example of the synthesis of ET-743 from intermediate 10.

Synthesis of Intermediate 11

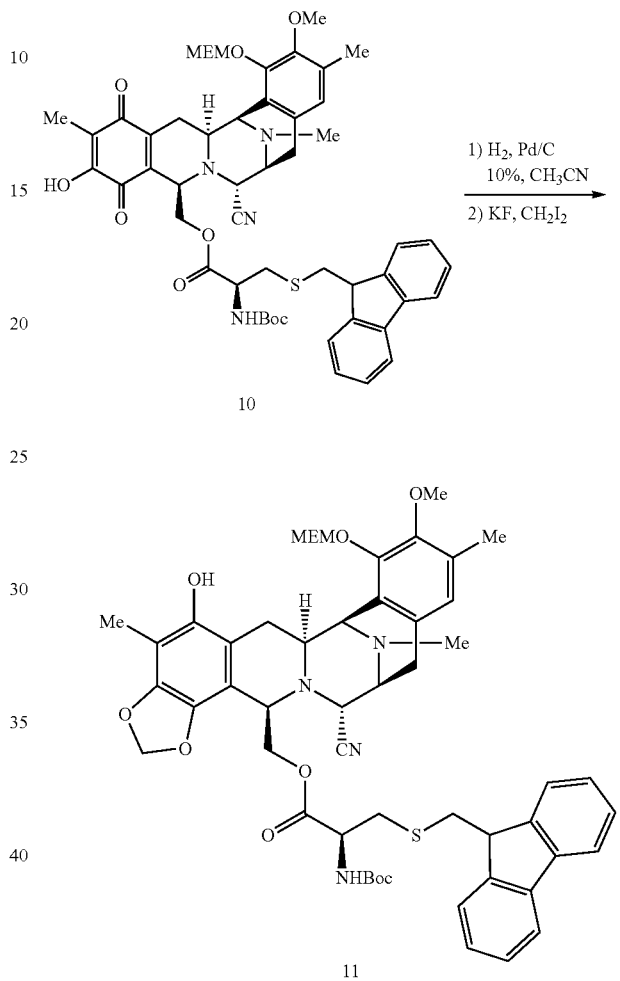

A suspension of 10 (56 mg, 0.06 mmol) and Pd on carbon (17 mg, 10%) in anhydrous $CH_3CN$ (3.0 mL, 51 mL/mmol) was stirred under a hydrogen atmosphere for 2.5 h at 23° C. The reaction mixture was filtered through a 0.45 μm PTFE filter over KF (34 mg, 0.6 mmol), washed with $CH_3CN$ (2 mL), and diiodomethane (0.19 mL, 2.4 mmol) was added at 23° C. The reaction mixture was heated for 20 h at 70° C., diluted with $CH_2Cl_2$, and washed with an aqueous saturated solution of NaCl. The combined organic layers were dried over $Na_2SO_4$, filtered, and concentrated under vacuum. The crude was purified by column flash chromatography over $SiO_2$ eluted with $CH_2Cl_2$:EtOAc (from 90:10 to 80:20) to afford pure 11 (20 mg, 36% yield) which exhibited spectroscopic and spectrometric characteristics identical to those reported for this compound in WO 01/87895.

Compounds 12, 13, 14, 15, ET-770 and ET-743 are obtainable following the procedures described in WO 00/69862, WO 01/87895 and WO 03/008423.

Example 3
Synthesis of Compound 17
Scheme X
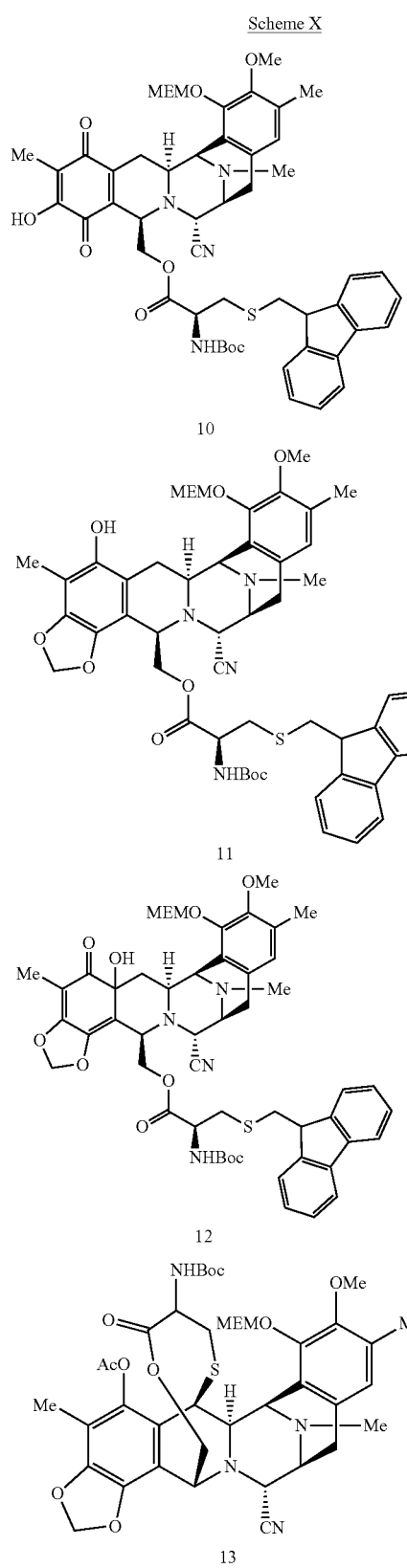
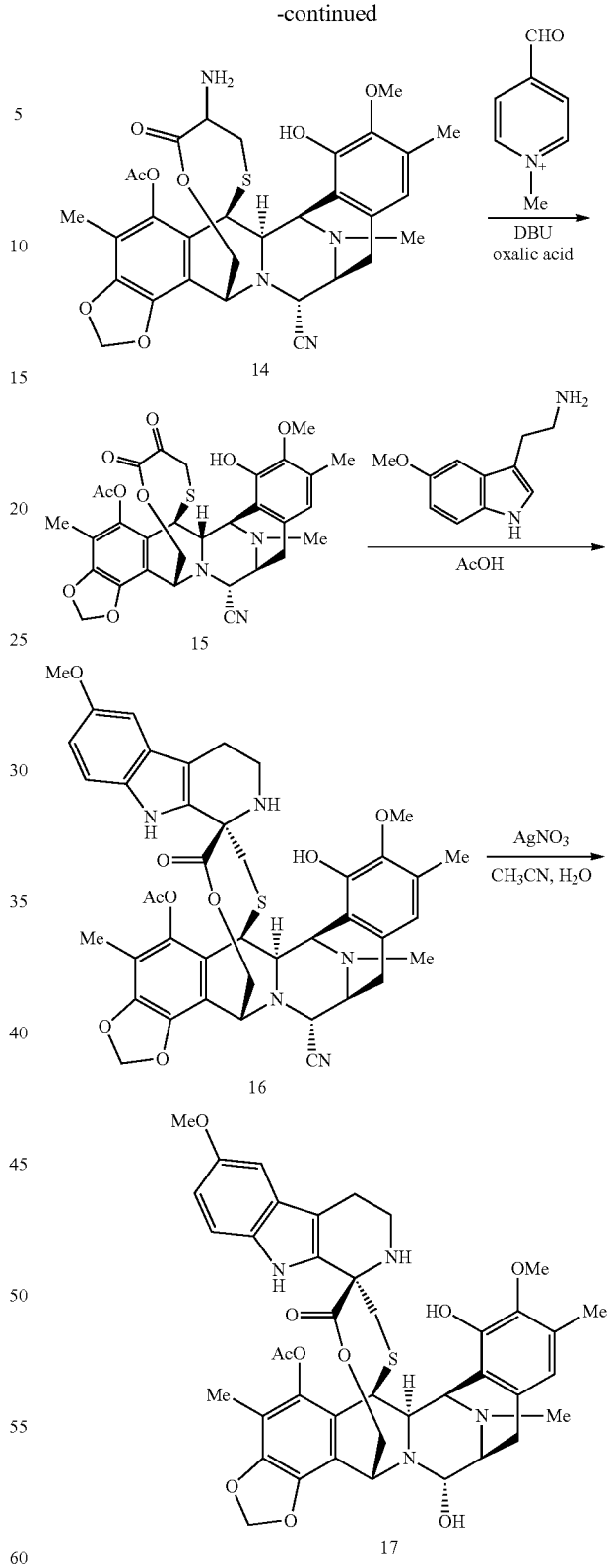
Scheme X above provides an example of the synthesis of compound 17 from intermediate 10.
Compounds 16 and 17 are obtainable from intermediate 15 using the same procedures than those previously described in WO03/014127.

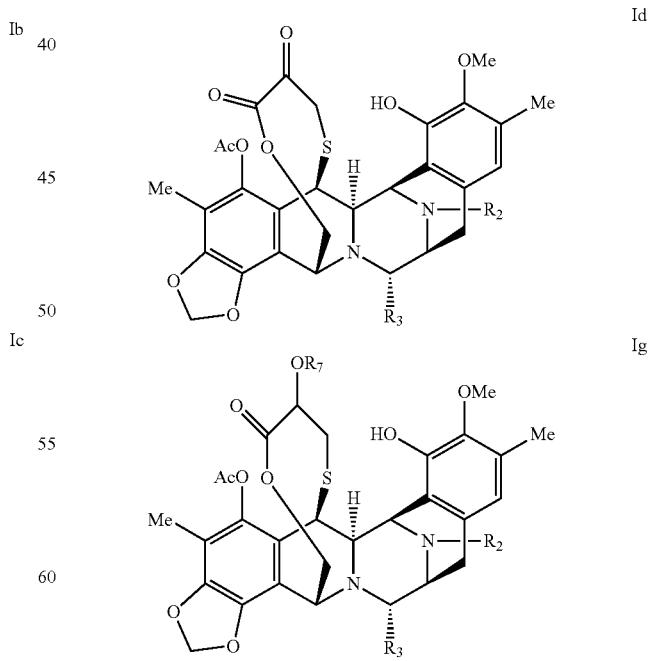

wherein
$R_7$ is selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for OH.
20. A process according to claim 19, which further comprises the step of replacement of the cyano group at $R_3$ in the compound of formula Ig by a hydroxy group:
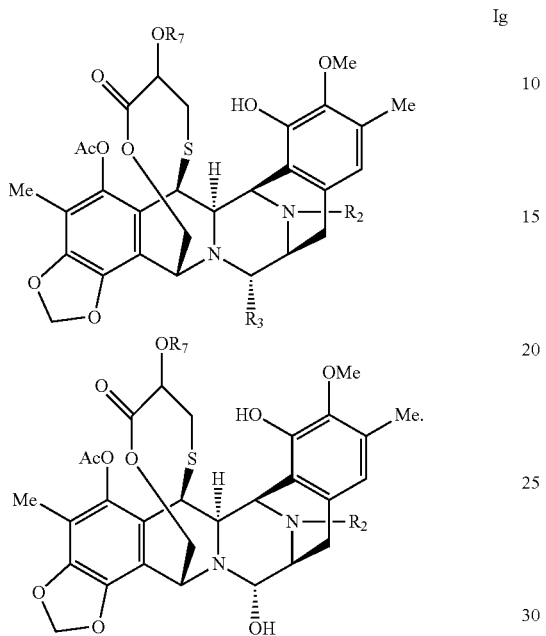

The invention claimed is:

1. A process comprising the step of reducing a quinone of formula II to form a hydroquinone, followed by alkylation of the resulting hydroquinone with a suitable electrophilic reagent to give a compound of formula IIa:

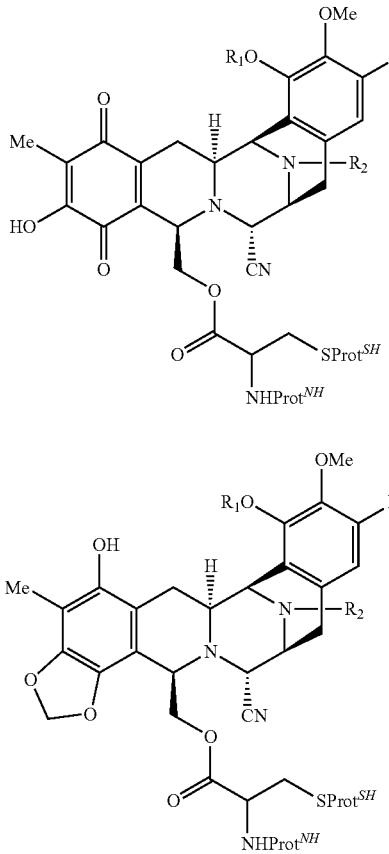

wherein
$R_1$ is a protecting group for OH;
$R_2$ is selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, C(=O)$R^a$, C(=O)O$R^b$, C(=O)N$R^c R^d$, and a protecting group for amino;
$R^a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;
$R^b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for OH;
$R^c$ and $R^d$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for amino;
$Prot^{NH}$ is a protecting group for amino; and
$Prot^{SH}$ is a protecting group for SH.

2. A process according to claim 1, which further comprises the step of oxidising the compound of formula IIa to give a compound of formula IIb:

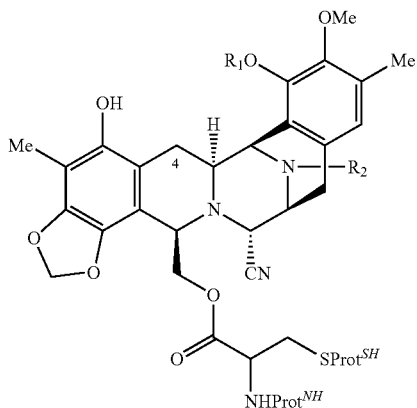

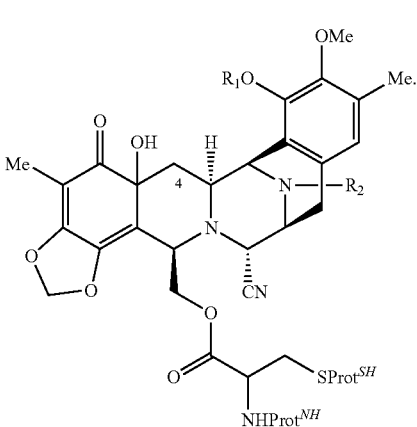

3. A process according to claim 2, which further comprises the step of forming a bridged ring system to provide a compound of formula Ia:

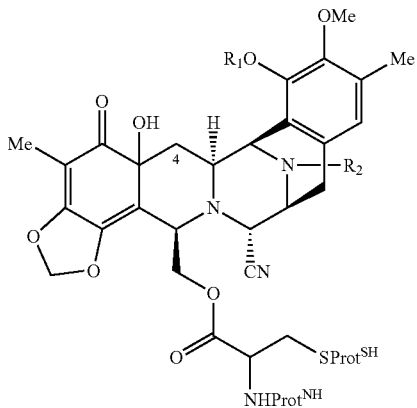

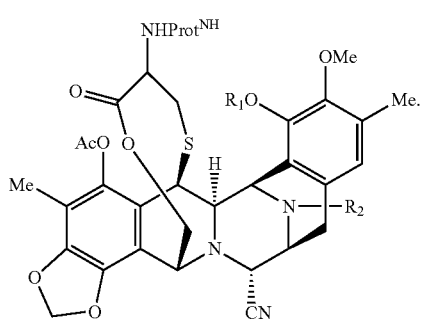

4. A process according to claim 1 wherein Prot$^{SH}$ is an S-9-fluorenylmethyl (Fm) group.

5. A process according to claim 3, which further comprises the step of deprotecting a compound of formula Ia to give a compound of formula Ib:

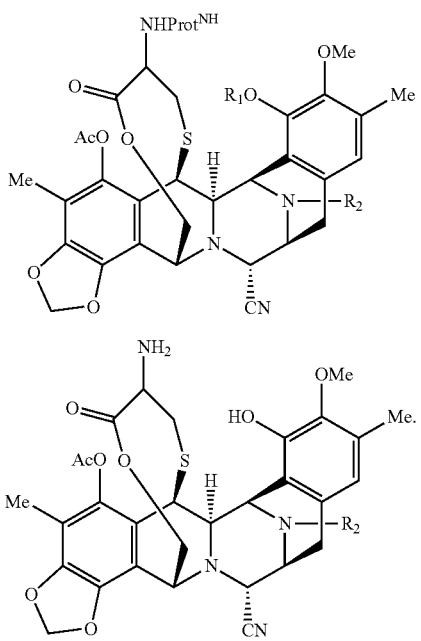

6. A process according to claim 1 wherein $R_1$ is a methoxyethoxymethyl group and Prot$^{NH}$ is a t-butoxycarbonyl group.

7. A process according to claim 5, which further comprises the step of oxidising the α-aminolactone of formula Ib to the corresponding α-ketolactone of formula Id by transamination:

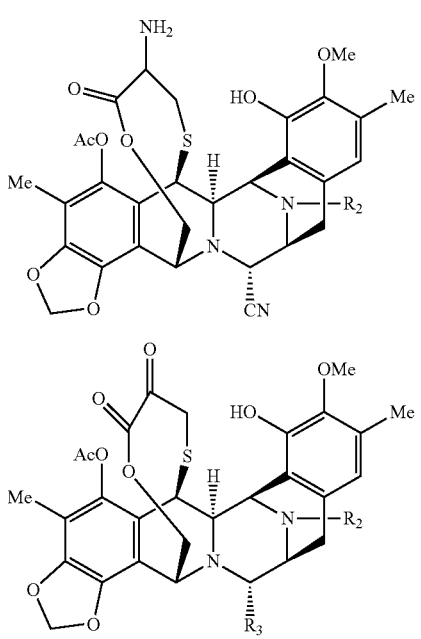

wherein $R_3$ is cyano.

8. A process according to claim 7, which further comprises the step of stereospecifically forming a spirotetrahydroisoquinoline compound of formula If from the α-ketolactone of formula Id by a Pictet-Spengler reaction with the following compound:

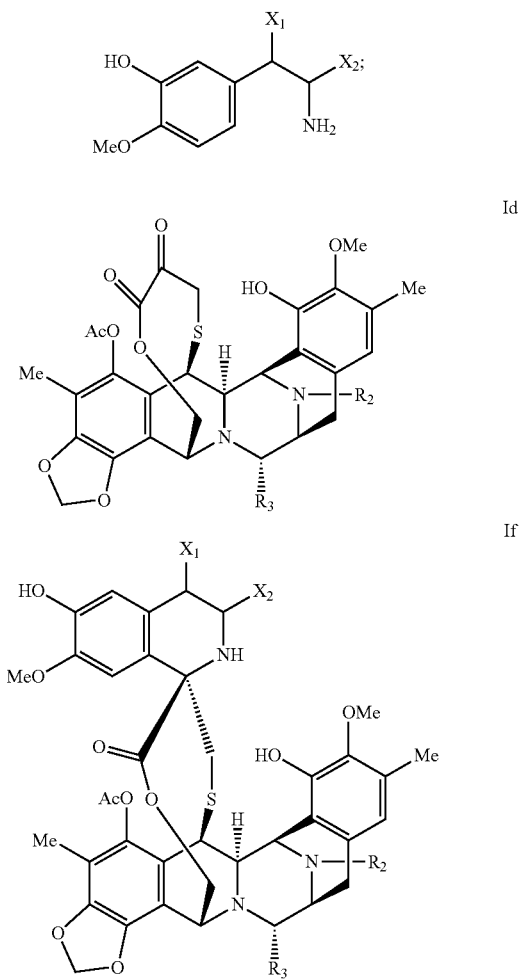

wherein
$X_1$, and $X_2$ are as independently selected from hydrogen and substituted or unsubstituted $C_1$-$C_{12}$ alkyl.

9. A process according to claim 8, which further comprises the step of replacement of the cyano group at $R_3$ in the compound of formula If by a hydroxy group:

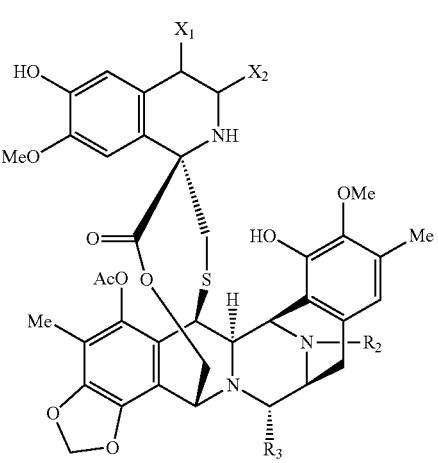

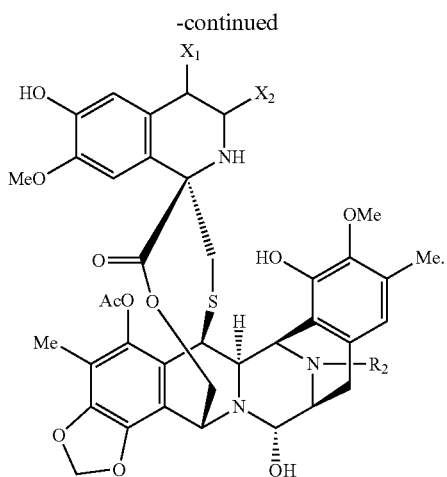

10. A process according to claim 8 wherein $X_1$ and $X_2$ are H.

11. A process according to claim 7, which further comprises the step of stereospecifically forming a spirotetrahydro-1H-pyrido[3,4-b]indole compound of formula Ie from the α-ketolactone of formula Id by a Pictet-Spengler reaction with the following compound:

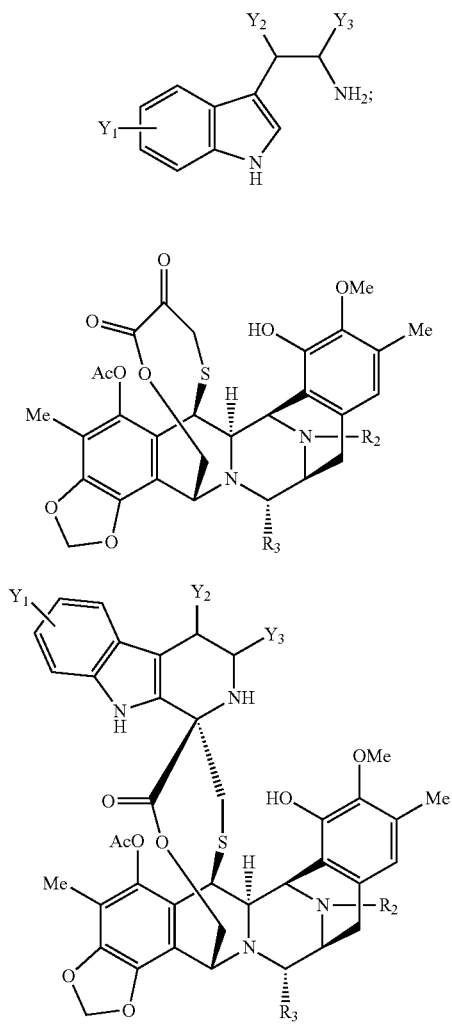

wherein $Y_1$ is selected from hydrogen, $OR^b$, $OC(=O)R^a$, $OC(=O)OR^b$, $OC(=O)NR^cR^d$, $SR^e$, $SOR^a$, $SO_2R^a$, $C(=O)R^a$, $C(=O)OR^b$, $C(=O)NR^cR^d$, $NO_2$, $NR^cR^d$, $N(R^c)C(=O)R^a$, $N(R^c)$—$OR^b$, $C(R^a)=NOR^b$, $N(R^c)C(=O)OR^b$, $N(R^c)C(=O)NR^cR^d$, CN, halogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group;

$Y_2$, and $Y_3$ are independently selected from hydrogen and substituted or unsubstituted $C_1$-$C_{12}$ alkyl; and $R^e$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for SH.

12. A process according to claim 11, which further comprises the step of replacement of the cyano group at $R_3$ in the compound of formula Ie by a hydroxy group:

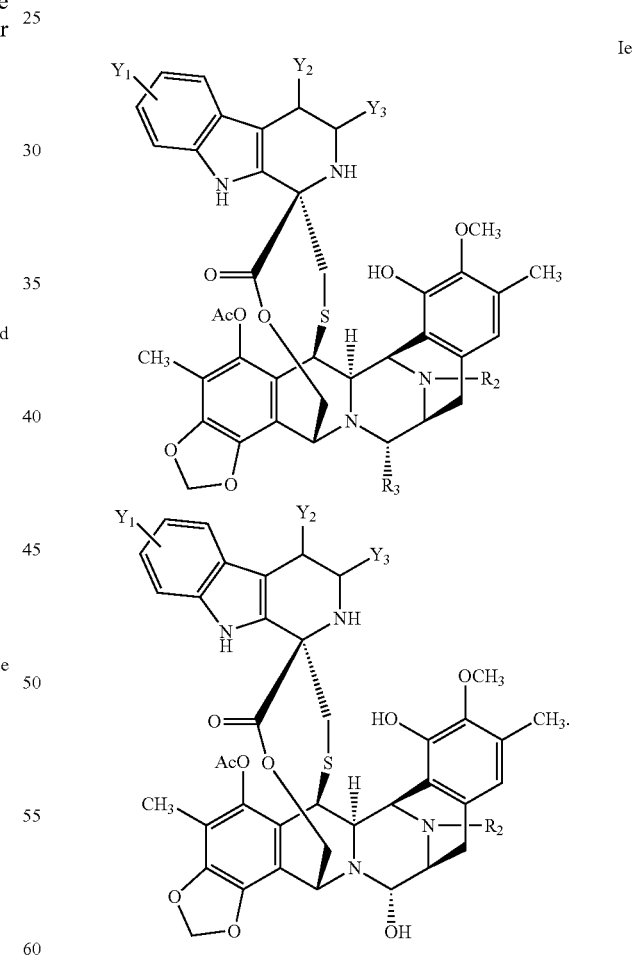

13. A process according to claim 11 wherein $Y_1$ is hydrogen or methoxy, and $Y_2$ and $Y_3$ are hydrogen.

14. A process according to claim 1, wherein $R_2$ is methyl.

15. A process according to claim 9 wherein the compound of formula If is ET-743:

ET-743

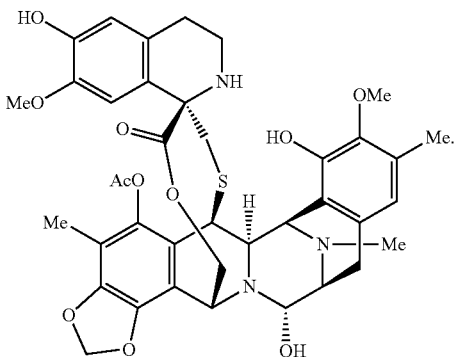

16. A process according to claim 12, wherein the compound of formula Ie is:

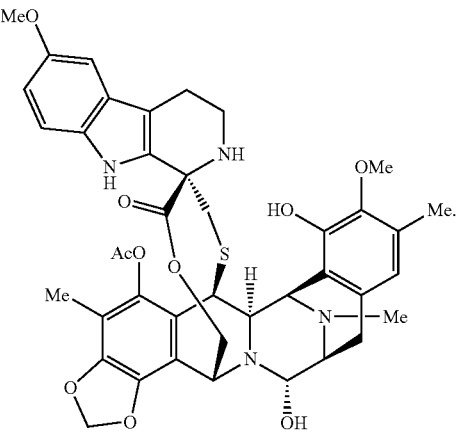 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

17. A process according to claim 5, which further comprises the step of converting a compound of formula Ib into a compound of formula Ic by reaction with a compound of formula $R_8LG$ and a compound of formula $R_9LG$:

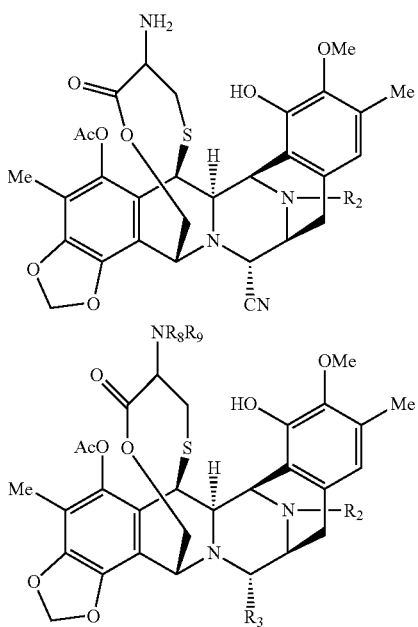

wherein
$R_3$ is cyano;
$R_8$ and $R_9$ are independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, substituted or unsubstituted heterocyclic group, and a protecting group for amino; and
LG is a leaving group.

18. A process according to claim 17, which further comprises the step of replacement of the cyano group at $R_3$ in the compound of formula Ic by a hydroxy group:

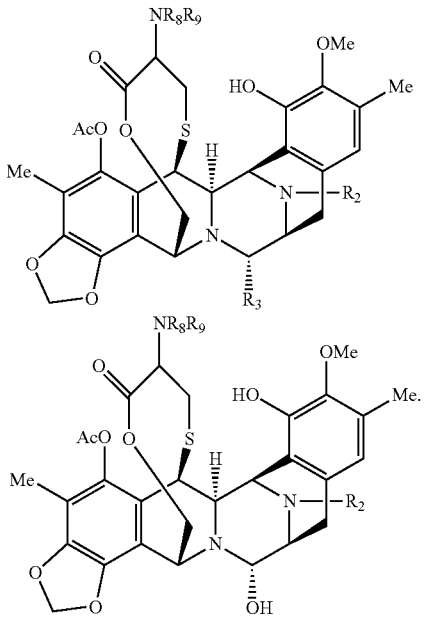

19. A process according to claim 7, which further comprises the step of reducing the α-ketolactone of formula Id to the corresponding α-hydroxylactone followed by reaction with a compound of formula $R_7LG$ to produce a compound of formula Ig: